(12) United States Patent
Björck et al.

(10) Patent No.: US 8,889,128 B2
(45) Date of Patent: Nov. 18, 2014

(54) USE OF THE ENDOGLYCOSIDASE ENDOS FOR TREATING IMMUNOGLOBULIN G MEDIATED DISEASES

(75) Inventors: Lars Björck, Lund (SE); Mattias Collin, Lund (SE); Arne Olsén, Onsala (SE); Rikard Holmdahl, Lund (SE); Kutty Selva Nandakumar, Tamilnadu (IN); Oonagh Shannon, Veberod (SE)

(73) Assignee: Hansa Medical AB, Lund (SE)

( * ) Notice: Subject to any disclaimer, the term of this patent is extended or adjusted under 35 U.S.C. 154(b) by 1099 days.

(21) Appl. No.: 12/518,855

(22) PCT Filed: Dec. 12, 2007

(86) PCT No.: PCT/EP2007/010904
§ 371 (c)(1),
(2), (4) Date: Jan. 20, 2010

(87) PCT Pub. No.: WO2008/071418
PCT Pub. Date: Jun. 19, 2008

(65) Prior Publication Data
US 2010/0135981 A1 Jun. 3, 2010

(30) Foreign Application Priority Data
Dec. 13, 2006 (GB) .................................. 0624874.4

(51) Int. Cl.
*A61K 38/48* (2006.01)
*A61K 39/02* (2006.01)

(52) U.S. Cl.
USPC ................... 424/94.63; 424/190.1; 424/234.1

(58) Field of Classification Search
None
See application file for complete search history.

(56) References Cited

FOREIGN PATENT DOCUMENTS

| JP | 2006-520202 A | 9/2006 |
|---|---|---|
| WO | WO 03/051914 A2 | 6/2003 |
| WO | WO 2006/042027 A | 4/2006 |

OTHER PUBLICATIONS

Collin et al. Embo Journal 20:3046-3055, 2001.*
Schmaldienst et al. Rheumatology, 40:513-521, 2001.*
Naparstek and Plotz. Annual Reviews of Immunology, 11:79-104, 1993.*
Collin, Mattias et al., "EndoS and SpeB from *Streptococcus pyogenes* Inhibit Immunoglobulin-Mediated Opsonophagocytosis," Infection and Immunity, 2002, vol. 70, No. 12, pp. 6646-6651.
Collin, Mattias et al., "Effect of EndoS and SpeB from *Streptococcus pyogenes* on Human Immunoglobulins," Infection and Immunity, 2001, vol. 69, No. 11, pp. 7187-7189.
Office Action in corresponding Japanese Patent Application No. 2009-540659, mailed Nov. 2, 2012, 17 pages.

* cited by examiner

*Primary Examiner* — Oluwatosin Ogunbiyi
(74) *Attorney, Agent, or Firm* — Kilpatrick Townsend & Stockton LLP

(57) ABSTRACT

The invention provides use of an EndoS polypeptide, or a polynucleotide encoding an EndoS polypeptide, in the manufacture of a medicament for the treatment or prevention of a disease or condition mediated by IgG antibodies.

7 Claims, 23 Drawing Sheets

Fig. 2

| Fig. 2A | Fig. 2B |
| Fig. 2C | Fig. 2D |
| Fig. 2E | Fig. 2F |

USE OF THE ENDOGLYCOSIDASE ENDOS FOR TREATING IMMUNOGLOBULIN G MEDIATED DISEASES

FIELD OF THE INVENTION

The present invention relates to a method for treating or preventing diseases or conditions mediated by IgG antibodies, such as autoimmune diseases, transplant rejection, post-operative treatment and acquired haemophilia.

BACKGROUND OF THE INVENTION

IgG is a heterotetramer composed of two heavy chains and two light chains held together by disulfide bonds forming three protein domains separated by a flexible and protease sensitive hinge region. The two identical Fab portions bind antigens and the single Fc portion is responsible for effector functions, including binding and activation of complement factor C1q and Fc receptors on leukocytes.

In addition to the polypeptide backbone the Fc portion contains a conserved glycan on each heavy chain attached to Asn-297. This oligosaccharide is of the complex biantennary type with a core fucose linked to the innermost N-acetylglucosamine (GlcNAc). These glycans are located in the interface between the $C_H2$ domains (second constant domain of the heavy chains).

EndoS is an endoglycosidase secreted by the human pathogen *Streptococcus pyogenes*. EndoS specifically hydrolyzes the asparagine-linked glycan on IgG between the two core GlcNAc residues. In contrast to many related endoglycosidases that require or are enhanced by denaturation of the glycoprotein substrate, EndoS only hydrolyzes native IgG. No other substrate for EndoS has been found to date.

SUMMARY OF THE INVENTION

The present inventors have shown that EndoS is useful in treating and preventing diseases mediated by IgG antibodies. In particular, the inventors have shown that EndoS efficiently hydrolyzes IgG in human blood and in vivo in rabbits, that deglycosylation of IgG by EndoS abrogates its arthritis-inducing capacity in mice, and that EndoS has a protective effect in a mouse model of lethal IgG-driven idiopathic thrombocytopenic purpura (ITP). EndoS pretreatment of pathogenic antibodies inhibits the development of this disease, and the enzyme also rescues mice from already established disease when severe thrombocytopenia and subcutaneous bleeding have developed.

In accordance with the present invention, there is thus provided the use of an EndoS polypeptide, or a polynucleotide encoding an EndoS polypeptide, in the manufacture of a medicament for the treatment or prevention of a disease or condition mediated by IgG antibodies.

The present invention also provides:

an EndoS peptide, or a polynucleotide encoding an EndoS polypeptide, for use in a method for treating or preventing a disease or condition mediated by IgG antibodies;

a method of treating or preventing a disease or condition mediated by IgG antibodies in a subject in need thereof, the method comprising administering to the subject a therapeutically effective amount of an EndoS polypeptide, or a polynucleotide encoding an EndoS polypeptide; and a method of treating, ex vivo, blood taken from a patient suffering from a disease or condition mediated by IgG antibodies, comprising contacting the blood with an EndoS polypeptide.

BRIEF DESCRIPTION OF THE FIGURES

FIG. 2, which is inclusive of FIG. 2A-FIG. 2F, is a ClustalW amino acid sequence alignment of EndoS homologues from different *S. pyogenes* serotypes, *S. equi* and *S. zooepidemicus*. Strain names, species, and M serotypes are shown to the left. Amino acid identities and similarities are shown in grey and the consensus sequence is shown under the alignment. The conserved chitinase motif is boxed and the glutamic acid essential for activity is marked with an asterisk below the alignment.

FIG. 3 is a ClustalW amino acid sequence alignment of the EndoS α-domain with EndoF$_2$ from *Elizabethkingia meningoseptica* (SEQ ID NO:21) and CP40 from *Corynebacterium pseudotuberculosis* (SEQ ID NO:22). Protein names are shown to the left. Amino acid identities and similarities are shown in grey and the consensus sequence (SEQ ID NO:23) is shown under the alignment. The conserved chitinase motif is boxed and the glutamic acid essential for activity is marked with an asterisk below the alignment.

FIG. 5A shows SDS-PAGE analysis of purified IgG from human blood incubated with increasing concentrations of recombinant EndoS (rEndoS). FIG. 5B shows an LCA lectin blot analysis of purified IgG from human whole blood incubated with increasing concentrations of rEndoS. FIG. 5C shows densitometric analysis of the lectin blot on IgG purified from human blood incubated with increasing concentrations of rEndoS.

FIG. 6A shows SDS-PAGE (stain) and lectin blot analysis (LCA blot) of purified IgG from serum samples withdrawn from the rabbit at indicated time point after the first intravenous injection of 500 μg of rEndoS. FIG. 6B shows SDS-PAGE (stain) and lectin blot analysis (LCA blot) of purified IgG from serum samples withdrawn from the rabbit at indicated time point after a second administration of rEndoS. FIG. 6C shows SDS-PAGE (stain) and lectin blot analysis (LCA blot) of purified IgG from serum samples withdrawn from the rabbit at indicated time point after a third administration of rEndoS.

BRIEF DESCRIPTION OF THE SEQUENCES

Figure 1:
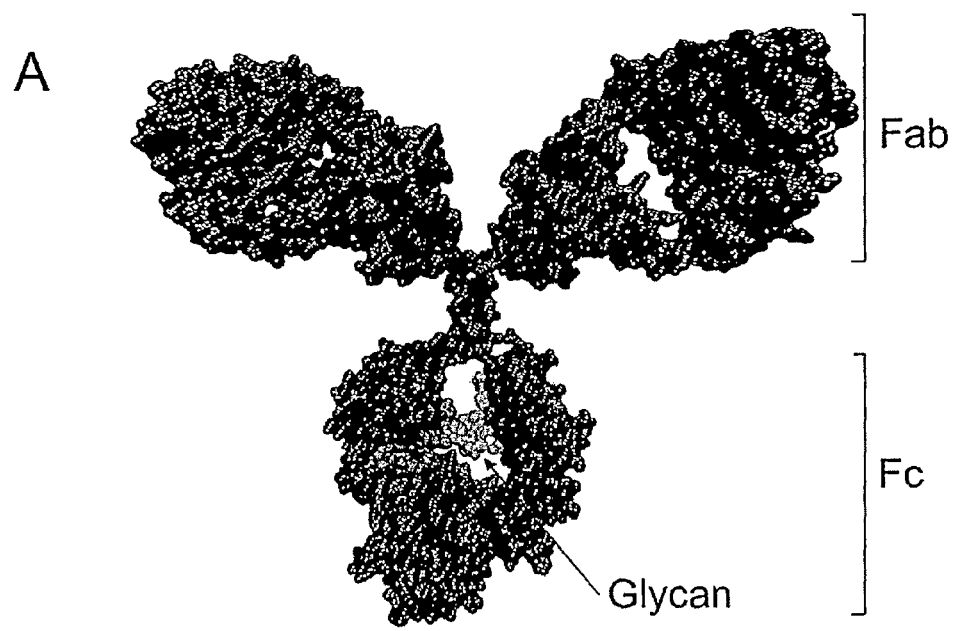
FIG. 1A is a structural model of human IgG1. Brackets indicate the antigen binding Fab portion and the Fc effector portion of IgG. The arrow indicates the two conserved glycans attached to Asn-297 of the heavy chains.
FIG. 1B is a schematic representation of the fully substituted IgG heavy chain glycan. S2 indicates the fully sialylated glycoform, G0 and bracket indicate the extent of the G0 glycoform. LCA indicates the binding site for the *Lens culinaris* agglutinin used in lectin experiments and EndoS indicates the cleavage site for the enzyme.
Figure 1:
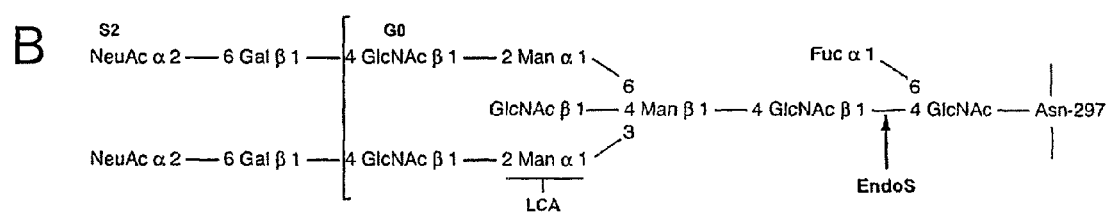
Figure 4:
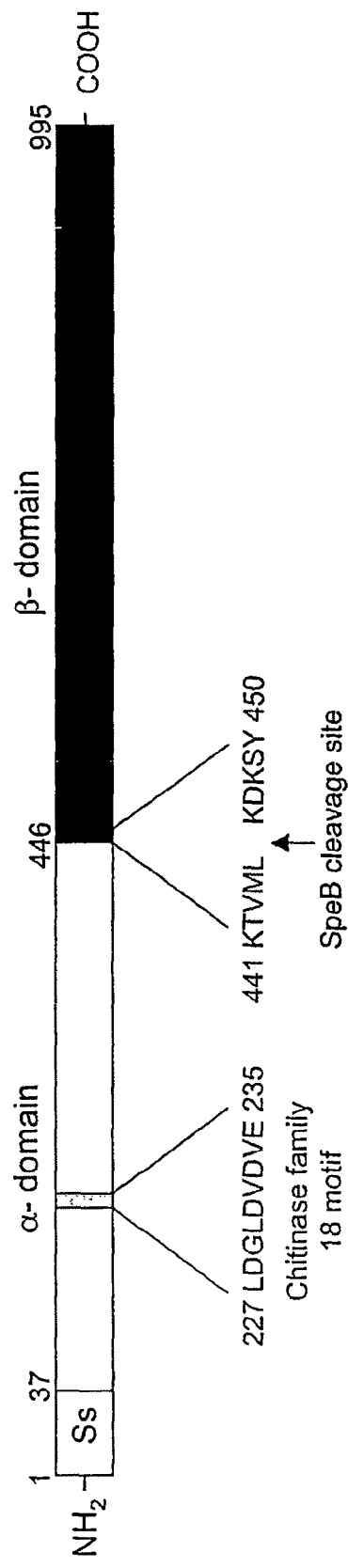
FIG. 4 shows the domain organization of EndoS. Schematic representation of the 995 amino acids of full-length EndoS (SEQ ID NO: 2). Ss indicates signal peptide, the chitinase family 18 active site motif in the α-domain (SEQ ID NO:24) is indicated, and the SpeB cleavage site (SEQ ID NO:25) generating the two domains is indicated with an arrow.

SEQ ID NO: 1 is an amino acid sequence of EndoS isolated from *S. pyogenes* AP1.

SEQ ID NO: 2 is an amino acid sequence of EndoS isolated from *S. pyogenes* AP1, including a signal sequence.

SEQ ID NO: 3 is a nucleic acid sequence encoding EndoS isolated from *S. pyogenes* AP1, including a signal sequence.

DETAILED DESCRIPTION OF THE INVENTION

The present invention provides a method for treating or preventing diseases or conditions mediated by IgG antibodies, which method comprises administering to a subject an EndoS polypeptide or a polynucleotide encoding an EndoS polypeptide.

The present inventors have found that EndoS hydrolyzes IgG in human blood and in vivo in rabbits, that deglycosylation of IgG by EndoS abrogates its arthritis—inducing capacity in mice, and that EndoS has a protective effect in a mouse model of lethal IgG-driven idiopathic thrombocytopenic purpura (ITP). EndoS pretreatment of pathogenic antibodies inhibits the development of this disease, and the enzyme also rescues mice from already established disease when severe thrombocytopenia and subcutaneous bleeding have developed. Accordingly, EndoS can be used to treat or prevent diseases or conditions mediated by IgG antibodies.

Polypeptides

Figures 2, 2A, 2C, 2E:
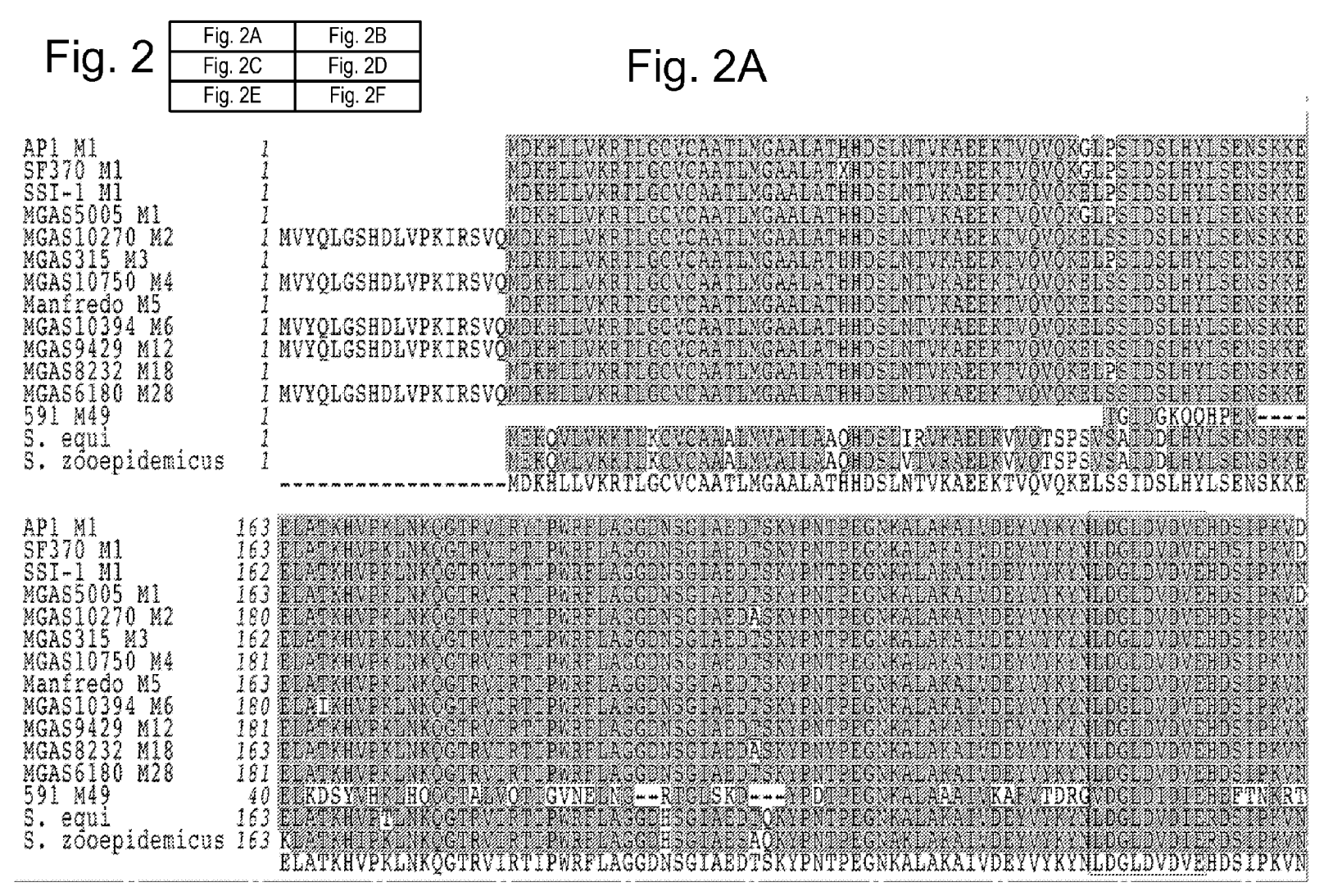
Figure 2B:
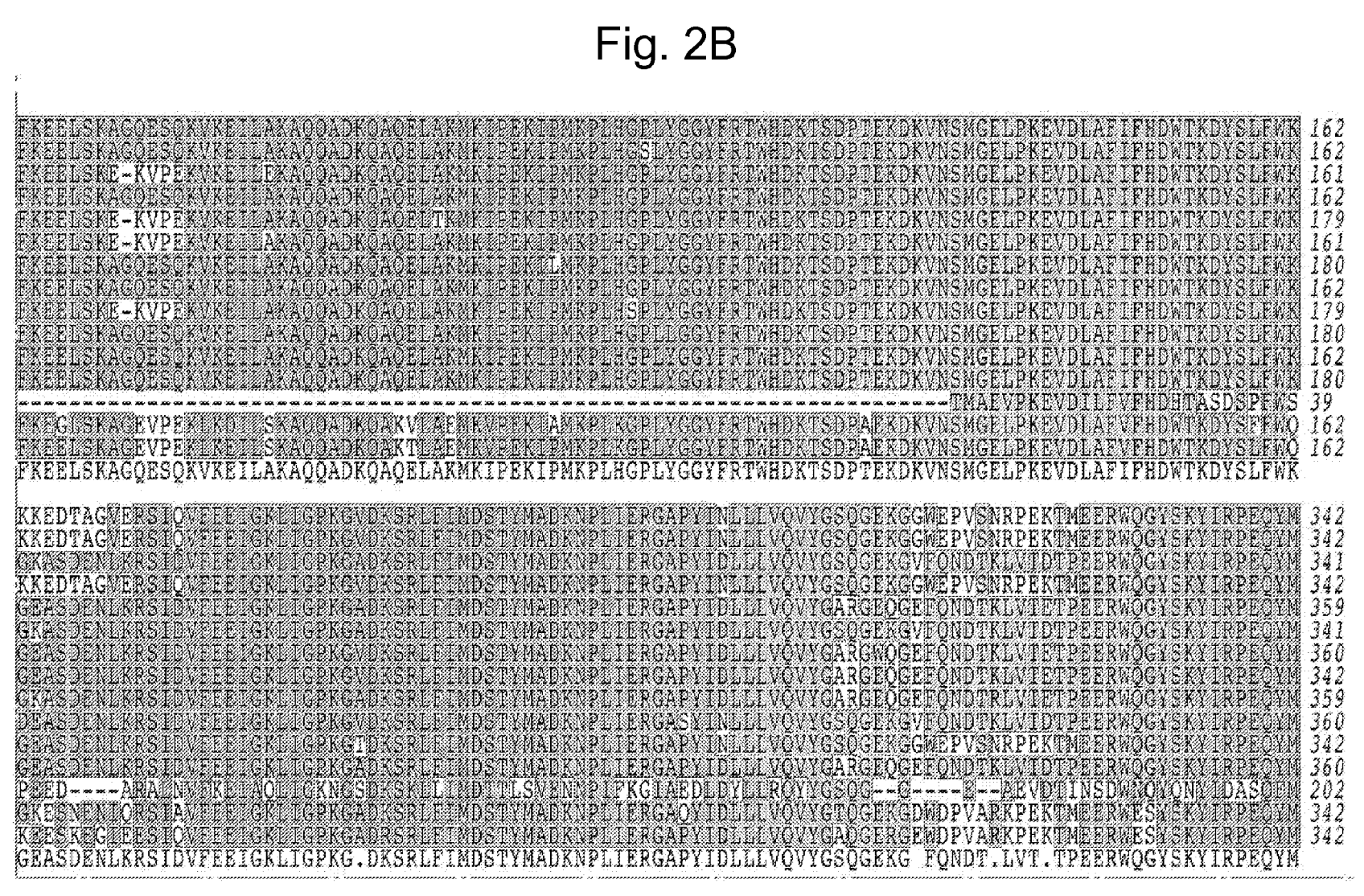
Figure 2C:
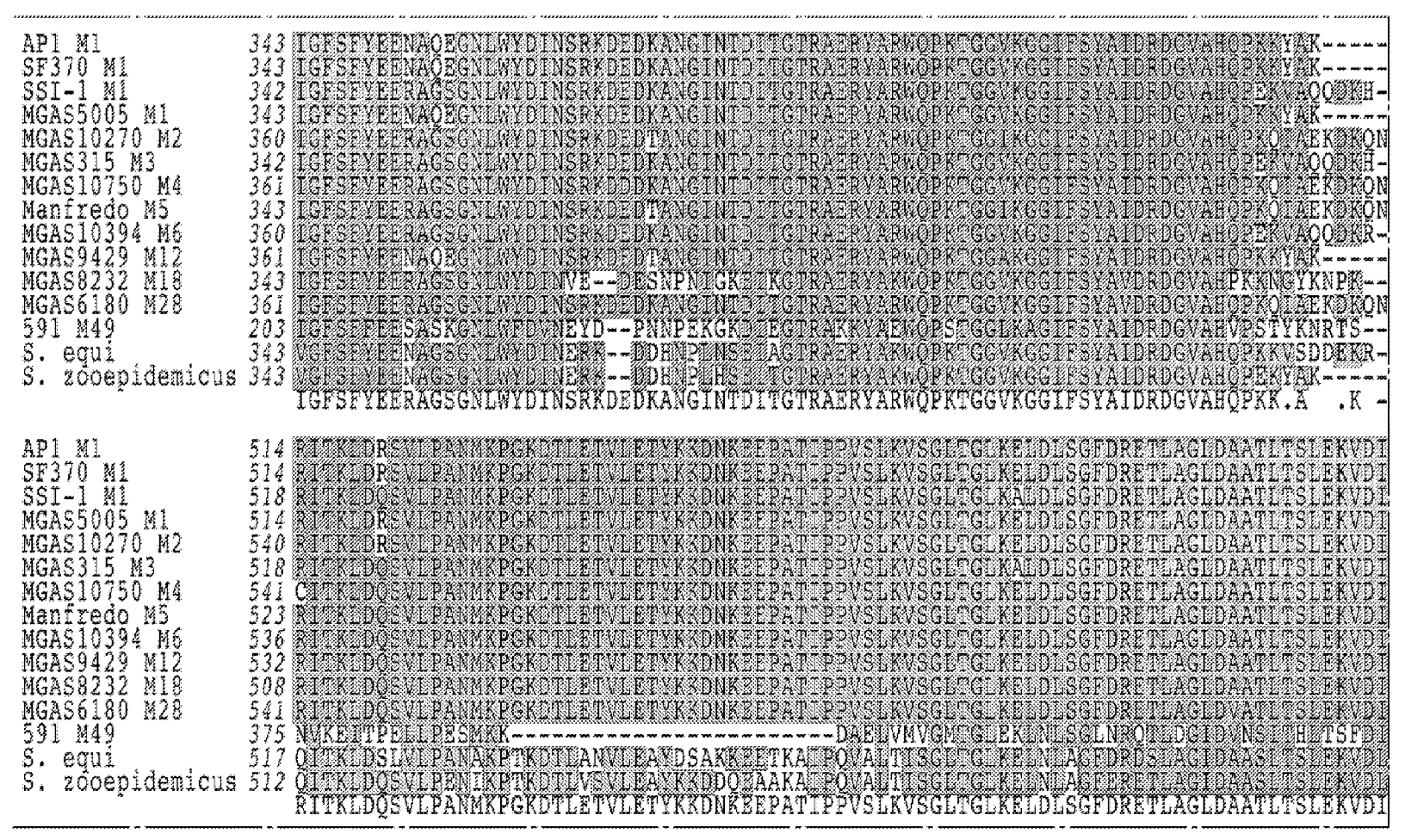
Figure 2D:
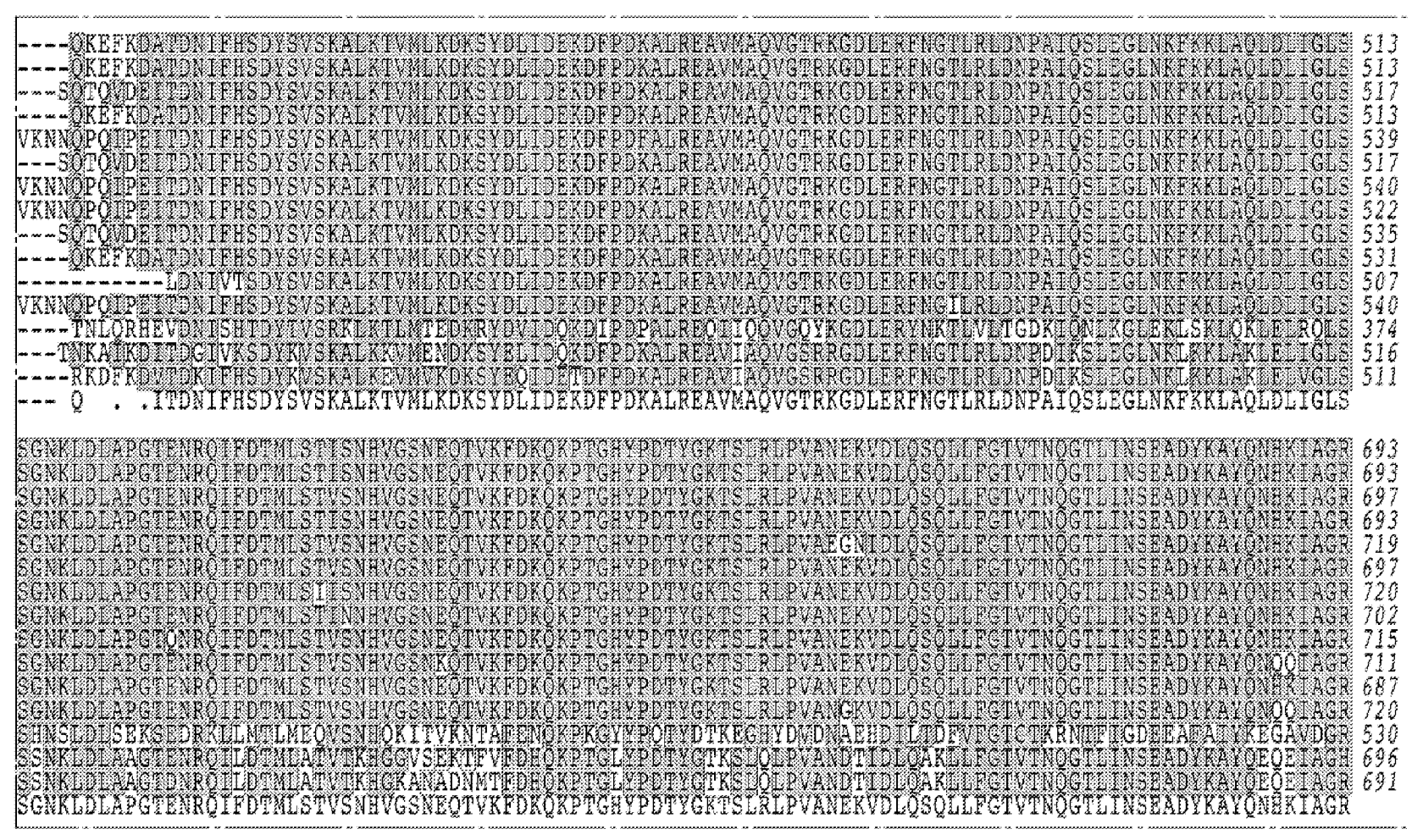
Figure 2E:
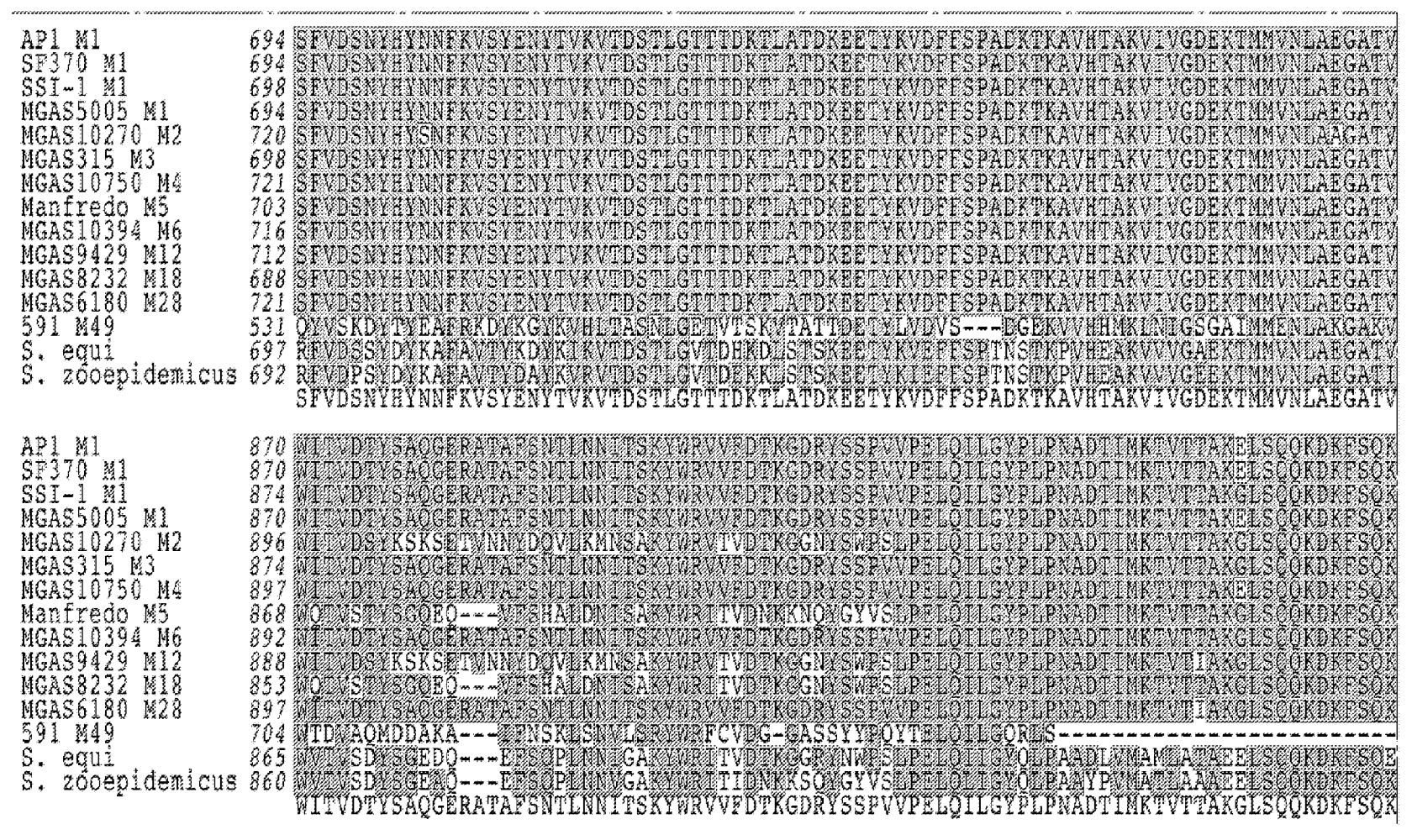
Figure 3:
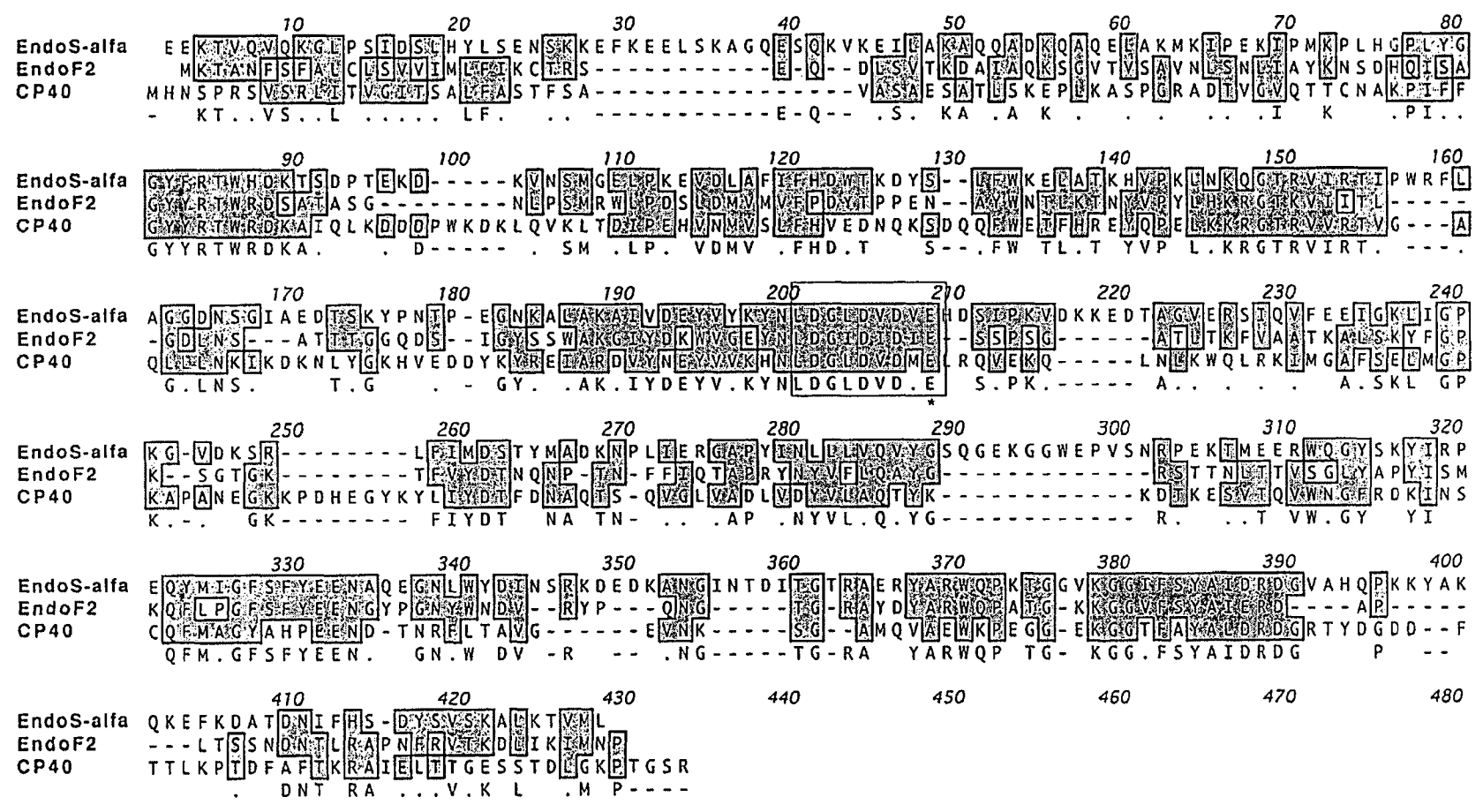

The EndoS polypeptide is preferably *S. pyogenes* EndoS, or a variant or fragment of *S. pyogenes* EndoS which retains IgG endoglycosidase activity. The variant may be an EndoS polypeptide from another organism, such as another bacterium. The bacterium is preferably a *Streptococcus*, such as *Streptococcus equi*, *Streptococcus zooepidemicus* or, preferably, *Streptococcus pyogenes*. Alternatively, the variant may be from *Corynebacterium pseudotuberculosis*, for example the CP40 protein; *Enterococcus faecalis*, for example the EndoE protein; or *Elizabethkingia meningoseptica* (formerly *Flavobacterium meningosepticum*), for example the EndoF$_2$ protein. The sequences of EndoS variants from various *S. pyogenes* serotypes and from *S. equi* and *S. zooepidemicus* are shown in FIG. 2. FIG. 3 shows an alignment of the α-domain of EndoS with EndoF$_2$ from *Elizabethkingia meningoseptica* and CP40 from *Corynebacterium pseudotuberculosis*.

The EndoS polypeptide may comprise:
 (a) the amino acid sequence of SEQ ID NO: 1;
 (b) a variant thereof having at least 50% identity to the amino acid sequence of SEQ ID NO: 1 and having IgG endoglycosidase activity; or
 (c) a fragment of either thereof having IgG endoglycosidase activity.

Preferably, the polypeptide comprises, or consists of, the sequence of SEQ ID NO: 1. SEQ ID NO: 1 is the sequence of the mature form of EndoS, without the signal sequence, and corresponds to amino acids 37 to 995 of SEQ ID NO: 2.

The polypeptide may additionally include a signal sequence. Accordingly, the EndoS polypeptide may comprise:
 (a) the amino acid sequence of SEQ ID NO: 2;
 (b) a variant thereof having at least 50% identity to the amino acid sequence of SEQ ID NO: 2 and having IgG endoglycosidase activity; or
 (c) a fragment of either thereof having IgG endoglycosidase activity.

The EndoS polypeptide may consist of the sequence shown in SEQ ID NO: 2.

Variant polypeptides are those for which the amino acid sequence varies from that in SEQ ID NO: 1 or SEQ ID NO: 2, but which retain the same essential character or basic functionality as EndoS. The variant polypeptides may therefore display IgG endoglycosidase activity. Typically, polypeptides with more than about 50%, 55% or 65% identity, preferably at least 70%, at least 80%, at least 90% and particularly preferably at least 95%, at least 97% or at least 99% identity, with the amino acid sequence of SEQ ID NO: 1 or SEQ ID NO: 2 are considered variants of the protein. Such variants may include allelic variants and the deletion, modification or addition of single amino acids or groups of amino acids within the protein sequence, as long as the peptide maintains the basic functionality of EndoS. The identity of variants of SEQ ID NO: 1 or SEQ ID NO: 2 may be measured over a region of at least 100, at least 250, at least 500, at least 750, at least 800, at least 850, at least 900, at least 950, at least 955 or more contiguous amino acids of the sequence shown in SEQ ID NO: 1 or SEQ ID NO: 2, or more preferably over the full length of SEQ ID NO: 1 or SEQ ID NO: 2.

Amino acid identity may be calculated using any suitable algorithm. For example the UWGCG Package provides the BESTFIT program which can be used to calculate homology (for example used on its default settings) (Devereux et al (1984) *Nucleic Acids Research* 12, 387-395). The PILEUP and BLAST algorithms can be used to calculate homology or line up sequences (such as identifying equivalent or corresponding sequences (typically on their default settings), for example as described in Altschul S. F. (1993) *J Mol Evol* 36:290-300; Altschul, S, F et al (1990) *J Mol Biol* 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The variant sequences typically differ by at least 1, 2, 3, 5, 10, 20, 30, 50, 100 or more mutations (which may be substitutions, deletions or insertions of amino acids). For example, from 1 to 100, 2 to 50, 3 to 30 or 5 to 20 amino acid substitutions, deletions or insertions may be made. The modified polypeptide generally retains activity as an IgG-specific endoglycosidase. The substitutions are preferably conservative substitutions, for example according to the following Table. Amino acids in the same block in the second column and preferably in the same line in the third column may be substituted for each other:

| ALIPHATIC | Non-polar | G, A, P |
| | | I, L, V |
| | Polar - uncharged | C, S, T, M |
| | | N, Q |
| | Polar - charged | D, E |
| | | K, R |
| AROMATIC | | H, F, W, Y |

Variants of the amino acid sequence of SEQ ID NO: 1 preferably contain residues 191 to 199 of SEQ ID NO: 1, i.e., Leu-191, Asp-192, Gly-193, Leu-194, Asp-195, Val-196, Asp-197, Val-198 and Glu-199 (SEQ ID NO:24) of SEQ ID NO: 1 (which correspond to residues 227 to 235 of SEQ ID NO: 2, i.e., Leu-227, Asp-228, Gly-229, Leu-230, Asp-231, Val-232, Asp-233, Val-234 and Glu-235 (SEQ ID NO:24) of SEQ ID NO: 2). These amino acids constitute a perfect chitinase family 18 active site, ending with glutamic acid. The glutamic acid in the active site of chitinases is essential for enzymatic activity. Most preferably, therefore, the variant of SEQ ID NO: 1 contains Glu-199 of SEQ ID NO: 1 and the variant of SEQ ID NO: 2 contains Glu-235 of SEQ ID NO: 2. The variant of SEQ ID NO: 1 may contain residues 191 to 199 of SEQ ID NO: 1 having one or more conservative substitutions, provided that the variant contains Glu-199 of SEQ ID NO: 1. Alternatively, the variant of SEQ ID NO: 2 may contain residues 227 to 235 of SEQ ID NO: 2 having one or more conservative substitutions, provided that the variant contains Glu-235 of SEQ ID NO: 2.

The fragment of the EndoS polypeptide used in the invention is typically at least 10, for example at least 20, 30, 40, 50 or more amino acids in length, up to 100, 200, 250, 300, 500, 750, 800, 850, 900, 950 or 955 amino acids in length, as long as it retains the IgG endoglycosidase activity of EndoS. Preferably, the fragment of the EndoS polypeptide used in the invention encompasses residues 191 to 199 of SEQ ID NO: 1, i.e., Leu-191, Asp-192, Gly-193, Leu-194, Asp-195, Val-196, Asp-197, Val-198 and Glu-199 (SEQ ID NO:24) of SEQ ID NO: 1 (residues 227 to 235 of SEQ ID NO: 2, i.e., Leu-227, Asp-228, Gly-229, Leu-230, Asp-231, Val-232, Asp-233, Val-234 and Glu-235 (SEQ ID NO:24) of SEQ ID NO: 2). A preferred fragment of SEQ ID NO: 2 consists of amino acids 37 to 995 of SEQ ID NO: 2, i.e., SEQ ID NO: 1, which corresponds to the form of EndoS secreted from *S. pyogenes* after removal of the signal peptide. Another preferred fragment of the invention consists of amino acids 1 to 409 of SEQ ID NO: 1 (amino acids 37 to 445 of SEQ ID NO: 2), which corresponds to the enzymatically active α-domain of EndoS generated by cleavage by the streptococcal cysteine proteinase SpeB.

The polypeptides used in the invention may be chemically modified, e.g. post-translationally modified. For example, they may be glycosylated, phosphorylated or comprise modified amino acid residues. They may be modified by the addition of histidine residues to assist their purification or by the addition of a signal sequence to promote insertion into the cell membrane. Such modified polypeptides fall within the scope of the term "polypeptide" used herein.

Typically, polypeptides for use in accordance with the invention display immunoglobulin endoglycosidase activity, and in particular IgG endoglycosidase activity. Preferably, the polypeptide hydrolyzes the β-1,4-di-N-acetylchitobiose core of the asparagine-linked glycan of IgG. Preferably the activity is specific for IgG. The endoglycosidase activity may be determined by means of a suitable assay. For example, a test polypeptide may be incubated with IgG at a suitable temperature, such as 37° C. The starting materials and the reaction products may then be analysed by SDS PAGE. Typically, the molecular mass of the IgG heavy chain is reduced by approximately 3 kDa if the test polypeptide has IgG endoglycosidase activity. Another assay for determining whether a test polypeptide has IgG endoglycosidase activity is by detection of glycosylated IgG using *Lens culinaris* agglutinin lectin (LCA), optionally using horseradish peroxidase and peroxidase substrate. Typically, the carbohydrate signal is reduced if the test polypeptide has IgG endoglycosidase activity. Another assay for determining whether a test polypeptide has IgG endoglycosidase activity is by incubation of a test polypeptide with purified IgG Fc fragments followed by reduction of the sample with 10 mM dithiothreitol and mass spectroscopy (MALDI-TOF) analysis. Typically, the mass of monomeric IgG Fc is reduced by 1417±14 Da if the test polypeptide has IgG endoglycosidase activity.

The endoglycosidase activity of the polypeptides can be further characterised by inhibition studies.

The endoglycosidase activity of the polypeptide is generally IgG-specific in that the polypeptide may not degrade the other classes of Ig, namely IgM, IgA, IgD and IgE, when incubated with these immunoglobulins under conditions that permit cleavage of IgG. The EndoS polypeptide is capable of hydrolyzing IgG molecules present in the subject to be treated. Thus, where the subject is a human, the EndoS polypeptide is capable of hydrolyzing human IgG. EndoS is capable of hydrolyzing human IgG of all four subclasses ($IgG_{1-4}$). In preferred embodiments, the EndoS polypeptide has the ability to hydrolyze human, Rhesus monkey, mouse, rat, rabbit, horse, goat, dog and swine IgG.

Polypeptides for use in the invention may be in a substantially isolated form. It will be understood that the polypeptide may be mixed with carriers or diluents which will not interfere with the intended purpose of the polypeptide and still be regarded as substantially isolated. A polypeptide for use in the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

Polypeptides for use in the present invention may be isolated from any suitable organism that expresses an EndoS polypeptide or a variant of an EndoS polypeptide. Typically, the EndoS polypeptide is isolated from suitable EndoS expressing strains of *Streptococcus*, preferably strains of *S. pyogenes*. Suitable organisms and strains may be identified by a number of techniques. For example, *S. pyogenes* strains may initially be tested for the presence an ndoS gene. Polynucleotide primers or probes may be designed based on, for example, SEQ ID NOs: 1, 2 or 3. The presence of the ndoS gene can then be verified by PCR using such primers or by hybridisation of probes to genomic DNA of the *S. pyogenes* strain.

Streptococcal strains expressing active EndoS or a variant thereof can be identified by assaying for IgG endoglycosidase activity in the culture supernatant or by immunodetection using antibodies directed towards EndoS. The Streptococcal strains that have been verified as expressing active EndoS are the *S. pyogenes* M1 serotype strains AP1 and SF370, the *S. equi* strain 4047 and the *S. zooepidermicus* strain H70. In addition, the ndoS gene is found in the following *S. pyogenes* strains: M1 serotype strains SSI-1 and MGAS5005, M2 serotype strain MGAS10270, M3 serotype strain MGAS315, M4 serotype strain MGAS10750, M5 serotype strain Manfredo, M6 serotype strain MGAS10394, M12 serotype strain MGAS9429, M18 serotype strain MGAS8232, M28 serotype strain MGAS6180 and M49 serotype strain 591.

Isolation and purification of EndoS from an expressing *S. pyogenes* culture, or from cultures of other cells expressing EndoS is typically on the basis of IgG endoglycosidase activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted polypeptides may then be subjected to ion exchange chromatography, for example by FPLC on a Mono Q column. Eluted fractions may be assayed for IgG endoglycosidase activity and peak activity fractions may be pooled. Fractions may be analysed by SDS PAGE. Fractions may be stored at −80° C. In an alternative method to purify EndoS, EndoS without the signal sequence (i.e., having the sequence of SEQ ID NO: 1) is expressed in *Escherichia coli* using GST Gene Fusion System (Amersham-Pharmacia Biotech, Uppsala, Sweden). A 2929 base pair PCR product covering bases 304 to 3232 of the ndoS sequence is amplified from *S. pyogenes* genomic DNA using primers 5'-ACT-G<u>GG-ATC</u>-CCG-GAG-GAG-AAG-ACT-3' (SEQ ID NO:26) with a BamHI site (underlined) and 5'-TTA-AT<u>C-TCG-AGG</u>-TTG-CTA-TCT-AAG-3' (SEQ ID NO:27) with an XhoI site (underlined). This fragment is digested with BamHI and XhoI and ligated into the pGEX-5X-3 generating plasmid pGEXndoS that is used to transform *E. coli* BL21 (DE3)pLys. pGEXndoS/BL21(DE3)pLys is induced with 0.1 mM isopropyl β-D-thiogalactopyranoside. After induction, bacteria are lysed using BugBuster™ (Novagen) and the GST-EndoS fusion protein is purified on Glutathione-Sepharose®. The GST tag is removed using factor Xa according to protocols (Amersham-Pharmacia Biotech), and residual factor Xa is removed using Xarrest™-agarose (Novagen). This results in a preparation of recombinant EndoS (rEndoS) that is homogenous as assessed by SDS-PAGE and Western blot using EndoS-specific antibodies. Prior to in vivo experiments protein samples are sterile-filtered through a 0.2 µm filter (Millipore). Purified EndoS protein is stored at −80° C. in phosphate buffered saline.

Polypeptides for use in the invention may also be prepared as fragments of such isolated polypeptides. Further, the EndoS polypeptides may also be made synthetically or by recombinant means. For example, a recombinant EndoS polypeptide may be produced by transfecting mammalian cells in culture with an expression vector comprising a nucleotide sequence encoding the polypeptide operably linked to suitable control sequences, culturing the cells, extracting and purifying the EndoS polypeptide produced by the cells.

The amino acid sequence of polypeptides for use in the invention may be modified to include non-naturally occurring amino acids or to increase the stability of the compound. When the polypeptides are produced by synthetic means, such amino acids may be introduced during production. The polypeptides may also be modified following either synthetic or recombinant production.

Polypeptides for use in the invention may also be produced using D-amino acids. In such cases the amino acids will be linked in reverse sequence in the C to N orientation. This is conventional in the art for producing such polypeptides.

A number of side chain modifications are known in the art and may be made to the side chains of the EndoS polypeptides, provided that the polypeptides retain IgG endoglycosidase activity.

Polynucleotides

A polynucleotide encoding an EndoS polypeptide or variant may be used to treat or prevent a disease or condition mediated by pathogenic IgG antibodies. In particular the polynucleotide may comprise or consist of: (a) the coding sequence of SEQ ID NO: 3; (b) a sequence which is degenerate as a result of the genetic code to the sequence as defined in (a); (c) a sequence having at least 60% identity to a sequence as defined in (a) or (b) and which encodes a polypeptide having IgG endoglycosidase activity; or (d) a fragment of any one of the sequences as defined in (a), (b) or (c) which encodes a polypeptide having IgG endoglycosidase activity.

Typically the polynucleotide is DNA. However, the polynucleotide may be a RNA polynucleotide. The polynucleotide may be single or double stranded, and may include within it synthetic or modified nucleotides.

A polynucleotide of the invention can typically hybridize to the coding sequence or the complement of the coding sequence of SEQ ID NO: 3 at a level significantly above background. Background hybridization may occur, for example, because of other DNAs present in a DNA library. The signal level generated by the interaction between a polynucleotide of the invention and the coding sequence or complement of the coding sequence of SEQ ID NO: 3 is typically at least 10 fold, preferably at least 100 fold, as intense as interactions between other polynucleotides and the coding sequence of SEQ ID NO: 3. The intensity of interaction may be measured, for example, by radiolabelling the probe, e.g. with $^{32}P$. Selective hybridisation may typically be achieved using conditions of medium to high stringency. However, such hybridisation may be carried out under any suitable conditions known in the art (see Sambrook et al, Molecular Cloning: A Laboratory Manual, 1989). For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 3 may be modified by nucleotide substitutions, for example from 1, 2 or 3 to 10, 25, 50, 100, 200, 500 or 750 substitutions. The polynucleotide of SEQ ID NO: 3 may alternatively or additionally be modified by one or more insertions and/or deletions and/or by an extension at either or both ends. Additional sequences such as signal sequences may also be included. The modified polynucleotide generally encodes a polypeptide which has IgG specific endoglycosidase activity. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 3 will generally have at least 60%, at least 70%, at least 80%, at least 90%, at least 95%, at least 98% or at least 99% sequence identity to the coding sequence of SEQ ID NO: 3 over a region of at least 20, preferably at least 30, for instance at least 40, at least 60, at least 100, at least 200, at least 500, more preferably at least 750 contiguous nucleotides or most preferably over the full length of SEQ ID NO: 3 or the length of SEQ ID NO: 3 encoding a polypeptide having the sequence shown in SEQ ID NO: 1 or 2. Sequence identity may be determined by any suitable method, for example as described above.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 60, preferably over 100 nucleotides forms one aspect of the invention, as does a polynucleotide which has at least 95% sequence identity over 500 nucleotides.

Polynucleotide fragments will preferably be at least 20, for example at least 25, at least 30 or at least 50 nucleotides in length. They will typically be up to 100, 150, 250 or 500 nucleotides in length. Fragments can be longer than 500 nucleotides in length, for example up to 600, 700, 800, 900, 1000, 1500, 2000, 2500 or 3000 nucleotides in length, or even up to a few nucleotides, such as five, ten or fifteen nucleotides, short of the coding sequence of SEQ ID NO: 3.

Polynucleotides for use in the invention may be produced recombinantly, synthetically, or by any means available to those of skill in the art. They may also be cloned by standard techniques. The polynucleotides are typically provided in isolated and/or purified form.

In general, short polynucleotides will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the ndoS gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the ndoS gene sequence described herein. Although in general the techniques mentioned herein are well known in the art, reference may be made in particular to Sambrook et al. (1989).

EndoS polynucleotides as described herein have utility in production of the polypeptides for use in the present invention, which may take place in vitro, in vivo or ex vivo. The polynucleotides may be used as therapeutic agents in their own right or may be involved in recombinant protein synthesis.

The polynucleotides for use in the invention are typically incorporated into a recombinant replicable vector. The vector may be used to replicate the nucleic acid in a compatible host cell. Therefore, polynucleotides for use in the invention may be made by introducing an EndoS polynucleotide into a replicable vector, introducing the vector into a compatible host cell and growing the host cell under conditions which bring about replication of the vector. The host cell may, for example, be an *E. coli* cell.

Preferably the vector is an expression vector comprising a nucleic acid sequence that encodes an EndoS polypeptide. Such expression vectors are routinely constructed in the art of molecular biology and may for example involve the use of plasmid DNA and appropriate initiators, promoters, enhancers and other elements, such as for example polyadenylation signals, which may be necessary and which are positioned in the correct orientation in order to allow for protein expression. Other suitable vectors would be apparent to persons skilled in the art. By way of further example in this regard we refer to Sambrook et al. (1989).

Preferably, a polynucleotide for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vector is typically adapted to be used in vivo.

Promoters and other expression regulation signals may be selected to be compatible with the host cell for which expression is designed. Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences. This will allow the introduction of the polynucleotides of the invention into the genome of eukaryotic cells by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Diseases and Conditions

The EndoS polypeptide, or polynucleotide, may be used to treat or prevent diseases or conditions mediated by pathogenic IgG antibodies. It is well known in the art that IgG antibodies are involved in the pathogenesis of a number of different diseases and conditions. The present inventors have found that the role of pathogenic IgG antibodies in such diseases can be inhibited using an EndoS polypeptide or polynucleotide.

The disease or condition can be an autoimmune disease. Such diseases include Addison's disease, alopecia greata, ankylosing spondilitis, antiphospholipid syndrome, aplastic anaemia, autoimmune gastritis, autoimmune hearing loss, autoimmune haemolytic anaemias, autoimmune hepatitis, autoimmune hypoparathyroidism, autoimmune hypophysitis, autoimmune inner ear disease, autoimmune lymphoproliferative syndrome, autoimmune myocarditis, autoimmune oophoritis, autoimmune orchitis, autoimmune polyendocrinopathy, Beçhet's disease, bullous pemphigoid, cardiomyopathy, chronic inflammatory demyelinating polyneuropathy, Churg-Strauss syndrome, coeliac disease, Crohn's disease, CREST syndrome, Degas disease, epidermolysis bullosa acquisita, essential mixed cryoglobulinaemia, giant cells arteritis, glomerulonephritis, Goodpasture's syndrome, Graves' disease, Guillan-Barre syndrome, Hashimoto's thyroiditis, idiopathic thrombocytopenic purpura, inflammatory bowel disease, Kawasaki's disease, Meniere's syndrome, mixed connective tissue disease, Mooren's ulcer, multiple sclerosis, myasthenia gravis, pemphigus foliaceous, pemphigus vulgaris, pernicious anaemia, polyarteritis nodosa, polyglandular autoimmune syndrome type 1 (PAS-1), polyglandular autoimmune syndrome type 2 (PAS-2), polyglandular autoimmune syndrome type 3 (PAS-3), polymyositis/dermatomyositis, primary biliary cirrhosis, psoriasis, psoriatic arthritis, Raynaud's syndrome, Reiter's syndrome, rheumatoid arthritis, sarcoidosis, scleroderma, Sjögren's syndrome, subacute thyroiditis, sympathetic opthalmia, systemic lupus erythematosus, Takayasu's arteritis, type 1 diabetes mellitus, vitiligo, Vogt-Koyanagi-Harada disease or Wegener's granulomatosis. Preferably the autoimmune disease is rheumatoid arthritis (RA), systemic lupus erythematosus or idiopathic thrombocytopenic purpura.

The disease or condition can be asthma. The asthma can be acute or chronic asthma.

IgG activates the classical pathway of the complement system. EndoS polypeptides and polynucleotides can therefore be used to treat diseases and conditions where complement activation is detrimental to the patient. For example, the EndoS polypeptides and polynucleotides can be used to treat transplantation-derived disorders, for example transplant rejection (such as acute or chronic allograft or xenograft rejection) and graft-versus-host disease. The transplantation-derived disorder may occur due to the transplantation of a tissue or an organ in a patient.

EndoS polypeptides and polynucleotides are also of use in post-operative treatment, for example in the treatment of patients who have undergone heart by-pass operations.

Further, EndoS polypeptides and polynucleotides can be used for the treatment of acquired haemophilia, i.e to remove IgG in haemophilia patients who have developed autoantibodies against coagulation factors.

The subject is typically a mammalian subject, such as a mouse, rat or primate (e.g. a marmoset or monkey). The subject may be human or a non-human animal. Where the subject is a laboratory animal such as a mouse, rat or primate, the animal may be treated to induce a disease or condition mediated by pathogenic IgG antibodies. For example, the mouse anti-CII antibody induced arthritis (CAIA) model described by Nandakumar et al. (Am. J. Pathol. 163(5): 1827-1837, 2003), or a modified version of that model, may be used.

Therapy and Prophylaxis

The present invention provides the use of EndoS polypeptides and polynucleotides to treat or prevent a disease or condition mediated by pathogenic IgG antibodies. Treatment may be therapeutic or prophylactic.

The EndoS polypeptide or polynucleotide may be administered to an individual in order to prevent the onset of one or more symptoms of the disease or condition. In this embodiment, the subject may be asymptomatic. The subject may have a genetic predisposition to the disease. A prophylactically effective amount of the polypeptide or polynucleotide is administered to such an individual. A prophylactically effective amount is an amount which prevents the onset of one or more symptoms of a disease or condition.

A therapeutically effective amount of the EndoS polypeptide or polynucleotide is an amount effective to ameliorate one or more symptoms of a disease or condition. Preferably, the individual to be treated is human.

The EndoS polypeptide or polynucleotide may be administered to the subject by any suitable means. The polypeptide or polynucleotide may be administered by enteral or parenteral routes such as via oral, buccal, anal, pulmonary, intravenous, intra-arterial, intramuscular, intraperitoneal, intraarticular, topical or other appropriate administration routes.

The EndoS polypeptide or polynucleotide may be administered to the subject in such a way as to target therapy to a particular site. For example, an EndoS polypeptide may be administered directly to the site of a transplanted organ. The EndoS polypeptide may be injected locally, for example intraarticularly or in one or more joints. Local administration of EndoS to the joints is particularly preferable for the prophylaxis or treatment of rheumatoid arthritis (RA). The EndoS polypeptide may be conjugated with reagents that bind cartilage specifically. For EndoS polynucleotides, expression vectors encoding the EndoS polypeptide may be used to direct expression of EndoS to a particular tissue, for example by using tissue-specific promoters or RNAi.

The formulation of any of the polypeptides and polynucleotides mentioned herein will depend upon factors such as the nature of the polypeptide or polynucleotide and the condition to be treated. The polypeptide or polynucleotide may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The polypeptide or polynucleotide may also be administered as suppositories. A physician will be able to determine the required route of administration for each particular patient.

Typically the polypeptide or polynucleotide is formulated for use with a pharmaceutically acceptable carrier or diluent and this may be carried out using routine methods in the pharmaceutical art. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

For suppositories, traditional binders and carriers may include, for example, polyalkylene glycols or triglycerides; such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Pharmaceutical compositions suitable for delivery by needleless injection, for example, transdermally, may also be used.

A therapeutically effective amount of polypeptide or polynucleotide is administered. The dose may be determined according to various parameters, especially according to the polypeptide or polynucleotide used; the age, weight and condition of the patient to be treated; the route of administration; and the required regimen. Again, a physician will be able to determine the required route of administration and dosage for any particular patient. A typical daily dose is from about 0.1 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The EndoS nucleotide sequences described above and expression vectors containing such sequences can also be used as pharmaceutical formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 µg nucleic acid for particle mediated gene delivery and 10 µg to 1 mg for other routes.

The present invention also provides a method of treating, ex vivo, blood taken from a patient suffering from a disease or condition mediated by pathogenic IgG antibodies comprising contacting the blood with an EndoS polypeptide. EndoS may thus be used for extracorporeal treatment of blood. The EndoS may be used to treat one or more components of blood, such as plasma or serum. The ex vivo method described herein may be practised on blood that has already been removed from the body of a patient. The blood or blood product may optionally be returned to the patient after being contacted with an EndoS polypeptide.

The following Examples illustrate the invention:

Example 1

EndoS Efficiently Hydrolyzes IgG in Human Blood

In order to be efficient as a therapeutic agent against pathological IgG, EndoS needs to be active at low concentrations in a human whole blood environment. To investigate this, recombinant EndoS (rEndoS) without the signal sequence (i.e. having the sequence of SEQ ID NO: 1) was produced and purified as previously described (Collin & Olsén, 2001, Infect. Immun. 69: 7187-7189). Increasing final concentrations (0, 0.31, 0.63, 1.25, 2.5, 5, 10, and 20 µg/ml) of rEndoS were incubated in 500 µl of heparinized human blood from healthy volunteers with rotation end over end for 1 hour at 37° C. Samples were centrifuged at 720×g for 10 min at 4° C. followed by purification of IgG in plasma using protein G Sepharose according to manufacturer's instructions (GE Healthcare Biosciences, Uppsala, Sweden). There was no difference in binding efficiency to protein G between fully glycosylated IgG and EndoS treated IgG, which is in concordance with previous findings for the IgG binding proteins protein H (from *S. pyogenes*) and protein A (from *Staphylococcus aureus*) (Collin & Olsén 2001, EMBO J. 20: 3046-3055). Purified IgG was separated on 10% SDS-PAGE, stained with Coomassie or electroblotted onto PVDF (Immobilon-P, Millipore, Bedford, Mass.). Glycosylated IgG was detected using 5 µg/ml of biotinylated *Lens culinaris* agglutinin lectin (LCA) and 1 µg/ml of Streptavidin-Horseradish peroxidase (Vector Laboratories, Burlingame, Calif.) and SuperSignal West Pico peroxidase substrate (Pierce, Rockford, Ill.). Membranes were analyzed using a Chemidoc XRS imaging system and Quantity One image analysis software (Bio-Rad, Hercules, Calif.).

Figure 5:
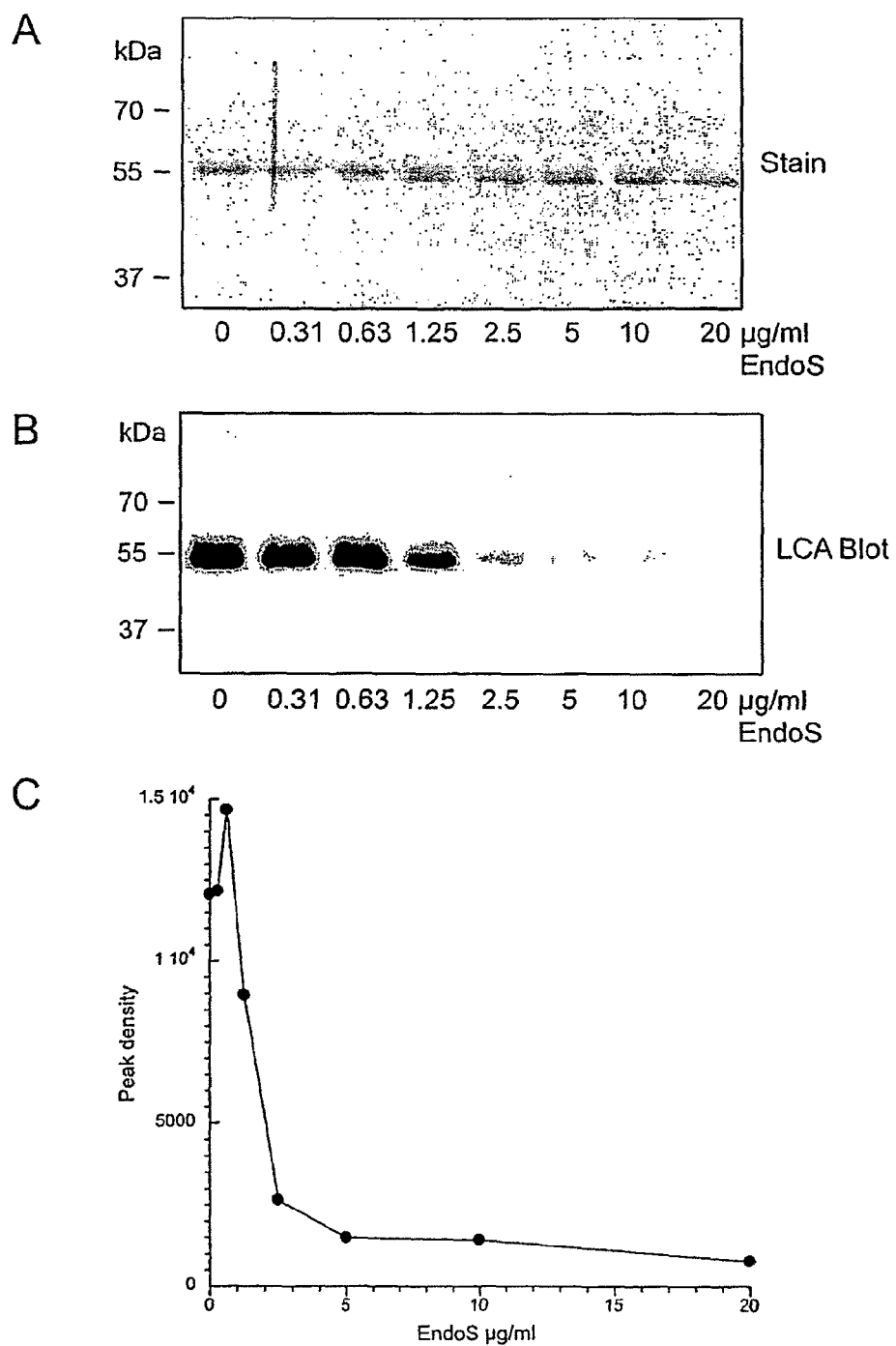
FIG. 5 shows an analysis of EndoS activity in human blood.

These experiments showed that increasing concentrations of EndoS gradually shift the IgG heavy chain to an approximately 3 kDa smaller apparent molecular mass and that almost no full size heavy chain could be seen above a concentration of 2.5-5 µg/ml of rEndoS (FIG. 5A). The LCA lectin blot experiments on the same samples showed that increasing concentration of rEndoS gradually gives a lower carbohydrate signal and that there is virtually no signal above rEndoS concentrations of 2.5-5 µg/ml (FIG. 5B). It has previously been shown that lack of lectin signals corresponds well with complete IgG glycan hydrolysis as analyzed by mass spectroscopy (Collin & Fischetti, 2004, J. Biol. Chem. 279: 22558-22570). Furthermore, peak density analysis shows a dose-response curve which flattens out at background levels around an rEndoS concentration of 5 µg/ml (FIG. 5C).

These results indicate that 5 µg/ml of rEndoS in 1 hour completely hydrolyzes the IgG pool in human blood. Assuming an IgG plasma concentration of 10 mg/ml this would mean complete hydrolysis of IgG in 1 hour at an rEndoS to IgG ratio of 1:2000. Thus, rEndoS shows a remarkably efficient hydrolysis of the functionally important IgG glycan in such a complex environment as human blood.

Example 2

EndoS Efficiently Hydrolyzes IgG in Rabbits

In order to further substantiate the use of EndoS as a therapeutic agent, the IgG glycan hydrolyzing activity of EndoS in the circulation of live animals was investigated. Swedish loop rabbits with a body weight of approximately 3 kg were injected intravenously with 1 mg of rEndoS, corresponding to an approximate rEndoS to IgG ratio of 1:2000 given that rEndoS distributes in blood only. Animals showed no signs of disease. Serum samples were withdrawn at 0, 1, 2, 4, 6, 8 and 12 hours, and 1, 2, 3, 4, 5, 6, 8, and 10 days. Serum IgG was analyzed for glycosylation status using SDS-PAGE and lectin blot analysis as described above for human blood.

Figure 6:
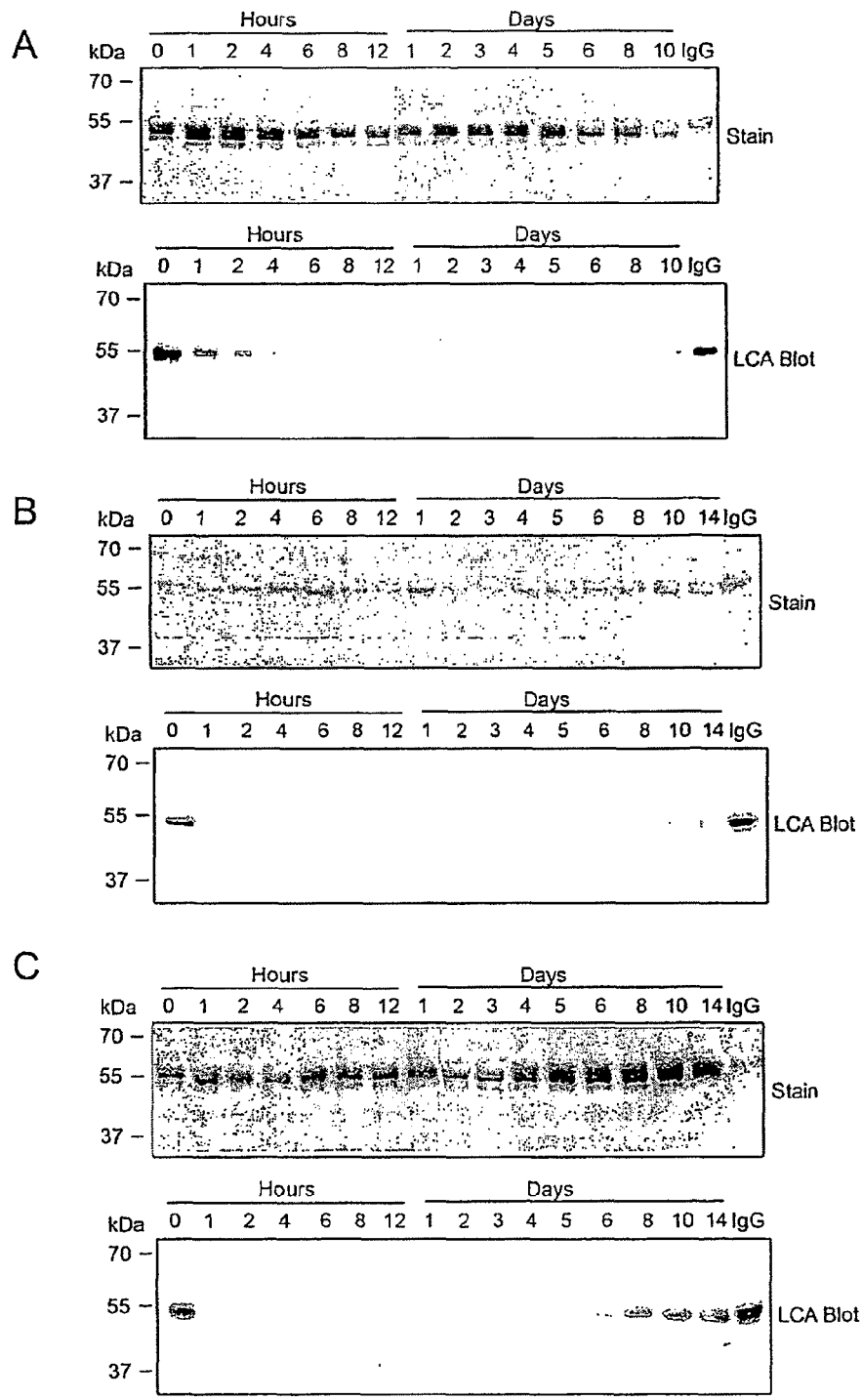
FIG. 6 shows an analysis of in vivo activity of EndoS in rabbit.

These experiments showed that before injection, the apparent molecular mass of the heavy chains of IgG was comparable to fully glycosylated intact rabbit IgG (FIG. 6A, Stain, Hour 0, and IgG). In contrast, 1 hour after rEndoS injection there was already a partial shift of the IgG heavy chains towards an approximately 3 kDa smaller protein band. Four hours after rEndoS injection IgG heavy chains were completely shifted to the lower apparent molecular mass form and this was sustained until the last sample at day 10 after injection (FIG. 6A, Stain, Hour 4 to Day 10). Lectin blot analysis of the same samples revealed that the IgG heavy chain carbohydrate signal was nearly abolished 6-8 hours after rEndoS injection and this was sustained until day 10 where there was only a slight increase in lectin signal (FIG. 6A, LCA Blot).

In order to see if rEndoS was active within an animal that had already been exposed to the enzyme, a second injection with 1 mg of rEndoS was performed 35 days after the first injection. Again, animals seemed unaffected by the injection and serum samples were withdrawn and analyzed as above. SDS-PAGE revealed that before the second injection, IgG heavy chain migrated as fully glycosylated control rabbit IgG heavy chain (FIG. 6B, Hour 0, IgG). After 1 hour the IgG heavy chain was partially shifted towards a 3 kDa lower apparent molecular mass, and after 6-8 hours the IgG heavy chain was completely shifted and this shift was sustained until day 10-14 following this second administration (FIG. 6B, Stain, Hour 1 to Day 14). Lectin blot analysis revealed that the IgG heavy chain carbohydrate signal was nearly abolished 1-2 days after rEndoS injection and this was sustained until day 8 where there was a slight increase in lectin signal with a further slight increase between day 10 and 14 (FIG. 6B, LCA Blot, Day 1-14).

In order to investigate if rEndoS still had activity within an animal that had been exposed intravenously twice to rEndoS, a third injection with 1 mg of rEndoS was performed 130 days after the first injection. Again, animals were unaffected by the injection and serum samples were withdrawn and analyzed as above. SDS-PAGE revealed that prior to the third injection, IgG heavy chain migrated as fully glycosylated control rabbit IgG heavy chain (FIG. 6C, Hour 0, IgG). After 1 hour the IgG heavy chain was partially shifted towards a 3 kDa lower molecular mass, and this shift was sustained until day 8-10 following this third administration (FIG. 6C, Stain, Hour 1 to Day 14). Lectin blot analysis revealed that the IgG heavy chain carbohydrate signal was abolished one hour after the third rEndoS injection and this was sustained until day 5 where there was a slight increase in lectin signal with a further increase between day 6 and 14 (FIG. 6C, LCA Blot, Day 1-14).

Taken together, these results indicate that low concentrations of EndoS efficiently hydrolyze the heavy chain glycan on the whole rabbit IgG pool in vivo. Furthermore, previous intravenous exposure to EndoS does not significantly affect the in vivo enzymatic activity of EndoS.

Example 3

EndoS is Active in Rabbits Despite Antibodies Directed Towards the Enzyme

Since EndoS had full activity when injected a second and a third time, it was of interest to determine whether this was due to no or low immune response against the enzyme, or if there were specific antibodies against EndoS that did not interfere with enzymatic activity. This was of particular interest since it is known that both healthy individuals and those infected with S. pyogenes have antibodies against EndoS (Åkesson et al, 2004, J. Infect. Dis. 189: 797-804).

In order to investigate this, purified rEndoS was separated on 10% SDS-PAGE and electroblotted onto PVDF that was cut into 1.5 mm strips. Strips were incubated with 1:500 dilutions of all the serum samples from the first, second and third injections, followed by incubation with peroxidase-labeled goat anti-rabbit antibodies (Pierce). Strips were developed using chemiluminescence as described above for lectin blots.

Figure 7:
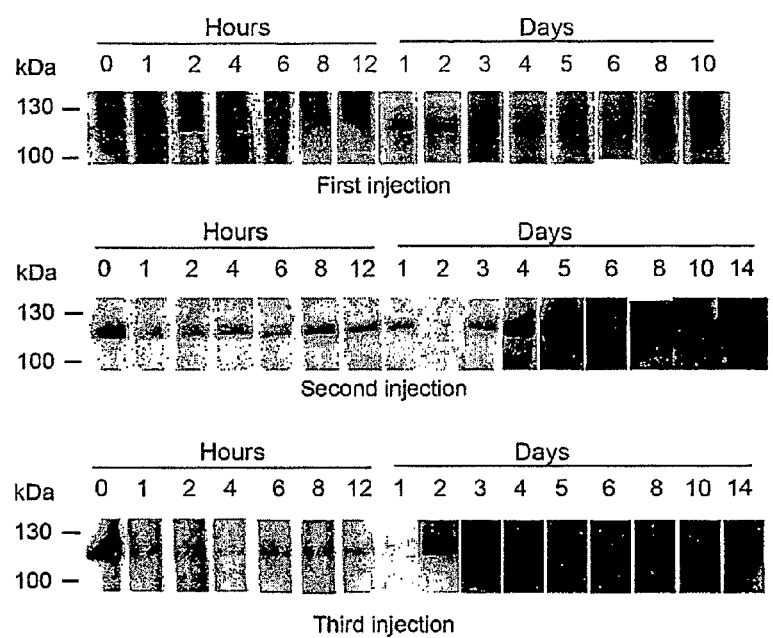
FIG. 7 shows the rabbit antibody response to rEndoS. Serum samples were withdrawn from the rabbit at indicated time point after the first, second and third injections of rEndoS. The sera were used as primary antisera in a Western blot on separate membrane strips with SDS-PAGE separated purified rEndoS.

This experiment revealed that before the first injection there were already antibodies reacting with rEndoS (FIG. 7, First injection, Hour 0). There was only a slight increase in reactivity towards rEndoS 10 days after injection (FIG. 7, First injection and FIG. 7A insert), but there was a gap in the reactivity between 6 and 8 hours after injection (FIG. 7, First injection). One possible reason for this finding is that specific antibodies binding to rEndoS are complexed and removed from circulation by the reticulo-endothelial system. Just prior to the second injection of rEndoS the reactivity against rEndoS was comparable or slightly higher than before the first injection, and the reactivity did not increase during the first 3 days after injection (FIG. 7, Second injection, Hour 0-Day 3). From day 4 to 14 after the second injection, the reactivity against rEndoS gradually increased (FIG. 7, Second injection, Day 4-14). Before the third injection of rEndoS, the reactivity against rEndoS was slightly higher than before the second injection, and the reactivity did not increase during the first day after injection (FIG. 7, Third injection, Hour 0-Day 1). From day 2 to 14 after the third injection, the reactivity against rEndoS increased (FIG. 7, Third injection, Day 2-14) although the high signal levels made determination of the level of increase difficult.

Given the very high signal levels in the Western blots from samples obtained after the second and third injections, samples prior to and after all three injections were also analyzed by ELISA. For ELISA experiments, 2 μg of EndoS was used to coat microtiter plates (Nunc, Roskilde, Denmark), followed by blocking with 20 mg/ml of bovine serum albumin in PBS. Sera from animals before EndoS injections and 0.5, 1, 5, and 10 days after injections were used as primary antiserum in serial dilutions of 1:100 to 1:200,000. Peroxidase-labeled goat anti-rabbit antibodies (Pierce) were used as secondary antibodies and ABTS (Roche, Ind.) as peroxidase substrate. A standard curve for rabbit IgG was generated by coating microtiter plates as above with serial dilutions of polyclonal rabbit IgG (Sigma) and peroxidase-labeled goat anti-rabbit antibodies as secondary antibodies. Plates were analyzed at 405 nm in a Victor3 multi label reader (Perkin-Elmer, Waltham, Miss.).

Figure 7A:
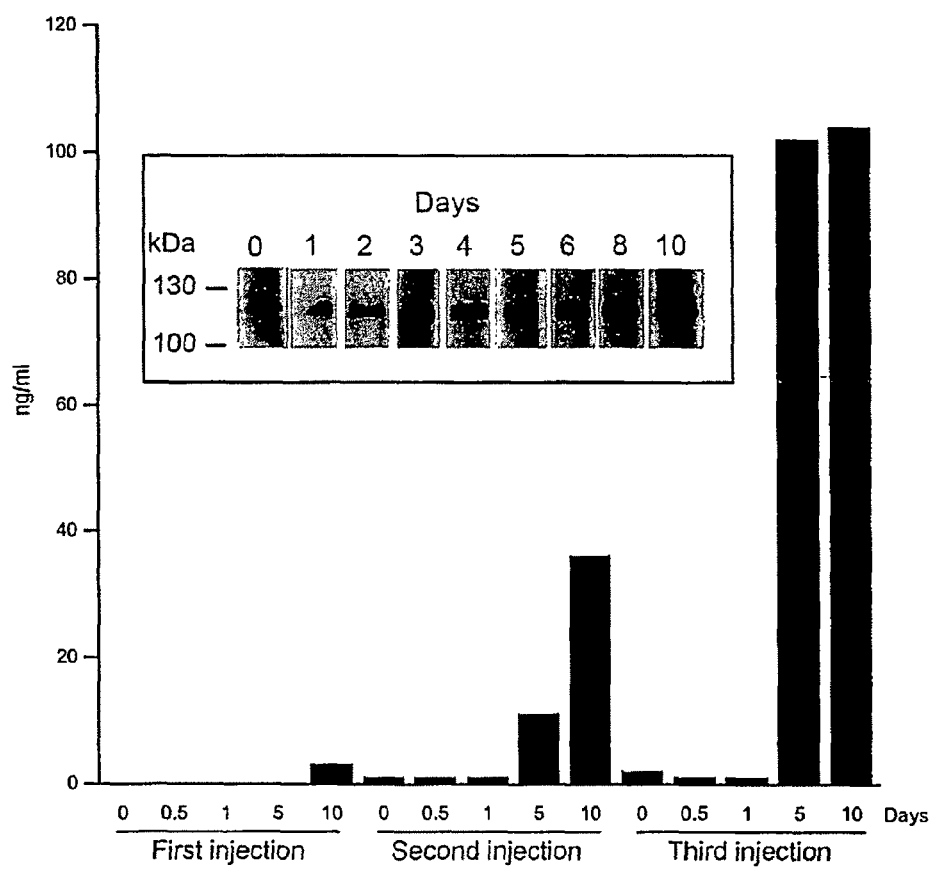
FIG. 7A also shows the rabbit antibody response to rEndoS. Serum samples are the same as for FIG. 7. Insert: Western blot as in FIG. 7 using the serum samples after the first injection as primary antisera. Main figure: Serum samples following the first, second, and third injections were used as primary antisera in an ELISA experiment with immobilized EndoS. Increase in concentration (ng/ml) of anti-EndoS IgG compared to concentration before first injection is presented. One representative experiment is shown.

The ELISA experiments confirmed that just prior to the second injection of EndoS, the reactivity against EndoS was comparable or slightly higher than before the first injection, and the reactivity still had not increased at 5 days after injection (FIG. 7A, First and second injection). From day 5 to 10 after the second injection, the reactivity against EndoS gradually increased (FIG. 7A, Second injection, Day 5-10). Before the third injection of EndoS, the ELISA data confirmed that the reactivity against EndoS was slightly higher than before the second injection, and the reactivity did not increase during the first day after injection (FIG. 7A, Third injection, Day 0-1). From day 5 to 10 after the third injection, the ELISA data revealed that reactivity against EndoS increased dramatically (FIG. 7A, Third injection, Day 5-10).

These results indicate that there are antibodies directed towards EndoS in unexposed animals and that rEndoS elicits an immune response in rabbits upon repated intravenous exposure. However, these antibodies do not interfere with the activity of rEndoS in the circulation during three consecutive administrations. Furthermore, repeated administration does not affect the approximately 12 hours circulation time (defined as the ability to detect EndoS) of the enzyme as analyzed by immunoprecipitation and Western blot analysis of EndoS from rabbit serum samples.

Example 4

EndoS Cleaves CII-Specific Monoclonal Antibodies

Figure 8:
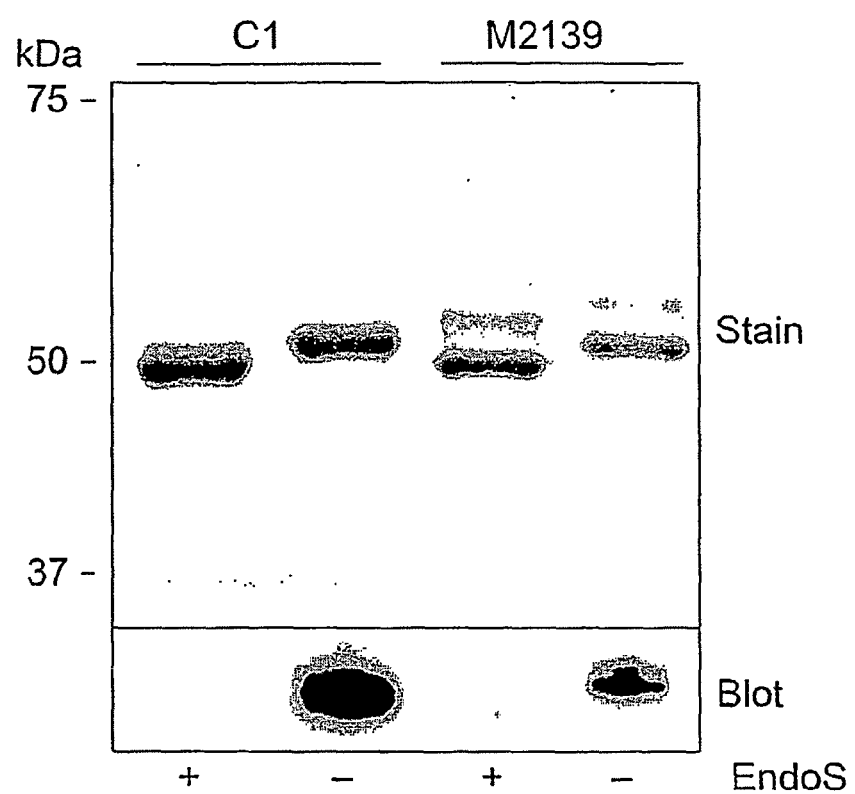
FIG. 8 shows SDS-PAGE (Stain) and lectin blot analysis (Blot) of IgG monoclonal antibodies (CIIC1 and M2139) incubated with and without EndoS and separated by 10% SDS-PAGE. Gels were analysed by Coomassie Blue staining (Stain) or by blotting to a membrane that was probed with GNL lectin (Blot). CIIC1 (IgG2a) monoclonal antibody was incubated with EndoS (Lane 1) and without EndoS (Lane 2); M2139 (IgG2b) monoclonal antibody was incubated with EndoS (Lane 3) and without Endo S (Lane 4).

SDS-PAGE and lectin blot analysis of IgG monoclonal antibodies (CIIC1 and M2139) incubated with and without EndoS and separated by 10% SDS-PAGE was carried out and the results are shown in FIG. 8.

EndoS specifically hydrolyzes the β-1,4-di-N-acetylchitobiose core of the asparagine-linked glycan of immunoglobulin (IgG). After the removal of the carbohydrate side chain using EndoS, IgG molecular weight is reduced. The difference in size of the γ-chains can be clearly seen in the stained gel picture between the IgG sample treated with EndoS and non-treated IgG.

To confirm that the size alteration of IgG was caused by EndoS activity and resulted in the removal of the glycan moiety on γ-chains rather than proteolytic degradation, a lectin blot analysis was performed. The lectin from *Galanthus nivalis* (GNL) preferentially recognizes α-1,3 mannose residues found in the biantennary glycan on γ-chains. Lectin blot analysis of the same samples with the GNL lectin revealed a significantly reduced signal when incubated with EndoS. In contrast, the γ-chains were still glycosylated when incubated in the absence of EndoS. These data indicate that EndoS has the ability to remove structures containing α-1,3 mannose from the γ-chains of mouse IgG.

Example 5

Deglycosylated Antibodies Bind to Cartilage In Vivo

This experiment was performed to understand whether the removal of carbohydrate moieties from collagen type II (CII) specific IgG monoclonal antibody (mAb) affected its binding capacity to collagen type II in vivo.

Figure 9:
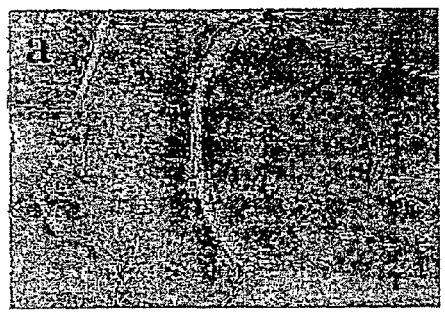
FIG. 9 shows joint sections (10 μm) from rats treated with normal and EndoS-treated CII-binding antibodies: (a) M2139, (b) M2139D, (c) CIIC1, (d) CIIC1D and (e) control; and stained. Magnification is ×10. Antibodies deglycosylated using EndoS are indicated as "D". 1-2 day old neonatal rats were injected with 1 mg of CII-binding antibody (both normal and EndoS treated) i.p. Twenty-four hours after the antibody transfer, paws were dissected and snap frozen in OCT compound using isopentane and dry ice. Immuno-histochemical analysis was performed using biotinylated anti-mouse kappa (187.1) antibody and HRP conjugated secondary antibody as the detecting system using standard protocol.
Figure 9:
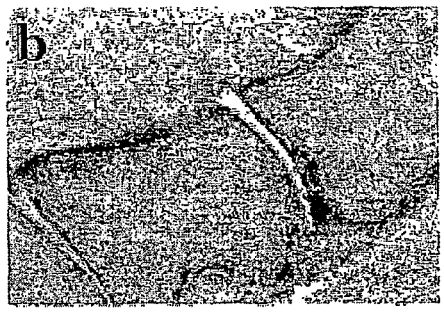
Figure 9:
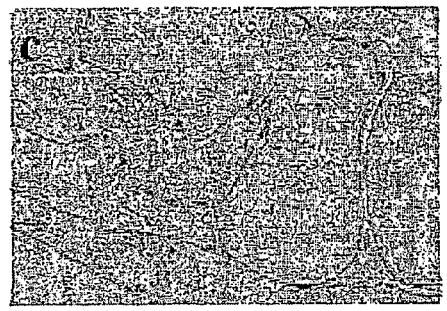
Figure 9:
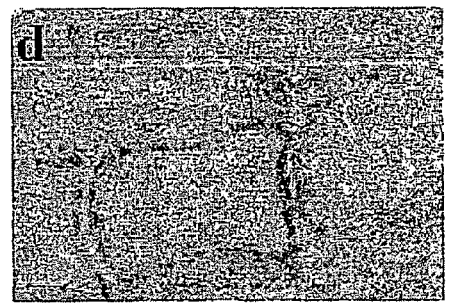
Figure 9:
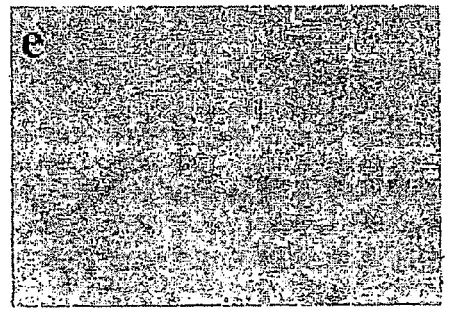

1-2 day old neonatal rats were injected with 1 mg of CII-binding antibody (both normal and EndoS treated) i.p. Twenty-four hours after the antibody transfer, paws were dissected and snap frozen in OCT compound using isopentane and dry ice. Immuno-histochemical analysis was performed using biotinylated anti-mouse kappa (187.1) antibody and HRP conjugated secondary antibody as the detecting system using standard protocol. The results are shown in FIG. 9. There was no difference in the binding pattern of EndoS treated and untreated antibodies to the joint cartilage in vivo.

Example 6

Loss of Arthritogenicity by Deglycosylation of Anti-CII Monoclonal Antibodies

CII-specific monoclonal antibodies induce an acute form of arthritis in mice, the so-called collagen antibody induced arthritis (CAIA) described in Nandakumar et at (2003). CAIA resembles the effector phase of arthritis without involving the priming phase of the immune response. This antibody-mediated arthritis is dependent on complement components, FcγRs, effector cytokines TNF-α and IL-1β and on neutrophils and macrophages. CAIA was used in the present study to understand the importance of deglycosylation of IgG by EndoS treatment. A monoclonal antibody cocktail containing two antibodies: M2139 mAb (IgG2b), which binds to J1 epitope (551-564; GERGAAGIAGPK; SEQ ID NO:28), and CIIC1 (IgG2a), which binds to C1[1] (359-363; ARGLT; SEQ ID NO:29) of collagen type II, was used to induce an acute form of arthritis, CAIA.

Figure 10:
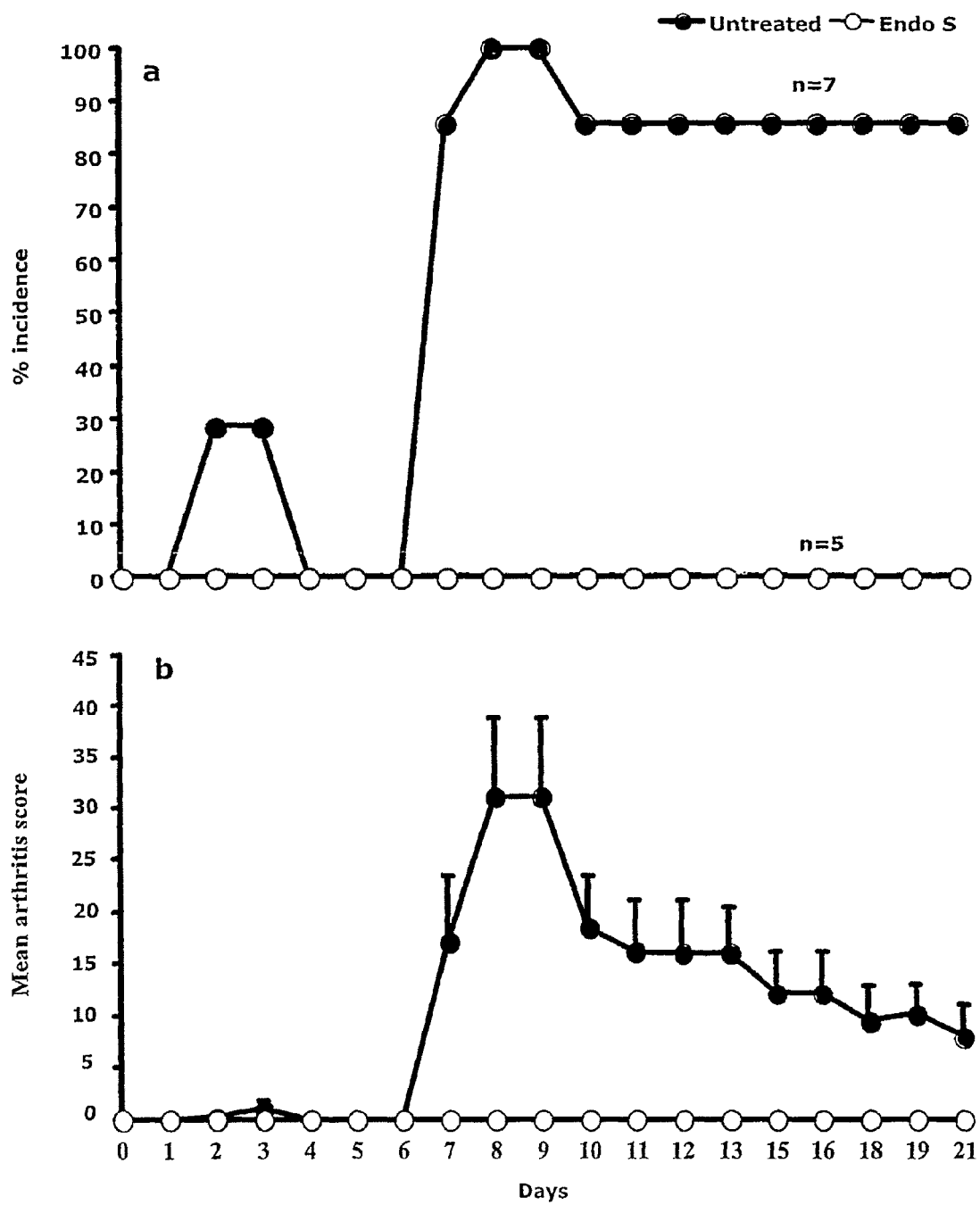
FIG. 10 shows the incidence (a) and severity (b) of arthritis in mice receiving untreated or EndoS-treated anti-CII monoclonal antibodies. Groups of male (BALB/c×B10.Q) F1 mice were injected with 9 mg of either untreated (n=7) or EndoS treated (n=5) anti-CII monoclonal antibodies (M2139 and CIIC1) on day 0. All of the mice were injected with 50 μg of *E. coli* LPS i.p. on day 5. All the mice were included for calculations. Error bars indicate mean±SEM.

In order to determine whether the removal of carbohydrate side chains affects the arthritis-inducing capacity of pathogenic monoclonal antibodies to collagen type II, this cocktail of monoclonal antibodies, treated with EndoS or untreated, was injected into mice. Groups of male (BALB/c×B10.Q) F1 mice were injected with 9 mg of either untreated (n=7) or EndoS treated (n=5) anti-CII monoclonal antibodies (M2139 and CIIC1) on day 0. All of the mice were injected with 50 μg of *E. coli* LPS i.p. on day 5. Arthritis incidence (a) and mean arthritis score (b) are shown in FIG. 10.

As can be seen from FIGS. 10a and 10b, there was absolute inhibition of clinical arthritis in (BALB/c×B10.Q) F1 mice that were earlier shown to be highly susceptible for collagen antibody induced arthritis (CAIA). Thus, it is clear that removal of carbohydrate from γ-chains of IgG by EndoS abrogates its arthritis-inducing capacity (arthritogenicity).

To confirm the loss of arthritogenicity of monoclonal antibodies by removal of carbohydrate side chains of IgG, CAIA was induced in mice having another genetic background, B10.RIII.

Figure 11:
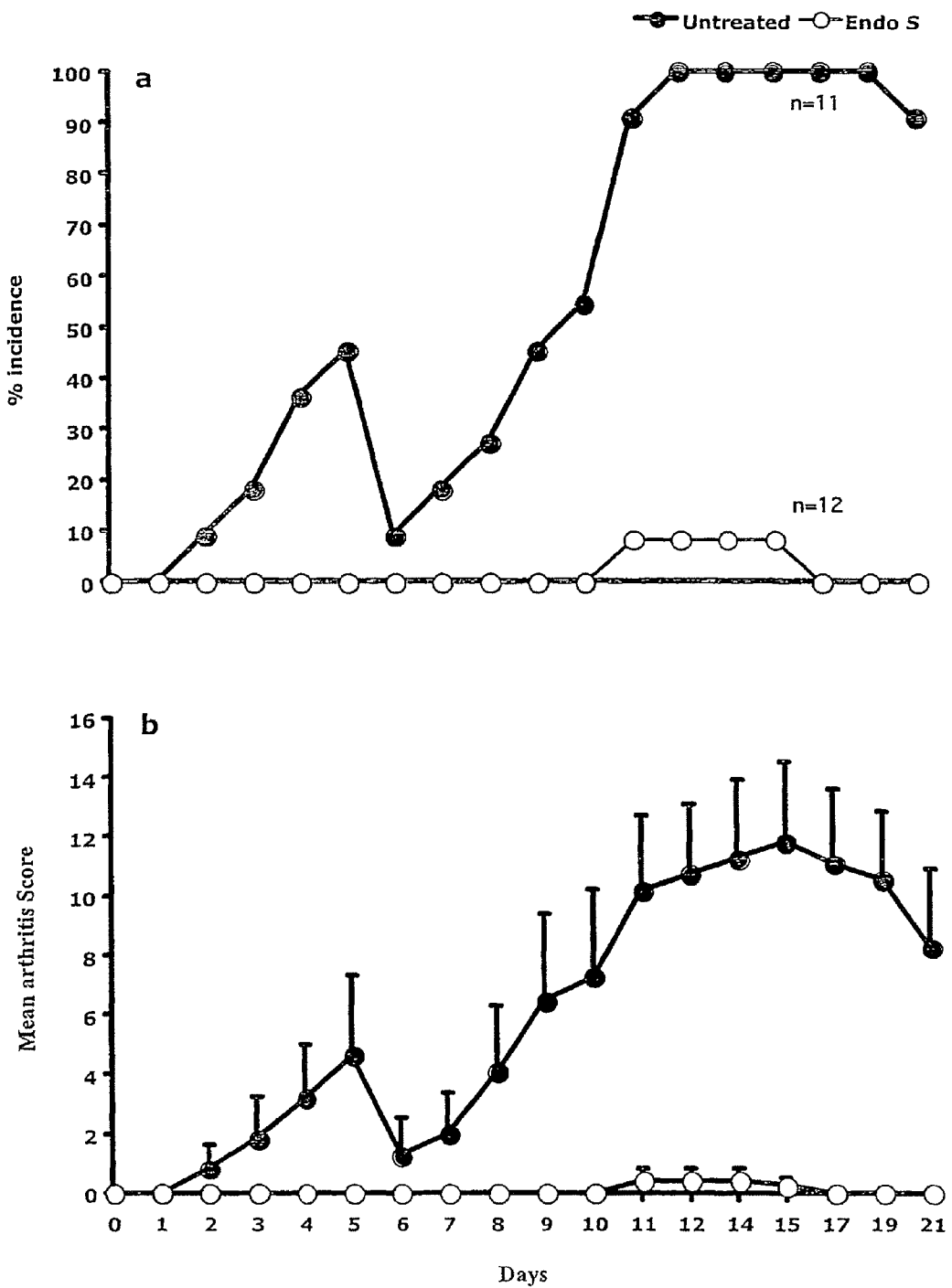
FIG. 11 shows the incidence (a) and severity (b) of arthritis in mice receiving untreated or EndoS-treated anti-CII monoclonal antibodies. Male B10.RIII mice were injected with 9 mg of either untreated (n=11) or EndoS treated (n=12) anti-CII monoclonal antibodies (M2139 and CIIC1) on day 0. All of the mice were injected with 50 μg of *E. coli* LPS i.p. on day 5. All the mice were included for calculations. Error bars indicate mean±SEM.

Male B10.RIII mice were injected with 9 mg of either untreated (n=11) or EndoS treated (n=12) anti-CII monoclonal antibodies (M2139 and CIIC1) on day 0. All of the mice were injected with 50 μg of *E. coli* LPS i.p. on day 5. Arthritis incidence (a) and mean arthritis score (b) are shown in FIG. 11. As can be seen from FIG. 11, in the B10.RIII mice, there was significantly reduced incidence and severity of arthritis induced by the EndoS-treated mAb cocktail compared to the untreated cocktail of mAbs.

Example 7

Complement activation by CII-reactive monoclonal antibodies in vitro

In order to understand why the removal of carbohydrate from γ-chains of IgG reduced or abolished the clinical arthritis-inducing capacity of mAbs, in vitro experiments were performed with the EndoS treated and untreated antibodies to assess their capacity to induce complement activation.

Figure 12:
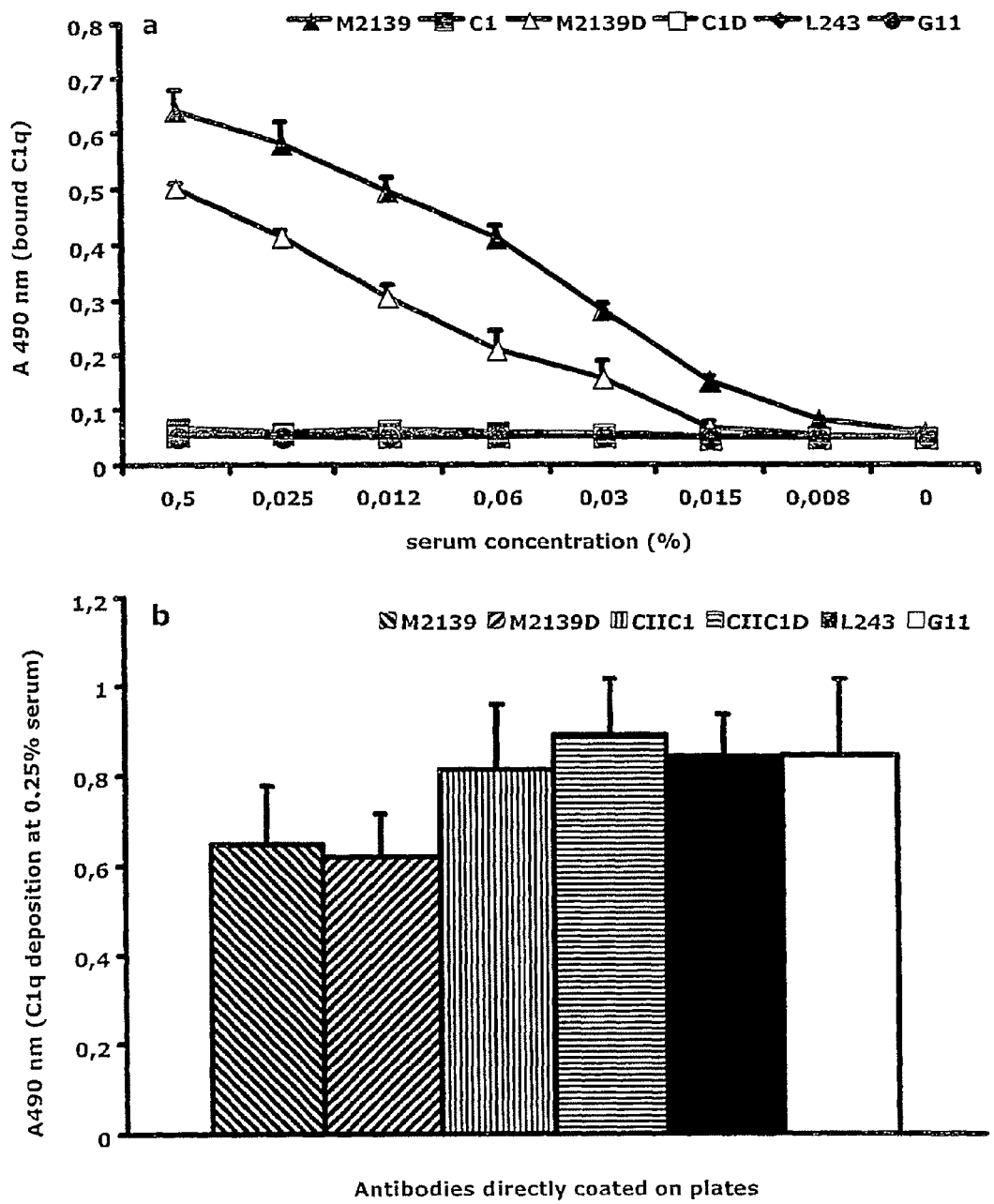
FIG. 12 shows deposition of complement component C1q on: (a) CII-coated antibody bound plates using different concentrations of normal (BALB/c×B10.Q) F1 serum; and (b) directly antibody coated plates at 0.25% normal (BALB/c× B10.Q) F1 serum. Error bars indicate±SD.

FIG. 12 shows the first complement component C1q deposition on mAbs binding to collagen type II (a) or directly to a plastic surface (b). There was no difference in the activation of complement system by EndoS treated (M2139D) and untreated (M2139) antibodies. CIIC1 (both EndoS treated and untreated) mAb did not activate the complement at all. G11 (IgG2b) and L243 (IgG2a) are control monoclonal antibodies binding to irrelevant antigens.

Figure 13:
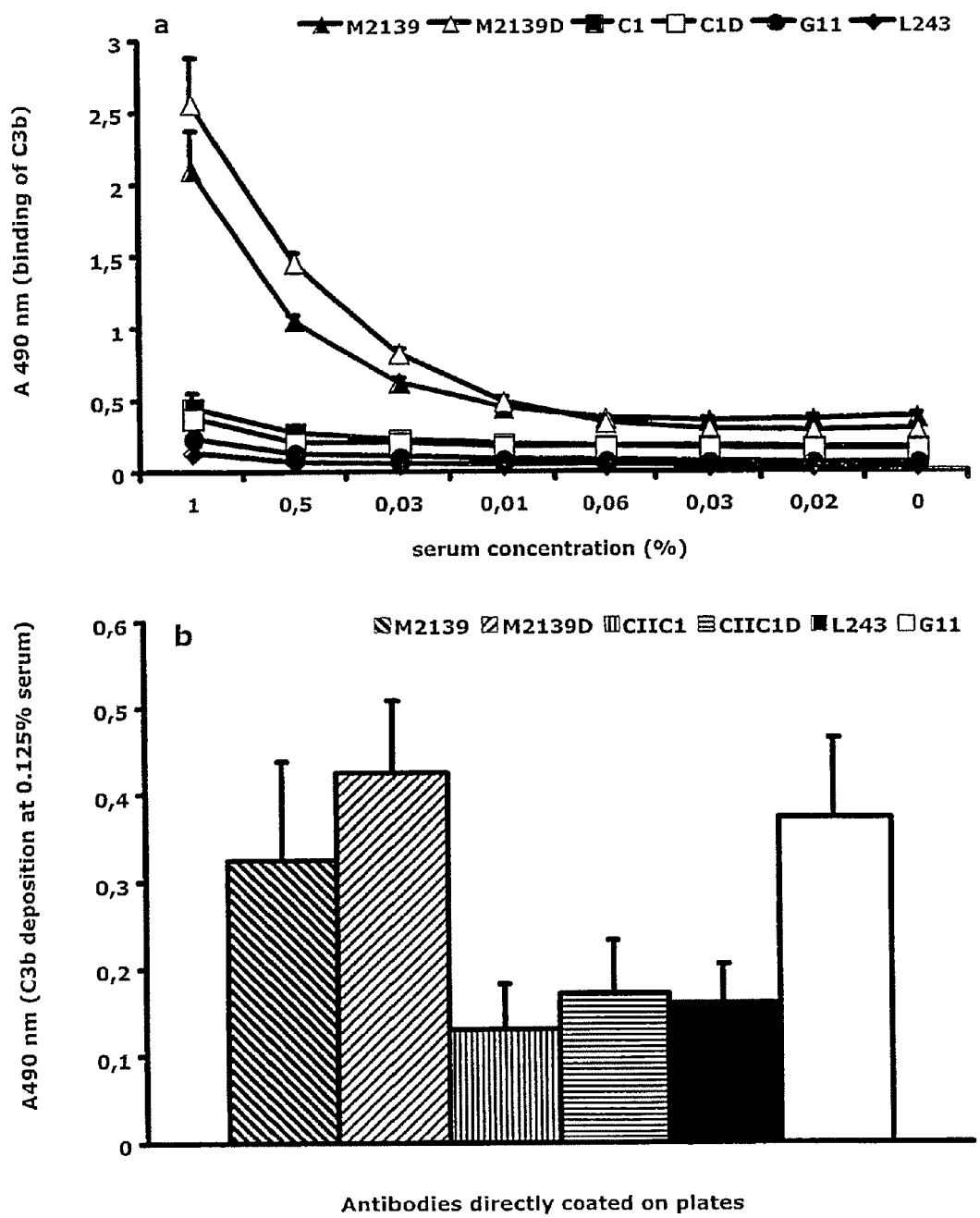
FIG. 13 shows deposition of complement component C3b on: (a) CII-coated antibody bound plates using different concentrations of normal (BALB/c×B10.Q) F1 serum; and (b) directly antibody coated plates at 0.125% normal (BALB/c× B10.Q) F1 serum. Error bars indicate±SD.

FIG. 13 shows the deposition of cleaved product (C3b) of complement component C3 on mAbs binding to collagen type II (a) or directly to a plastic surface (b). There was no difference in the activation of complement system by EndoS treated (M2139D) and untreated (M2139) antibodies. CIIC1 (both EndoS treated and untreated) mAb did not activate the complement at all. G11 (IgG2b) and L243 (IgG2a) are control monoclonal antibodies binding to irrelevant antigens.

Example 8

Effect of Deglycosylation of CII-Specific Monoclonal Antibodies on Neutrophil (PMNL) Oxidative Burst In order to determine whether there is a functional difference in the capacity of glycosylated and deglycosylated antibodies in inducing the oxidative burst by polymorphonuclear leukocytes, PMNL (neutrophils), polystyrene microparticles were coated with EndoS treated and untreated antibodies and incubated with whole blood from mice having three different genotypes (FcgR+/+, FcgR-/- and FcgR+/-). Oxidative burst assays were then performed using FACS (Fluorescence Activated Cell Sorting) analysis. PMNLs were identified using RB6 antibodies.

Figure 14:
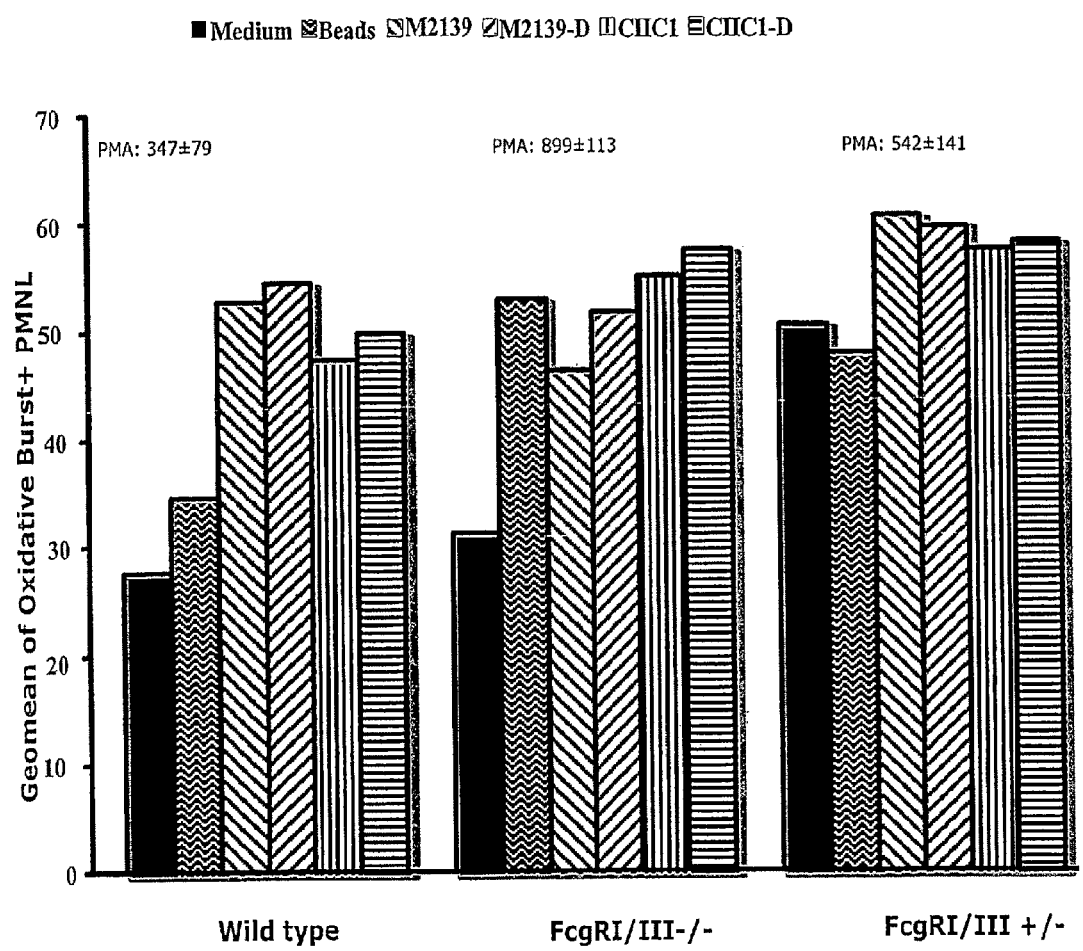
FIG. 14 shows the effect of deglycosylation of monoclonal antibodies on the neutrophil (PMNL) oxidative burst. Normal (M2139 or CIIC1) or deglycosylated (M2139-D or CIIC1-D) monoclonal antibodies were coated on carboxylated polystyrene microparticles (1 μm). The oxidative burst capacity of PMNLs from heparinized whole blood samples was determined using FACS after incubating them with antibody-coated beads. The results are mean values from 5 mice in each group. B10.Q mice having three different genotypes were used (FcgR+/+, FcgR−/− and FcgR+/−). The "medium" and "beads" groups constituted two different negative controls. The PMA group was the positive control. PMNLs were identified using RB6-APC conjugate.

The results are shown in FIG. 14. There was no difference in the activation of oxidative burst between glycosylated and deglycosylated antibodies.

Example 9

Histology of Mouse Paws

To check the histological status of joints from mouse paws that received glycosylated or EndoS treated mAbs, standard hematoxylin-eosin staining was used to stain 6 μm sections of formalin fixed decalcified joints from (BALB/c×B10.Q) F1 mice (n=3-4) injected with 9 mg of untreated, deglycosylated or an equal mixture of untreated and EndoS treated antibody cocktail.

The results showed that there was a massive infiltration of cells and cartilage and bone erosion in the joints from mice injected with glycosylated antibodies. In contrast, mouse paws injected with EndoS treated antibodies showed only minor bone erosion and no massive cell infiltration. The cartilage looked normal in these mice.

Example 10

Clearance of Normal and Deglycosylated Antibodies In Vivo

Figure 15:
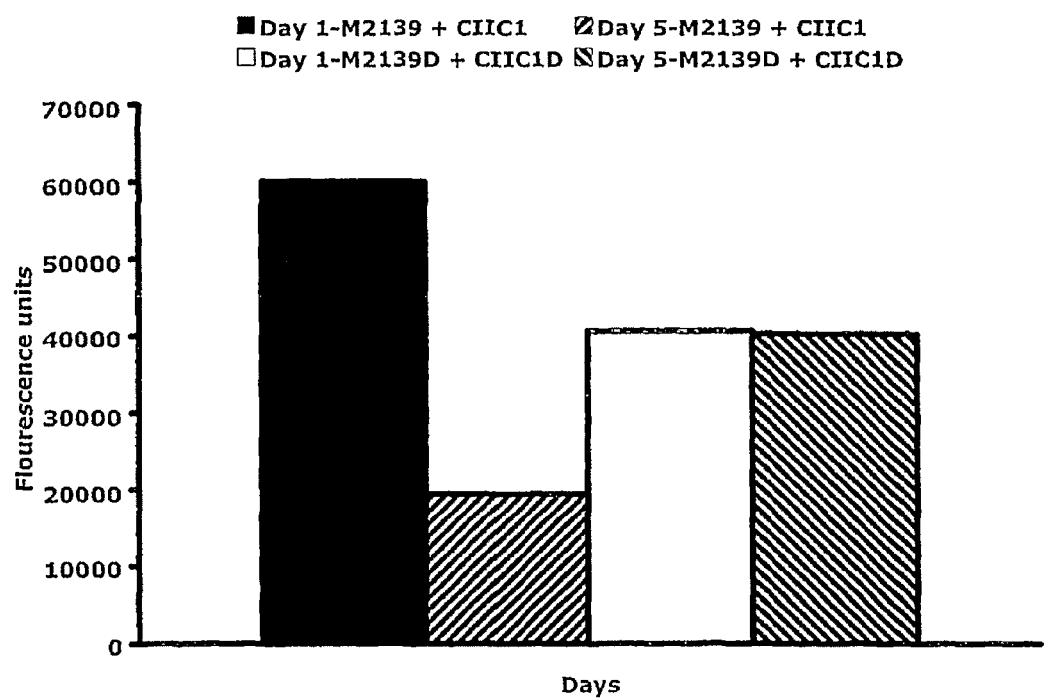
FIG. 15 shows the level of anti-CII antibodies measured by ELISA in the serum of B10.RIII mice (day 1 and day 5) transferred with 9 mg of monoclonal antibody cocktail (M2139 and CIIC1 or M2139D and CIIC1D) i.v. Mean europium fluorescence units were measured using a multilabel counter (VICTOR 1420, Wallac).

In order to determine whether the reduced arthritogenicity of deglycosylated antibodies was due to early and enhanced clearance of these antibodies from the mouse compared to glysosylated antibodies, analysis of collagen type II binding antibodies by ELISA (enzyme linked immunosorbent assay) was performed using the sera collected from B10.RIII mice on day 1 and 5. The results are shown in FIG. 15. There was no difference between the levels of antibodies present in the serum of mice injected with glysosylated and EndoS treated mAbs, suggesting a normal clearance level of the deglycosylated antibodies from mice.

Example 11

Immune Complex Formation by Deglycoslyated Antibodies

We wished to determine whether any obvious differences exist between glycosylated and EndoS treated antibodies, apart from binding differences to FcγR molecules. It is most likely that the first step in the initial triggering event in the antibody transfer arthritis model is the formation of collagen—IgG immune complexes on the cartilage surface or in the synovium. Collagen epitopes are located in a repetitive structure formed on the cartilage surface, and hence it is possible that the two different antibodies can form multimeric complexes on the joint surfaces favouring arthritogenicity either by optimal complement activation or by binding to FcγR bearing cells.

In order to investigate the issue of stable immune complex formation, single immunodiffusion of antibodies was performed on agarose. Rat CII was impregnated in 1% agarose (low gelling temperature agarose 26-30° C.) gel at 1 mg/ml in PBS containing 0.05% sodium azide. 25 ul of antibodies at 1 mg/ml concentration were loaded per well. Gel was stained with Coomassie Blue. The results showed that deglycosylated antibodies did not form stable immune complexes compared to glysosylated mAbs. This inability to form stable immune complexes could be another explanation for the loss of arthritogenicity of deglycosylated antibodies.

Example 12

EndoS Rescues Mice from Lethal Antibody-Mediated Thrombocytopenia

Having established that EndoS efficiently hydrolyses the IgG glycan in vivo and that animals tolerated administration of the enzyme, we investigated the use of EndoS to treat a serious IgG-mediated disease. The disease model chosen was a mouse model of immune thrombocytopenic purpura (ITP). In this model polyclonal rabbit IgG directed against mouse platelets (αPLT-IgG) is injected intraperitoneally, leading to severe thrombocytopenia, bleedings, and ultimately death at higher doses of IgG.

Rabbit antiserum against mouse platelets was purchased from Inter-Cell Technologies (Jupiter, Fla.). The IgG fraction was isolated from this serum using protein G Sepharose. Protein purity was confirmed by SDS-PAGE analysis and protein concentration was determined using Advanced Protein Assay Reagent (Cytoskeleton, Denver, Colo.). For experiments using pre-treated IgG, purified rabbit anti-mouse platelet IgG (αPLT-IgG) was incubated with purified GST-EndoS or GST, at an enzyme to substrate ratio of 1:500 at 37° C. for 24 hours followed by removal of GST-EndoS and GST on a Glutathione-Sepharose (GE Healthcare). IgG glycan hydrolysis was confirmed by SDS-PAGE and lectin blotting using LCA as described above. Female BALB/c mice (approx. weight 20 g) were housed under standard conditions of light and temperature and were fed standard laboratory chow and water ad libitum. 1.2 mg of anti-mouse platelet IgG (untreated, EndoS treated, or GST treated) in 0.25 ml PBS was administered to the animals by intraperitoneal (i.p.) injection. Animals were monitored for mucocutaneous bleeds, physical activity, isolation from the group, and the survival time was recorded.

Immediately prior to the injection of rabbit anti-mouse platelet IgG and at regular intervals during the course of experiments, blood samples were collected from mice. From the pre-warmed tail vein, 5 μl of whole blood was collected into tubes containing 45 μl of 0.1 M sodium citrate/citric acid in PBS (pH 6.5). The platelet population in these blood samples was identified by flow cytometry. Samples were labeled with hamster anti-mouse CD-61 PE (BD Biosciences, San Jose, Calif.) for 10 min at room temperature. Ten μl of SPHERO$^a$ Rainbow Calibration Particles (BD Biosciences) were added to each tube, to enable counting. The red cell populations was lyzed using Utilyse$^a$ (Dako Cytomation, Glostrup, Denmark) and the samples were analyzed on a FacsCalibur flow cytometer (BD Biosciences) in the logarithmic mode. The platelet number in the blood samples after lysis of red blood cells, was continued by manual counting in a Neubauer chamber.

Figure 16:
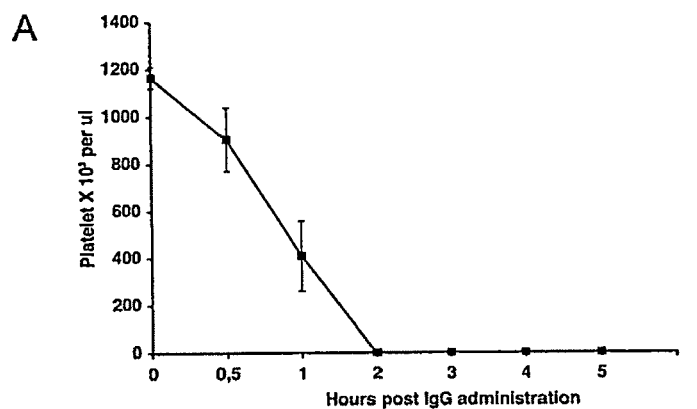
FIG. 16 shows that EndoS pretreatment of pathogenic IgG antibodies inhibits antibody-mediated thrombocytopenia in mice. Panel A: Female BALB/c mice (n=3) received intraperitoneal injections of rabbit anti-mouse platelet IgG (αPLT-IgG). Blood samples were taken at regular intervals and platelet counts were determined using flow cytometry. Panel B: Survival plots of BALB/c mice injected with αPLT-IgG that had been pretreated with GST-EndoS (n=4) or GST (n=4). Panel C: Platelet counts over time as determined by flow cytometry on blood samples from mice that had received αPLT-IgG pretreated with GST-EndoS.
Figure 16:
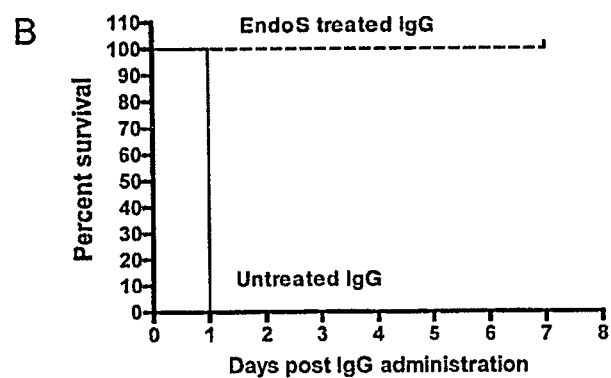
Figure 16:
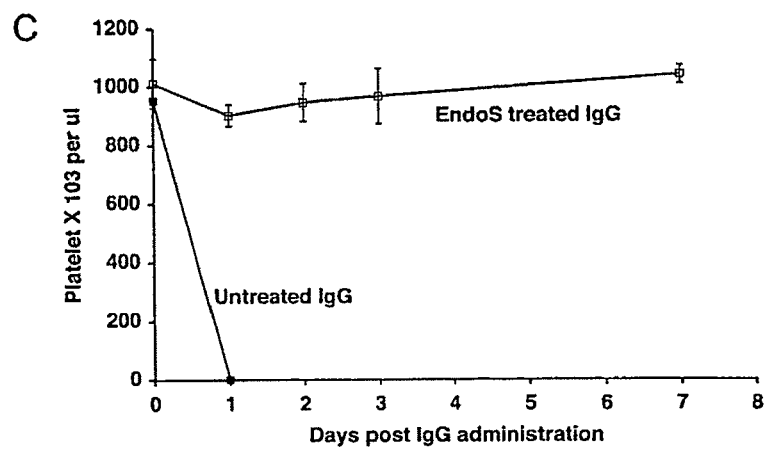

In a pilot experiment, three female BALB/c mice were injected with 1.2 mg of αPLT-IgG and platelet counts were followed over time using flow cytometry and microscopy as described above. This revealed that all three mice rapidly developed thrombocytopenia and death occurred within 24 hours after αPLT-Ig administration (FIG. 16A).

Figure 17:
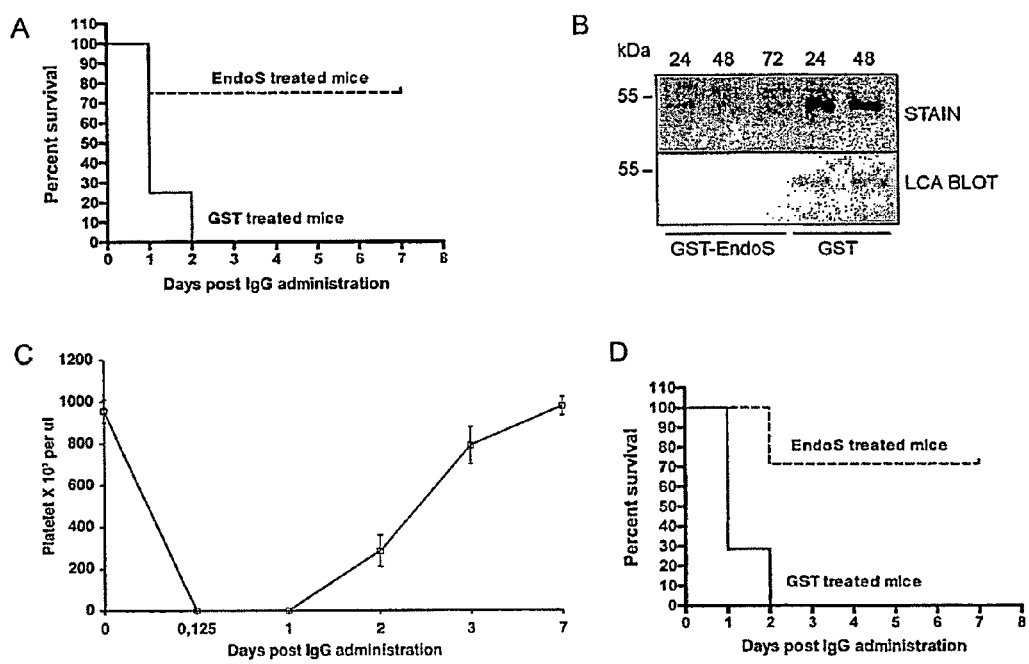
FIG. 17 shows that EndoS rescues mice from lethal IgG-mediated thrombocytopenia. Panel A: Survival plots of BALB/c mice injected with αPLT-IgG followed by GST-EndoS (n=8) or GST (n=8) treatment 3 hours after αPLT-IgG administration. Panel B: SDS-PAGE analysis (STAIN) and LCA lectin blot analysis (LCA BLOT) of IgG purified from GST-EndoS or GST-treated mice 24, 48, or 72 (only GST-EndoS) hours after injection of αPLT-Ig. Panel C: Blood samples was taken at regular intervals and platelet counts were determined using flow cytometry in mice that received GST-EndoS treatment. Panel D, survival plots of BALB/c mice injected with αPLT-Ig followed by GST-EndoS (n=7) or GST (n=7) treatment at the onset of clear signs of intra-abdominal bleeding (5-7 h after αPLT-Ig administration).

Next, we tested if pre-treatment of αPLT-IgG with GST-EndoS, or GST as a control, prior to administration to mice had any effects on the development of disease and survival rate. All animals (n=4) injected with GST-EndoS-treated αPLT-IgG survived without developing any signs of disease, while all animals (n=4) injected with GST-treated αPLT-Ig developed severe subcutaneous bleeding and died within 24 hours (FIG. 16B). This represents a statistically significant difference between the two groups of animals (p=0.0082). Furthermore, daily platelet count analysis by flow cytometry revealed that GST-EndoS-treated αPLT-IgG had no significant effect on mouse platelet count, while GST-treated αPLT-IgG caused a rapid drop in platelet counts (FIG. 16C). These experiments demonstrated that EndoS-treatment of αPLT-IgG ex vivo abrogated the pathogenicity of the IgG antibodies, results, which in combination with the in vivo activity of EndoS, stimulated us to investigate whether EndoS could be administered to mice after initiation of disease to prevent the development of lethal thrombocytopenia. Mice (n=8 per group) were injected with 1.2 mg of αPLT-IgG followed by intraperitoneal injection of 100 μg of GST-EndoS or GST 3 hours after the administration of αPLT-Ig. All animals (8/8) that were treated with GST died within two days, while only 2/8 animals treated with GST-EndoS died (FIG. 17A). This represents a statistically significant difference in survival rate between the groups (p=0.003). SDS-PAGE and lectin blot analysis of total IgG from GST-EndoS or GST treated mice, showed that the heavy chain glycan was completely hydrolyzed at 24, 48 and 72 hours post αPLT-IgG treatment in GST-EndoS-treated animals, while the IgG in GST-treated animals was fully glycosylated until death occurred at 24 hours (FIG. 17B). Furthermore, the platelet count as analyzed by flow cytometry showed that administration of αPLT-IgG induces a rapid fall in platelet count, but in GST-EndoS-treated mice the platelet count began to rise steadily and reached normal values after 2-3 days (FIG. 17C).

In order to challenge our hypothesis further, we attempted to mimic the clinical situation of ITP patients. When these patients seek medical attention, the platelet count is often very low and subcutaneous and other bleeding complications are already manifest. We therefore induced disease in mice (n=14) with αPLT-IgG, but did not initiate treatment with GST-EndoS or GST until animals exhibited clearly visible cutaneous hematomas 5-7 hours after αPLT-IgG injection. In these experiments 5/7 of mice treated with GST-EndoS survived and recovered, while all (7/7) mice treated with GST died within 2 days, again representing a statistically significant difference in the survival rate between the two groups (p=0.0015) (FIG. 17D). Combined, our results demonstrate that the pathogenic properties of αPLT-IgG in mice is dependent on the glycosylations state of the antibodies and that EndoS both ex vivo and in vivo drastically reduces the pathogenicity of anti-platelet IgG antibodies. In summary, EndoS had dramatic positive effects on the platelet count and survival, both when pathogenic antibodies were pretreated with the enzyme and when EndoS was administered early or late during the course of disease. To the inventors knowledge, this is the first time that in vivo hydrolysis of IgG glycans has been used as an experimental treatment of an autoimmune disease.

The mechanisms underlying the positive effects of EndoS are from a theoretical viewpoint quite clear, since the inventors have previously found that EndoS hydrolysis of IgG inhibits IgG of all subclasses from binding to FcRs and also reduces complement activation. What is of particular interest is that not only does EndoS inhibit IgG from binding FcRs, but it can also release already FcR-bound IgG by hydrolysis of the heavy chain glycan. It should also be noted that there seems to be one IgG-FcR interaction that is not affected like the others; EndoS hydrolyzed IgG does under certain circumstances bind better to human FcR11b than non-hydrolyzed IgG (data not shown). In the context of anti-inflammatory activity this might be of relevance, since IgG interactions with FcR11b have been shown to be important for the anti-inflammatory activity of Intravenous immunoglobulin (WIG) that is used to treat autoimmune conditions. Without being bound by any hypothesis, the inventors suggest that EndoS under certain circumstances may have a dual anti-inflammatory activity by directly inhibiting the binding of pathogenic IgG to activating FcRs, and shifting towards the inhibitory action mediated through FcR11b.

The properties of EndoS make it an attractive alternative to current therapies of conditions involving pathogenic antibodies, especially in the light of several recent studies establishing the IgG glycan as a key to IgG effector modulation. This includes the inventors own findings that EndoS hydrolysis of this glycan nearly abolishes complement activation through the classical pathway and reduces binding to Fc-receptors on leukocytes. Based on the inventors observations, it is shown that EndoS can be used to treat conditions where IgG antibodies play a pathogenic role, including autoimmune diseases as exemplified here by ITP, and acute antibody-mediated organ allograft rejections.

The invention claimed is:

1. A method of treating or preventing a disease or condition mediated by IgG antibodies in a subject in need thereof, wherein the method of treating the disease or condition comprises administering to the subject a therapeutically effective amount of the polypeptide consisting of SEQ ID NO: 1 and wherein the method of preventing the disease or condition comprises administering to the subject a prophylactically effective amount of the polypeptide consisting of SEQ ID NO: 1.

2. A method of treating, ex vivo, blood taken from a patient suffering from a disease or condition mediated by IgG antibodies, comprising contacting the blood with an EndoS polypeptide.

3. A method according to claim 2, wherein the blood is returned to the patient after contacting it with said EndoS polypeptide.

4. A method of treating or preventing rheumatoid arthritis in a subject in need thereof, wherein the method of treating comprises administering to the subject a therapeutically effective amount of an EndoS polypeptide and wherein the method of preventing comprises administering to the subject a prophylactically effective amount of an EndoS polypeptide.

5. A method of treating or preventing systemic lupus erythematosus in a subject in need thereof, wherein the method of treating comprises administering to the subject a therapeutically effective amount of an EndoS polypeptide and wherein the method of preventing comprises administering to the subject a prophylactically effective amount of an EndoS polypeptide.

6. A method of treating or preventing idiopathic thrombocytopenic purpura in a subject in need thereof, wherein the method of treating comprises administering to the subject a therapeutically effective amount of an EndoS polypeptide and wherein the method of preventing comprises administering to the subject a prophylactically effective amount of an EndoS polypeptide.

7. A method of treating or preventing allograft or xenograft rejection of a transplant in a subject in need thereof, wherein the method of treating comprises administering to the subject a therapeutically effective amount of an EndoS polypeptide and wherein the method of preventing comprises administering to the subject a prophylactically effective amount of an EndoS polypeptide.

* * * * *

SEQUENCE LISTING

<160> NUMBER OF SEQ ID NOS: 29

<210> SEQ ID NO 1
<211> LENGTH: 959
<212> TYPE: PRT
<213> ORGANISM: Streptococcus pyogenes
<220> FEATURE:
<223> OTHER INFORMATION: Streptococcus pyogenes serotype M1 strain AP1
    secreted endoglycosidase EndoS mature form

<400> SEQUENCE: 1

Glu Glu Lys Thr Val Gln Val Gln Lys Gly Leu Pro Ser Ile Asp Ser
1               5                   10                  15

-continued

```
Leu His Tyr Leu Ser Glu Asn Ser Lys Lys Glu Phe Lys Glu Glu Leu
         20                  25                  30
Ser Lys Ala Gly Gln Glu Ser Gln Lys Val Lys Glu Ile Leu Ala Lys
             35                  40                  45
Ala Gln Gln Ala Asp Lys Gln Ala Gln Glu Leu Ala Lys Met Lys Ile
 50                  55                  60
Pro Glu Lys Ile Pro Met Lys Pro Leu His Gly Pro Leu Tyr Gly Gly
 65                  70                  75                  80
Tyr Phe Arg Thr Trp His Asp Lys Thr Ser Asp Pro Thr Glu Lys Asp
                 85                  90                  95
Lys Val Asn Ser Met Gly Glu Leu Pro Lys Glu Val Asp Leu Ala Phe
                100                 105                 110
Ile Phe His Asp Trp Thr Lys Asp Tyr Ser Leu Phe Trp Lys Glu Leu
             115                 120                 125
Ala Thr Lys His Val Pro Lys Leu Asn Lys Gln Gly Thr Arg Val Ile
130                 135                 140
Arg Thr Ile Pro Trp Arg Phe Leu Ala Gly Gly Asp Asn Ser Gly Ile
145                 150                 155                 160
Ala Glu Asp Thr Ser Lys Tyr Pro Asn Thr Pro Glu Gly Asn Lys Ala
                165                 170                 175
Leu Ala Lys Ala Ile Val Asp Glu Tyr Val Tyr Lys Tyr Asn Leu Asp
            180                 185                 190
Gly Leu Asp Val Asp Val Glu His Asp Ser Ile Pro Lys Val Asp Lys
            195                 200                 205
Lys Glu Asp Thr Ala Gly Val Glu Arg Ser Ile Gln Val Phe Glu Glu
        210                 215                 220
Ile Gly Lys Leu Ile Gly Pro Lys Gly Val Asp Lys Ser Arg Leu Phe
225                 230                 235                 240
Ile Met Asp Ser Thr Tyr Met Ala Asp Lys Asn Pro Leu Ile Glu Arg
                245                 250                 255
Gly Ala Pro Tyr Ile Asn Leu Leu Leu Val Gln Val Tyr Gly Ser Gln
            260                 265                 270
Gly Glu Lys Gly Gly Trp Glu Pro Val Ser Asn Arg Pro Glu Lys Thr
        275                 280                 285
Met Glu Glu Arg Trp Gln Gly Tyr Ser Lys Tyr Ile Arg Pro Glu Gln
290                 295                 300
Tyr Met Ile Gly Phe Ser Phe Tyr Glu Glu Asn Ala Gln Glu Gly Asn
305                 310                 315                 320
Leu Trp Tyr Asp Ile Asn Ser Arg Lys Asp Glu Lys Ala Asn Gly
                325                 330                 335
Ile Asn Thr Asp Ile Thr Gly Thr Arg Ala Glu Arg Tyr Ala Arg Trp
            340                 345                 350
Gln Pro Lys Thr Gly Gly Val Lys Gly Gly Ile Phe Ser Tyr Ala Ile
        355                 360                 365
Asp Arg Asp Gly Val Ala His Gln Pro Lys Lys Tyr Ala Lys Gln Lys
        370                 375                 380
Glu Phe Lys Asp Ala Thr Asp Asn Ile Phe His Ser Asp Tyr Ser Val
385                 390                 395                 400
Ser Lys Ala Leu Lys Thr Val Met Leu Lys Asp Lys Ser Tyr Asp Leu
                405                 410                 415
Ile Asp Glu Lys Asp Phe Pro Lys Ala Leu Arg Glu Ala Val Met
            420                 425                 430
```

-continued

```
Ala Gln Val Gly Thr Arg Lys Gly Asp Leu Glu Arg Phe Asn Gly Thr
            435                 440                 445

Leu Arg Leu Asp Asn Pro Ala Ile Gln Ser Leu Glu Gly Leu Asn Lys
450                 455                 460

Phe Lys Lys Leu Ala Gln Leu Asp Leu Ile Gly Leu Ser Arg Ile Thr
465                 470                 475                 480

Lys Leu Asp Arg Ser Val Leu Pro Ala Asn Met Lys Pro Gly Lys Asp
                485                 490                 495

Thr Leu Glu Thr Val Leu Glu Thr Tyr Lys Lys Asp Asn Lys Glu Glu
            500                 505                 510

Pro Ala Thr Ile Pro Pro Val Ser Leu Lys Val Ser Gly Leu Thr Gly
        515                 520                 525

Leu Lys Glu Leu Asp Leu Ser Gly Phe Asp Arg Glu Thr Leu Ala Gly
530                 535                 540

Leu Asp Ala Ala Thr Leu Thr Ser Leu Glu Lys Val Asp Ile Ser Gly
545                 550                 555                 560

Asn Lys Leu Asp Leu Ala Pro Gly Thr Glu Asn Arg Gln Ile Phe Asp
                565                 570                 575

Thr Met Leu Ser Thr Ile Ser Asn His Val Gly Ser Asn Glu Gln Thr
            580                 585                 590

Val Lys Phe Asp Lys Gln Lys Pro Thr Gly His Tyr Pro Asp Thr Tyr
        595                 600                 605

Gly Lys Thr Ser Leu Arg Leu Pro Val Ala Asn Glu Lys Val Asp Leu
        610                 615                 620

Gln Ser Gln Leu Leu Phe Gly Thr Val Thr Asn Gln Gly Thr Leu Ile
625                 630                 635                 640

Asn Ser Glu Ala Asp Tyr Lys Ala Tyr Gln Asn His Lys Ile Ala Gly
                645                 650                 655

Arg Ser Phe Val Asp Ser Asn Tyr His Tyr Asn Asn Phe Lys Val Ser
                660                 665                 670

Tyr Glu Asn Tyr Thr Val Lys Val Thr Asp Ser Thr Leu Gly Thr Thr
            675                 680                 685

Thr Asp Lys Thr Leu Ala Thr Asp Lys Glu Glu Thr Tyr Lys Val Asp
690                 695                 700

Phe Phe Ser Pro Ala Asp Lys Thr Lys Ala Val His Thr Ala Lys Val
705                 710                 715                 720

Ile Val Gly Asp Glu Lys Thr Met Met Val Asn Leu Ala Glu Gly Ala
                725                 730                 735

Thr Val Ile Gly Gly Ser Ala Asp Pro Val Asn Ala Arg Lys Val Phe
            740                 745                 750

Asp Gly Gln Leu Gly Ser Glu Thr Asp Asn Ile Ser Leu Gly Trp Asp
        755                 760                 765

Ser Lys Gln Ser Ile Ile Phe Lys Leu Lys Glu Asp Gly Leu Ile Lys
770                 775                 780

His Trp Arg Phe Phe Asn Asp Ser Ala Arg Asn Pro Glu Thr Thr Asn
785                 790                 795                 800

Lys Pro Ile Gln Glu Ala Ser Leu Gln Ile Phe Asn Ile Lys Asp Tyr
                805                 810                 815

Asn Leu Asp Asn Leu Leu Glu Asn Pro Asn Lys Phe Asp Asp Glu Lys
            820                 825                 830

Tyr Trp Ile Thr Val Asp Thr Tyr Ser Ala Gln Gly Glu Arg Ala Thr
        835                 840                 845

Ala Phe Ser Asn Thr Leu Asn Asn Ile Thr Ser Lys Tyr Trp Arg Val
```

-continued

```
            850                 855                 860
Val Phe Asp Thr Lys Gly Asp Arg Tyr Ser Ser Pro Val Val Pro Glu
865                 870                 875                 880

Leu Gln Ile Leu Gly Tyr Pro Leu Pro Asn Ala Asp Thr Ile Met Lys
                885                 890                 895

Thr Val Thr Thr Ala Lys Glu Leu Ser Gln Gln Lys Asp Lys Phe Ser
            900                 905                 910

Gln Lys Met Leu Asp Glu Leu Lys Ile Lys Glu Met Ala Leu Glu Thr
            915                 920                 925

Ser Leu Asn Ser Lys Ile Phe Asp Val Thr Ala Ile Asn Ala Asn Ala
        930                 935                 940

Gly Val Leu Lys Asp Cys Ile Glu Lys Arg Gln Leu Leu Lys Lys
945                 950                 955

<210> SEQ ID NO 2
<211> LENGTH: 995
<212> TYPE: PRT
<213> ORGANISM: Streptococcus pyogenes
<220> FEATURE:
<223> OTHER INFORMATION: Streptococcus pyogenes serotype M1 strain AP1
      full-length endoglycosidase EndoS including signal
      peptide

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255
```

```
Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
            275                 280                 285

Leu Ile Glu Arg Gly Ala Pro Tyr Ile Asn Leu Leu Leu Val Gln Val
            290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
            370                 375                 380

Tyr Ala Arg Trp Gln Pro Lys Thr Gly Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
            530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
            610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670
```

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
    770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 3
<211> LENGTH: 3403
<212> TYPE: DNA
<213> ORGANISM: Streptococcus pyogenes
<220> FEATURE:
<223> OTHER INFORMATION: Streptococcus pyogenes serotype M1 strain AP1
      endoglycosidase EndoS

<400> SEQUENCE: 3
ctcttttgtc ctgccatgga tggcaggttg gcaaaaaaat gagaaaagcc taaaaacctt    60
aaatttgtgt tattttacct atactttgta ccttgttttt tttaataaag tgttgttata   120
cttaaggcga actataggaa tgcgcttaca tggatggtat atcaactggg aagccatgac   180

```
ttagtaccaa aaataaggag tgtccaaatg gataaacatt tgttggtaaa aagaacacta    240
gggtgtgttt gtgctgcaac gttgatggga gctgccttag cgacccacca tgattcactc    300
aatactgtaa aagcggagga gaagactgtt caggttcaga aaggattacc ttctatcgat    360
agcttgcatt atctgtcaga gaatagcaaa aaagaattta agaagaact ctcaaaagcg     420 gggcaagaat ctcaaaaggt caaagagata ttagcaaaag ctcagcaggc agataaacaa    480
gctcaagaac ttgccaaaat gaaaattcct gagaaaatac cgatgaaacc gttacatggt    540
cctctctacg gtggttactt tagaacttgg catgacaaaa catcagatcc aacagaaaaa    600
gacaaagtta actcgatggg agagcttcct aaagaagtag atctagcctt tattttccac    660
gattggacaa aagattatag ccttttttgg aaagaattgg ccaccaaaca tgtgccaaag    720
ttaaacaagc aagggacacg tgtcattcgt accattccat ggcgtttcct agctgggggt    780
gataacagtg gtattgcaga agataccagt aaatacccaa atacaccaga gggaaataaa    840
gctttagcca aagctattgt tgatgaatat gtttataaat acaaccttga tggcttagat    900
gtggatgttg aacatgatag tattccaaaa gttgacaaaa aagaagatac agcaggcgta    960
gaacgctcta ttcaagtgtt tgaagaaatt gggaaattaa ttggaccaaa aggtgttgat   1020
aaatcgcggt tatttattat ggatagcacc tacatggctg ataaaaaccc attgattgag   1080
cgaggagctc cttatattaa tttattactg gtacaggtct atggttcaca aggagagaaa   1140
ggtggttggg agcctgtttc taatcgacct gaaaaaacaa tggaagaacg atggcaaggt   1200
tatagcaagt atattcgtcc tgaacaatac atgattggtt tttctttcta tgaggaaaat   1260
gctcaagaag ggaatctttg gtatgatatt aattctcgca aggacgagga caaagcaaat   1320
ggaattaaca ctgacataac tggaacgcgt gccgaacggt atgcaaggtg gcaacctaag   1380
acaggtgggg ttaagggagg tatcttctcc tacgctattg accgagatgg tgtagctcat   1440
caacctaaaa aatatgctaa acagaaagag tttaaggacg caactgataa catcttccac   1500
tcagattata gtgtctccaa ggcattaaag acagttatgc taaagataa gtcgtatgat    1560 ctgattgatg agaaagattt cccagataag gctttgcgag aagctgtgat ggcgcaggtt   1620
ggaaccagaa aaggtgattt ggaacgtttc aatggcacat tacgattgga taatccagcg   1680
attcaaagtt tagaaggtct aaataaattt aaaaaattag ctcaattaga cttgattggc   1740
ttatctcgca ttacaaagct cgaccgttct gttttacccg ctaatatgaa gccaggcaaa   1800
gataccttgg aaacagttct tgaaacctat aaaaaggata caaagaaga acctgctact    1860 atcccaccag tatctttgaa ggtttctggt ttaactggtc tgaaagaatt agatttgtca   1920
ggttttgacc gtgaaacctt ggctggtctt gatgccgcta ctctaacgtc tttagaaaaa   1980
gttgatattt ctggcaacaa acttgatttg ctccaggaa cagaaaatcg acaattttt    2040 gatactatgc tatcaactat cagcaatcat gttggaagca atgaacaaac agtgaaattt   2100
gacaagcaaa aaccaactgg gcattaccca gatacctatg gaaaactag tctgcgctta    2160 ccagtggcaa atgaaaaagt tgatttgcaa agccagcttt tgtttgggac tgtgacaaat   2220
caaggaaccc taatcaatag cgaagcagac tataaggctt accaaaatca taaaattgct   2280
ggacgtagct ttgttgattc aaactatcat tacaataact ttaaagtttc ttatgagaac   2340
tataccgtta aagtaactga ttccacattg ggaaccacta ctgacaaaac gctagcaact   2400
gataaagaag agacctataa ggttgacttc tttagcccag cagataagac aaaagctgtt   2460
catactgcta aagtgattgt tggtgacgaa aaaaccatga tggttaattt ggcagaaggc   2520
```

-continued

```
gcaacagtta ttggaggaag tgctgatcct gtaaatgcaa gaaaggtatt tgatgggcaa    2580
ctgggcagtg agactgataa tatctcttta ggatgggatt ctaagcaaag tattatattt    2640
aaattgaaag aagatggatt aataaagcat ggcgtttct tcaatgattc agcccgaaat     2700
cctgagacaa ccaataaacc tattcaggaa gcaagtctac aaattttaa tatcaaagat     2760 tataatctag ataatttgtt ggaaaatccc aataaatttg atgatgaaaa atattggatt    2820
actgtagata cttacagtgc acaaggagag agagctactg cattcagtaa tacattaaat    2880
aatattacta gtaaatattg gcgagttgtc tttgatacta aaggagatag atatagttcg    2940
ccagtagtcc ctgaactcca aatttttaggt tatccgttac ctaacgccga cactatcatg    3000
aaaacagtaa ctactgctaa agagttatct caacaaaaag ataagttttc tcaaaagatg    3060
cttgatgagt taaaaataaa agagatggct ttagaaactt ctttgaacag taagattttt    3120
gatgtaactg ctattaatgc taatgctgga gttttgaaag attgtattga gaaaaggcag    3180
ctgctaaaaa aataaacaaa gtaactttct tagatagcaa cattcagatt aaattaacaa    3240
aatgtgacta tgataaaggt ttgctggaat tgattaacca aaagactaaa aatctgagat    3300
gaatagtccc agattttag tcttttatag gttttgatga cataaagcta aataatcgtt    3360
agactaccag aaagggcgct tgtccgtgag acatggctgt ctt                       3403
```

<210> SEQ ID NO 4
<211> LENGTH: 995
<212> TYPE: PRT
<213> ORGANISM: Streptococcus pyogenes
<220> FEATURE:
<223> OTHER INFORMATION: Streptococcus pyogenes serotype M1 strain AP1
      full-length endoglycosidase EndoS including signal
      peptide

<400> SEQUENCE: 4

```
Met Asp Lys His Leu Leu Val Lys Arg Thr Leu Gly Cys Val Cys Ala
 1               5                  10                  15

Ala Thr Leu Met Gly Ala Ala Leu Ala Thr His His Asp Ser Leu Asn
             20                  25                  30

Thr Val Lys Ala Glu Glu Lys Thr Val Gln Val Gln Lys Gly Leu Pro
         35                  40                  45

Ser Ile Asp Ser Leu His Tyr Leu Ser Glu Asn Ser Lys Lys Glu Phe
     50                  55                  60

Lys Glu Glu Leu Ser Lys Ala Gly Gln Glu Ser Gln Lys Val Lys Glu
 65                  70                  75                  80

Ile Leu Ala Lys Ala Gln Gln Ala Asp Lys Gln Ala Gln Glu Leu Ala
                 85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
```

```
            195                 200                 205
Gly Asn Lys Ala Leu Ala Lys Ala Ile Val Asp Glu Tyr Val Tyr Lys
    210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620
```

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
            645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
        690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 5
<211> LENGTH: 995
<212> TYPE: PRT
<213> ORGANISM: Streptococcus pyogenes
<220> FEATURE:

<223> OTHER INFORMATION: Streptococcus pyogenes serotype M1 strain SF370
      endoglycosidase
<220> FEATURE:
<221> NAME/KEY: VARIANT
<222> LOCATION: (27)...(27)
<223> OTHER INFORMATION: Xaa = Arg, His, Pro or Leu

<400> SEQUENCE: 5

Met Asp Lys His Leu Leu Val Lys Arg Thr Leu Gly Cys Val Cys Ala
1               5                   10                  15

Ala Thr Leu Met Gly Ala Ala Leu Ala Thr Xaa His Asp Ser Leu Asn
                20                  25                  30

Thr Val Lys Ala Glu Glu Lys Thr Val Gln Val Gln Lys Gly Leu Pro
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Ser
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg

```
              370                 375                 380
Tyr Ala Arg Trp Gln Pro Lys Thr Gly Gly Val Lys Gly Ile Phe
385                 390                 395                 400

Ser Tyr Ala Ile Asp Arg Asp Gly Val Ala His Gln Pro Lys Lys Tyr
                    405                 410                 415

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
        450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                    485                 490                 495

Gly Leu Asn Lys Phe Lys Lys Leu Ala Gln Leu Asp Leu Ile Gly Leu
                500                 505                 510

Ser Arg Ile Thr Lys Leu Asp Arg Ser Val Leu Pro Ala Asn Met Lys
            515                 520                 525

Pro Gly Lys Asp Thr Leu Glu Thr Val Leu Glu Thr Tyr Lys Lys Asp
        530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                    565                 570                 575

Thr Leu Ala Gly Leu Asp Ala Ala Thr Leu Thr Ser Leu Glu Lys Val
                580                 585                 590

Asp Ile Ser Gly Asn Lys Leu Asp Leu Ala Pro Gly Thr Glu Asn Arg
            595                 600                 605

Gln Ile Phe Asp Thr Met Leu Ser Thr Ile Ser Asn His Val Gly Ser
        610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                    645                 650                 655

Lys Val Asp Leu Gln Ser Gln Leu Leu Phe Gly Thr Val Thr Asn Gln
                660                 665                 670

Gly Thr Leu Ile Asn Ser Glu Ala Asp Tyr Lys Ala Tyr Gln Asn His
            675                 680                 685

Lys Ile Ala Gly Arg Ser Phe Val Asp Ser Asn Tyr His Tyr Asn Asn
        690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                    725                 730                 735

Tyr Lys Val Asp Phe Phe Ser Pro Ala Asp Lys Thr Lys Ala Val His
                740                 745                 750

Thr Ala Lys Val Ile Val Gly Asp Glu Lys Thr Met Met Val Asn Leu
            755                 760                 765

Ala Glu Gly Ala Thr Val Ile Gly Gly Ser Ala Asp Pro Val Asn Ala
        770                 775                 780

Arg Lys Val Phe Asp Gly Gln Leu Gly Ser Glu Thr Asp Asn Ile Ser
785                 790                 795                 800
```

-continued

```
Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 6
<211> LENGTH: 999
<212> TYPE: PRT
<213> ORGANISM: Streptococcus pyogenes
<220> FEATURE:
<223> OTHER INFORMATION: Streptococcus pyogenes serotype M1 strain SSI-1
      endoglycosidase

<400> SEQUENCE: 6

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Glu Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Glu Lys Val Pro Glu Lys Val Lys Glu Ile
65                  70                  75                  80

Leu Glu Lys Ala Gln Gln Ala Asp Lys Gln Ala Gln Glu Leu Ala Lys
                85                  90                  95

Met Lys Ile Pro Glu Lys Ile Pro Met Lys Pro Leu His Gly Pro Leu
            100                 105                 110

Tyr Gly Gly Tyr Phe Arg Thr Trp His Asp Lys Thr Ser Asp Pro Thr
        115                 120                 125

Glu Lys Asp Lys Val Asn Ser Met Gly Glu Leu Pro Lys Glu Val Asp
    130                 135                 140

Leu Ala Phe Ile Phe His Asp Trp Thr Lys Asp Tyr Ser Leu Phe Trp
```

-continued

```
               145                 150                 155                 160
        Lys Glu Leu Ala Thr Lys His Val Pro Lys Leu Asn Lys Gln Gly Thr
                            165                 170                 175

Arg Val Ile Arg Thr Ile Pro Trp Arg Phe Leu Ala Gly Gly Asp Asn
                        180                 185                 190

Ser Gly Ile Ala Glu Asp Thr Ser Lys Tyr Pro Asn Thr Pro Glu Gly
                    195                 200                 205

Asn Lys Ala Leu Ala Lys Ala Ile Val Asp Glu Tyr Val Tyr Lys Tyr
                210                 215                 220

Asn Leu Asp Gly Leu Asp Val Asp Val Glu His Asp Ser Ile Pro Lys
        225                 230                 235                 240

Val Asn Gly Lys Ala Ser Asp Glu Asn Leu Lys Arg Ser Ile Asp Val
                            245                 250                 255

Phe Glu Glu Ile Gly Lys Leu Ile Gly Pro Lys Gly Ala Asp Lys Ser
                        260                 265                 270

Arg Leu Phe Ile Met Asp Ser Thr Tyr Met Ala Asp Lys Asn Pro Leu
                    275                 280                 285

Ile Glu Arg Gly Ala Pro Tyr Ile Asp Leu Leu Leu Val Gln Val Tyr
                290                 295                 300

Gly Ser Gln Gly Glu Lys Gly Val Phe Gln Asn Asp Thr Lys Leu Val
        305                 310                 315                 320

Thr Asp Thr Pro Glu Glu Arg Trp Gln Gly Tyr Ser Lys Tyr Ile Arg
                            325                 330                 335

Pro Glu Gln Tyr Met Ile Gly Phe Ser Phe Tyr Glu Glu Arg Ala Gly
                        340                 345                 350

Ser Gly Asn Leu Trp Tyr Asp Ile Asn Ser Arg Lys Asp Glu Asp Lys
                    355                 360                 365

Ala Asn Gly Ile Asn Thr Asp Ile Thr Gly Thr Arg Ala Glu Arg Tyr
                370                 375                 380

Ala Arg Trp Gln Pro Lys Thr Gly Gly Val Lys Gly Gly Ile Phe Ser
        385                 390                 395                 400

Tyr Ala Ile Asp Arg Asp Gly Val Ala His Gln Pro Glu Lys Val Ala
                            405                 410                 415

Gln Gln Asp Lys His Ser Gln Thr Gln Val Asp Glu Ile Thr Asp Asn
                        420                 425                 430

Ile Phe His Ser Asp Tyr Ser Val Ser Lys Ala Leu Lys Thr Val Met
                    435                 440                 445

Leu Lys Asp Lys Ser Tyr Asp Leu Ile Asp Glu Lys Asp Phe Pro Asp
        450                 455                 460

Lys Ala Leu Arg Glu Ala Val Met Ala Gln Val Gly Thr Arg Lys Gly
        465                 470                 475                 480

Asp Leu Glu Arg Phe Asn Gly Thr Leu Arg Leu Asp Asn Pro Ala Ile
                        485                 490                 495

Gln Ser Leu Glu Gly Leu Asn Lys Phe Lys Lys Leu Ala Gln Leu Asp
                    500                 505                 510

Leu Ile Gly Leu Ser Arg Ile Thr Lys Leu Asp Gln Ser Val Leu Pro
                515                 520                 525

Ala Asn Met Lys Pro Gly Lys Asp Thr Leu Glu Thr Val Leu Glu Thr
        530                 535                 540

Tyr Lys Lys Asp Asn Lys Glu Glu Pro Ala Thr Ile Pro Pro Val Ser
        545                 550                 555                 560

Leu Lys Val Ser Gly Leu Thr Gly Leu Lys Ala Leu Asp Leu Ser Gly
                            565                 570                 575
```

-continued

Phe Asp Arg Glu Thr Leu Ala Gly Leu Asp Ala Ala Thr Leu Thr Ser
            580                 585                 590

Leu Glu Lys Val Asp Ile Ser Gly Asn Lys Leu Asp Leu Ala Pro Gly
        595                 600                 605

Thr Glu Asn Arg Gln Ile Phe Asp Thr Met Leu Ser Thr Val Ser Asn
610                 615                 620

His Val Gly Ser Asn Glu Gln Thr Val Lys Phe Asp Lys Gln Lys Pro
625                 630                 635                 640

Thr Gly His Tyr Pro Asp Thr Tyr Gly Lys Thr Ser Leu Arg Leu Pro
                645                 650                 655

Val Ala Asn Glu Lys Val Asp Leu Gln Ser Gln Leu Leu Phe Gly Thr
            660                 665                 670

Val Thr Asn Gln Gly Thr Leu Ile Asn Ser Glu Ala Asp Tyr Lys Ala
        675                 680                 685

Tyr Gln Asn His Lys Ile Ala Gly Arg Ser Phe Val Asp Ser Asn Tyr
690                 695                 700

His Tyr Asn Asn Phe Lys Val Ser Tyr Glu Asn Tyr Thr Val Lys Val
705                 710                 715                 720

Thr Asp Ser Thr Leu Gly Thr Thr Thr Asp Lys Thr Leu Ala Thr Asp
                725                 730                 735

Lys Glu Thr Tyr Lys Val Asp Phe Phe Ser Pro Ala Asp Lys Thr
            740                 745                 750

Lys Ala Val His Thr Ala Lys Val Ile Val Gly Asp Glu Lys Thr Met
        755                 760                 765

Met Val Asn Leu Ala Glu Gly Ala Thr Val Ile Gly Gly Ser Ala Asp
770                 775                 780

Pro Val Asn Ala Arg Lys Val Phe Asp Gly Gln Leu Gly Ser Glu Thr
785                 790                 795                 800

Asp Asn Ile Ser Leu Gly Trp Asp Ser Lys Gln Ser Ile Ile Phe Lys
                805                 810                 815

Leu Lys Glu Asp Gly Leu Ile Lys His Trp Arg Phe Phe Asn Asp Ser
            820                 825                 830

Ala Arg Asn Pro Glu Thr Thr Asn Lys Pro Ile Gln Glu Ala Ser Leu
        835                 840                 845

Gln Ile Phe Asn Ile Lys Asp Tyr Asn Leu Asp Asn Leu Leu Glu Asn
850                 855                 860

Pro Asn Lys Phe Asp Asp Glu Lys Tyr Trp Ile Thr Val Asp Thr Tyr
865                 870                 875                 880

Ser Ala Gln Gly Glu Arg Ala Thr Ala Phe Ser Asn Thr Leu Asn Asn
                885                 890                 895

Ile Thr Ser Lys Tyr Trp Arg Val Val Phe Asp Thr Lys Gly Asp Arg
            900                 905                 910

Tyr Ser Ser Pro Val Val Pro Glu Leu Gln Ile Leu Gly Tyr Pro Leu
        915                 920                 925

Pro Asn Ala Asp Thr Ile Met Lys Thr Val Thr Thr Ala Lys Gly Leu
930                 935                 940

Ser Gln Gln Lys Asp Lys Phe Ser Gln Lys Met Leu Asp Glu Leu Lys
945                 950                 955                 960

Ile Lys Glu Met Ala Leu Glu Thr Ser Leu Asn Ser Lys Ile Phe Asp
                965                 970                 975

Val Thr Ala Ile Asn Ala Asn Ala Gly Val Leu Lys Asp Cys Ile Glu
            980                 985                 990

```
Lys Arg Gln Leu Leu Lys Lys
        995

<210> SEQ ID NO 7
<211> LENGTH: 995
<212> TYPE: PRT
<213> ORGANISM: Streptococcus pyogenes
<220> FEATURE:
<223> OTHER INFORMATION: Streptococcus pyogenes serotype M1 strain
      MGAS5005 endoglycosidase

<400> SEQUENCE: 7

Met Asp Lys His Leu Leu Val Lys Arg Thr Leu Gly Cys Val Cys Ala
 1               5                  10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Asp Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350
```

Gln Glu Gly Asn Leu Trp Tyr Asp Ile Asn Ser Arg Lys Asp Glu Asp
            355                 360                 365
Lys Ala Asn Gly Ile Asn Thr Asp Ile Thr Gly Thr Arg Ala Glu Arg
        370                 375                 380
Tyr Ala Arg Trp Gln Pro Lys Thr Gly Val Lys Gly Gly Ile Phe
385                 390                 395                 400
Ser Tyr Ala Ile Asp Arg Asp Gly Val Ala His Gln Pro Lys Lys Tyr
                405                 410                 415
Ala Lys Gln Lys Glu Phe Lys Asp Ala Thr Asp Asn Ile Phe His Ser
            420                 425                 430
Asp Tyr Ser Val Ser Lys Ala Leu Lys Thr Val Met Leu Lys Asp Lys
            435                 440                 445
Ser Tyr Asp Leu Ile Asp Glu Lys Asp Phe Pro Asp Lys Ala Leu Arg
        450                 455                 460
Glu Ala Val Met Ala Gln Val Gly Thr Arg Lys Gly Asp Leu Glu Arg
465                 470                 475                 480
Phe Asn Gly Thr Leu Arg Leu Asp Asn Pro Ala Ile Gln Ser Leu Glu
                485                 490                 495
Gly Leu Asn Lys Phe Lys Lys Leu Ala Gln Leu Asp Leu Ile Gly Leu
            500                 505                 510
Ser Arg Ile Thr Lys Leu Asp Arg Ser Val Leu Pro Ala Asn Met Lys
            515                 520                 525
Pro Gly Lys Asp Thr Leu Glu Thr Val Leu Glu Thr Tyr Lys Lys Asp
        530                 535                 540
Asn Lys Glu Glu Pro Ala Thr Ile Pro Pro Val Ser Leu Lys Val Ser
545                 550                 555                 560
Gly Leu Thr Gly Leu Lys Glu Leu Asp Leu Ser Gly Phe Asp Arg Glu
                565                 570                 575
Thr Leu Ala Gly Leu Asp Ala Ala Thr Leu Thr Ser Leu Glu Lys Val
            580                 585                 590
Asp Ile Ser Gly Asn Lys Leu Asp Leu Ala Pro Gly Thr Glu Asn Arg
            595                 600                 605
Gln Ile Phe Asp Thr Met Leu Ser Thr Ile Ser Asn His Val Gly Ser
        610                 615                 620
Asn Glu Gln Thr Val Lys Phe Asp Lys Gln Lys Pro Thr Gly His Tyr
625                 630                 635                 640
Pro Asp Thr Tyr Gly Lys Thr Ser Leu Arg Leu Pro Val Ala Asn Glu
                645                 650                 655
Lys Val Asp Leu Gln Ser Gln Leu Leu Phe Gly Thr Val Thr Asn Gln
            660                 665                 670
Gly Thr Leu Ile Asn Ser Glu Ala Asp Tyr Lys Ala Tyr Gln Asn His
            675                 680                 685
Lys Ile Ala Gly Arg Ser Phe Val Asp Ser Asn Tyr His Tyr Asn Asn
        690                 695                 700
Phe Lys Val Ser Tyr Glu Asn Tyr Thr Val Lys Val Thr Asp Ser Thr
705                 710                 715                 720
Leu Gly Thr Thr Thr Asp Lys Thr Leu Ala Thr Asp Lys Glu Glu Thr
                725                 730                 735
Tyr Lys Val Asp Phe Phe Ser Pro Ala Asp Lys Thr Lys Ala Val His
            740                 745                 750
Thr Ala Lys Val Ile Val Gly Asp Glu Lys Thr Met Met Val Asn Leu
            755                 760                 765

```
Ala Glu Gly Ala Thr Val Ile Gly Gly Ser Ala Asp Pro Val Asn Ala
770             775                 780

Arg Lys Val Phe Asp Gly Gln Leu Gly Ser Glu Thr Asp Asn Ile Ser
785             790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
                820                 825                 830

Glu Thr Thr Asn Lys Pro Ile Gln Glu Ala Ser Leu Gln Ile Phe Asn
                835                 840                 845

Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
                915                 920                 925

Thr Ile Met Lys Thr Val Thr Thr Ala Lys Glu Leu Ser Gln Gln Lys
                930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
                980                 985                 990

Leu Lys Lys
        995

<210> SEQ ID NO 8
<211> LENGTH: 1021
<212> TYPE: PRT
<213> ORGANISM: Streptococcus pyogenes
<220> FEATURE:
<223> OTHER INFORMATION: Streptococcus pyogenes serotype M2 strain
      MGAS10270 endoglycosidase

<400> SEQUENCE: 8

Met Val Tyr Gln Leu Gly Ser His Asp Leu Val Pro Lys Ile Arg Ser
1               5                   10                  15

Val Gln Met Asp Lys His Leu Leu Val Lys Arg Thr Leu Gly Cys Val
                20                  25                  30

Cys Ala Ala Thr Leu Met Gly Ala Ala Leu Ala Thr His His Asp Ser
                35                  40                  45

Leu Asn Thr Val Lys Ala Glu Glu Lys Thr Val Gln Val Gln Lys Glu
                50                  55                  60

Leu Ser Ser Ile Asp Ser Leu His Tyr Leu Ser Glu Asn Ser Lys Lys
65                  70                  75                  80

Glu Phe Lys Glu Glu Leu Ser Lys Glu Lys Val Pro Glu Lys Val Lys
                85                  90                  95

Glu Ile Leu Ala Lys Ala Gln Gln Ala Asp Lys Gln Ala Gln Glu Leu
                100                 105                 110

Thr Lys Met Lys Ile Pro Glu Lys Ile Pro Met Lys Pro Leu His Gly
                115                 120                 125
```

```
Pro Leu Tyr Gly Gly Tyr Phe Arg Thr Trp His Asp Lys Thr Ser Asp
    130                 135                 140

Pro Thr Glu Lys Asp Lys Val Asn Ser Met Gly Glu Leu Pro Lys Glu
145                 150                 155                 160

Val Asp Leu Ala Phe Ile Phe His Asp Trp Thr Lys Asp Tyr Ser Leu
                165                 170                 175

Phe Trp Lys Glu Leu Ala Thr Lys His Val Pro Lys Leu Asn Lys Gln
            180                 185                 190

Gly Thr Arg Val Ile Arg Thr Ile Pro Trp Arg Phe Leu Ala Gly Gly
        195                 200                 205

Asp Asn Ser Gly Ile Ala Glu Asp Ala Ser Lys Tyr Pro Asn Thr Pro
    210                 215                 220

Glu Gly Asn Lys Ala Leu Ala Lys Ala Ile Val Asp Glu Tyr Val Tyr
225                 230                 235                 240

Lys Tyr Asn Leu Asp Gly Leu Asp Val Asp Val Glu His Asp Ser Ile
                245                 250                 255

Pro Lys Val Asn Gly Glu Ala Ser Asp Glu Asn Leu Lys Arg Ser Ile
            260                 265                 270

Asp Val Phe Glu Glu Ile Gly Lys Leu Ile Gly Pro Lys Gly Ala Asp
        275                 280                 285

Lys Ser Arg Leu Phe Ile Met Asp Ser Thr Tyr Met Ala Asp Lys Asn
    290                 295                 300

Pro Leu Ile Glu Arg Gly Ala Pro Tyr Ile Asp Leu Leu Leu Val Gln
305                 310                 315                 320

Val Tyr Gly Ala Arg Gly Glu Gln Gly Glu Phe Gln Asn Asp Thr Lys
                325                 330                 335

Leu Val Thr Glu Thr Pro Glu Glu Arg Trp Gln Gly Tyr Ser Lys Tyr
            340                 345                 350

Ile Arg Pro Glu Gln Tyr Met Ile Gly Phe Ser Phe Tyr Glu Glu Arg
        355                 360                 365

Ala Gly Ser Gly Asn Leu Trp Tyr Asp Ile Asn Ser Arg Lys Asp Glu
    370                 375                 380

Asp Thr Ala Asn Gly Ile Asn Thr Asp Ile Thr Gly Thr Arg Ala Glu
385                 390                 395                 400

Arg Tyr Ala Arg Trp Gln Pro Lys Thr Gly Gly Ile Lys Gly Gly Ile
                405                 410                 415

Phe Ser Tyr Ala Ile Asp Arg Asp Gly Val Ala His Gln Pro Lys Gln
            420                 425                 430

Ile Ala Glu Lys Asp Lys Gln Asn Val Lys Asn Asn Gln Pro Gln Ile
        435                 440                 445

Pro Glu Ile Thr Asp Asn Ile Phe His Ser Asp Tyr Ser Val Ser Lys
    450                 455                 460

Ala Leu Lys Thr Val Met Leu Lys Asp Lys Ser Tyr Asp Leu Ile Asp
465                 470                 475                 480

Glu Lys Asp Phe Pro Asp Lys Ala Leu Arg Glu Ala Val Met Ala Gln
                485                 490                 495

Val Gly Thr Arg Lys Gly Asp Leu Glu Arg Phe Asn Gly Thr Leu Arg
            500                 505                 510

Leu Asp Asn Pro Ala Ile Gln Ser Leu Glu Gly Leu Asn Lys Phe Lys
        515                 520                 525

Lys Leu Ala Gln Leu Asp Leu Ile Gly Leu Ser Arg Ile Thr Lys Leu
    530                 535                 540
```

```
Asp Arg Ser Val Leu Pro Ala Asn Met Lys Pro Gly Lys Asp Thr Leu
545                 550                 555                 560

Glu Thr Val Leu Glu Thr Tyr Lys Lys Asp Asn Lys Glu Glu Pro Ala
                565                 570                 575

Thr Ile Pro Pro Val Ser Leu Lys Val Ser Gly Leu Thr Gly Leu Lys
            580                 585                 590

Glu Leu Asp Leu Ser Gly Phe Asp Arg Glu Thr Leu Ala Gly Leu Asp
        595                 600                 605

Ala Ala Thr Leu Thr Ser Leu Glu Lys Val Asp Ile Ser Gly Asn Lys
    610                 615                 620

Leu Asp Leu Ala Pro Gly Thr Glu Asn Arg Gln Ile Phe Asp Thr Met
625                 630                 635                 640

Leu Ser Thr Val Ser Asn His Val Gly Ser Asn Glu Gln Thr Val Lys
                645                 650                 655

Phe Asp Lys Gln Lys Pro Thr Gly His Tyr Pro Asp Thr Tyr Gly Lys
            660                 665                 670

Thr Ser Leu Arg Leu Pro Val Ala Glu Gly Asn Ile Asp Leu Gln Ser
        675                 680                 685

Gln Leu Leu Phe Gly Thr Val Thr Asn Gln Gly Thr Leu Ile Asn Ser
    690                 695                 700

Glu Ala Asp Tyr Lys Ala Tyr Gln Asn His Lys Ile Ala Gly Arg Ser
705                 710                 715                 720

Phe Val Asp Ser Asn Tyr His Tyr Ser Asn Phe Lys Val Ser Tyr Glu
                725                 730                 735

Asn Tyr Thr Val Lys Val Thr Asp Ser Thr Leu Gly Thr Thr Thr Asp
            740                 745                 750

Lys Thr Leu Ala Thr Asp Lys Glu Glu Thr Tyr Lys Val Asp Phe Phe
        755                 760                 765

Ser Pro Ala Asp Lys Thr Lys Ala Ile His Thr Ala Lys Val Ile Val
    770                 775                 780

Gly Asp Glu Lys Thr Met Met Val Asn Leu Ala Ala Gly Ala Thr Val
785                 790                 795                 800

Ile Gly Gly Ser Ala Asp Lys Glu Met Ser Arg Asn Val Phe Asp Gly
                805                 810                 815

Ser Leu Gly Gly Asp Arg Ser Asn Leu Leu Gly Met Ser Gly Pro Lys
            820                 825                 830

Ser Thr Ile Ile Phe Asn Leu Lys Glu Ser Gly Ile Val Lys His Trp
        835                 840                 845

Arg Phe Phe Asn Asp Arg Ala Arg Ser Pro Gln Asn Pro Ala Glu Asp
850                 855                 860

Ile Gln Glu Ile Lys Leu Gln Val Phe Asp Ser Glu Lys Tyr Asp Ile
865                 870                 875                 880

Glu Thr Leu Leu Lys Thr Pro Asn Gln Phe Asp Lys Asp Tyr Trp
                885                 890                 895

Ile Thr Val Asp Ser Tyr Lys Ser Lys Ser Glu Thr Val Asn Asn Tyr
            900                 905                 910

Asp Gln Val Leu Lys Met Asn Ser Ala Lys Tyr Trp Arg Val Thr Val
        915                 920                 925

Asp Thr Lys Gly Gly Asn Tyr Ser Trp Pro Ser Leu Pro Glu Leu Gln
    930                 935                 940

Ile Leu Gly Tyr Pro Leu Pro Asn Ala Asp Thr Ile Met Lys Thr Val
945                 950                 955                 960

Thr Thr Ala Lys Gly Leu Ser Gln Gln Lys Asp Lys Phe Ser Gln Lys
```

```
              965                 970                 975
Met Leu Asp Glu Leu Lys Ile Lys Glu Met Ala Leu Glu Thr Ser Leu
            980                 985                 990

Asn Ser Lys Ile Phe Asp Val Thr Ala Ile Asn Ala Asn Ala Gly Val
            995                1000                1005

Leu Lys Asp Cys Ile Glu Lys Arg Gln Leu Leu Lys Lys
           1010                1015                1020

<210> SEQ ID NO 9
<211> LENGTH: 999
<212> TYPE: PRT
<213> ORGANISM: Streptococcus pyogenes
<220> FEATURE:
<223> OTHER INFORMATION: Streptococcus pyogenes serotype M3 strain
      MGAS315 endoglycosidase

<400> SEQUENCE: 9

Met Asp Lys His Leu Leu Val Lys Arg Thr Leu Gly Cys Val Cys Ala
  1               5                  10                  15

Ala Thr Leu Met Gly Ala Ala Leu Ala Thr His His Asp Ser Leu Asn
             20                  25                  30

Thr Val Lys Ala Glu Glu Lys Thr Val Gln Val Gln Lys Glu Leu Pro
         35                  40                  45

Ser Ile Asp Ser Leu His Tyr Leu Ser Glu Asn Ser Lys Lys Glu Phe
     50                  55                  60

Lys Glu Glu Leu Ser Lys Glu Lys Val Pro Glu Lys Val Lys Glu Ile
 65                  70                  75                  80

Leu Glu Lys Ala Gln Gln Ala Asp Lys Gln Ala Gln Glu Leu Ala Lys
                 85                  90                  95

Met Lys Ile Pro Glu Lys Ile Pro Met Lys Pro Leu His Gly Pro Leu
            100                 105                 110

Tyr Gly Gly Tyr Phe Arg Thr Trp His Asp Lys Thr Ser Asp Pro Thr
        115                 120                 125

Glu Lys Asp Lys Val Asn Ser Met Gly Glu Leu Pro Lys Glu Val Asp
    130                 135                 140

Leu Ala Phe Ile Phe His Asp Trp Thr Lys Asp Tyr Ser Leu Phe Trp
145                 150                 155                 160

Lys Glu Leu Ala Thr Lys His Val Pro Lys Leu Asn Lys Gln Gly Thr
                165                 170                 175

Arg Val Ile Arg Thr Ile Pro Trp Arg Phe Leu Ala Gly Gly Asp Asn
            180                 185                 190

Ser Gly Ile Ala Glu Asp Thr Ser Lys Tyr Pro Asn Thr Pro Glu Gly
        195                 200                 205

Asn Lys Ala Leu Ala Lys Ala Ile Val Asp Glu Tyr Val Tyr Lys Tyr
    210                 215                 220

Asn Leu Asp Gly Leu Asp Val Asp Val Glu His Asp Ser Ile Pro Lys
225                 230                 235                 240

Val Asn Gly Lys Ala Ser Asp Glu Asn Leu Lys Arg Ser Ile Asp Val
                245                 250                 255

Phe Glu Glu Ile Gly Lys Leu Ile Gly Pro Lys Gly Ala Asp Lys Ser
            260                 265                 270

Arg Leu Phe Ile Met Asp Ser Thr Tyr Met Ala Asp Lys Asn Pro Leu
        275                 280                 285

Ile Glu Arg Gly Ala Pro Tyr Ile Asp Leu Leu Leu Val Gln Val Tyr
    290                 295                 300
```

```
Gly Ser Gln Gly Glu Lys Gly Val Phe Gln Asn Asp Thr Lys Leu Val
305                 310                 315                 320

Thr Asp Thr Pro Glu Glu Arg Trp Gln Gly Tyr Ser Lys Tyr Ile Arg
            325                 330                 335

Pro Glu Gln Tyr Met Ile Gly Phe Ser Phe Tyr Glu Arg Ala Gly
            340                 345                 350

Ser Gly Asn Leu Trp Tyr Asp Ile Asn Ser Arg Lys Asp Glu Asp Lys
            355                 360                 365

Ala Asn Gly Ile Asn Thr Asp Ile Thr Gly Thr Arg Ala Glu Arg Tyr
370                 375                 380

Ala Arg Trp Gln Pro Lys Thr Gly Val Lys Gly Ile Phe Ser
385                 390                 395                 400

Tyr Ala Ile Asp Arg Asp Gly Val Ala His Gln Pro Glu Lys Val Ala
                405                 410                 415

Gln Gln Asp Lys His Ser Gln Thr Gln Val Asp Glu Ile Thr Asp Asn
            420                 425                 430

Ile Phe His Ser Asp Tyr Ser Val Ser Lys Ala Leu Lys Thr Val Met
        435                 440                 445

Leu Lys Asp Lys Ser Tyr Asp Leu Ile Asp Glu Lys Asp Phe Pro Asp
450                 455                 460

Lys Ala Leu Arg Glu Ala Val Met Ala Gln Val Gly Thr Arg Lys Gly
465                 470                 475                 480

Asp Leu Glu Arg Phe Asn Gly Thr Leu Arg Leu Asp Asn Pro Ala Ile
                485                 490                 495

Gln Ser Leu Glu Gly Leu Asn Lys Phe Lys Lys Leu Ala Gln Leu Asp
            500                 505                 510

Leu Ile Gly Leu Ser Arg Ile Thr Lys Leu Asp Gln Ser Val Leu Pro
        515                 520                 525

Ala Asn Met Lys Pro Gly Lys Asp Thr Leu Glu Thr Val Leu Glu Thr
530                 535                 540

Tyr Lys Lys Asp Asn Lys Glu Glu Pro Ala Thr Ile Pro Pro Val Ser
545                 550                 555                 560

Leu Lys Val Ser Gly Leu Thr Gly Leu Lys Ala Leu Asp Leu Ser Gly
                565                 570                 575

Phe Asp Arg Glu Thr Leu Ala Gly Leu Asp Ala Ala Thr Leu Thr Ser
            580                 585                 590

Leu Glu Lys Val Asp Ile Ser Gly Asn Lys Leu Asp Leu Ala Pro Gly
        595                 600                 605

Thr Glu Asn Arg Gln Ile Phe Asp Thr Met Leu Ser Thr Val Ser Asn
610                 615                 620

His Val Gly Ser Asn Glu Gln Thr Val Lys Phe Asp Lys Gln Lys Pro
625                 630                 635                 640

Thr Gly His Tyr Pro Asp Thr Tyr Gly Lys Thr Ser Leu Arg Leu Pro
                645                 650                 655

Val Ala Asn Glu Lys Val Asp Leu Gln Ser Gln Leu Leu Phe Gly Thr
            660                 665                 670

Val Thr Asn Gln Gly Thr Leu Ile Asn Ser Glu Ala Asp Tyr Lys Ala
        675                 680                 685

Tyr Gln Asn His Lys Ile Ala Gly Arg Ser Phe Val Asp Ser Asn Tyr
            690                 695                 700

His Tyr Asn Asn Phe Lys Val Ser Tyr Glu Asn Tyr Thr Val Lys Val
705                 710                 715                 720

Thr Asp Ser Thr Leu Gly Thr Thr Thr Asp Lys Thr Leu Ala Thr Asp
```

```
            725                 730                 735
Lys Glu Glu Thr Tyr Lys Val Asp Phe Phe Ser Pro Ala Asp Lys Thr
            740                 745                 750

Lys Ala Val His Thr Ala Lys Val Ile Val Gly Asp Glu Lys Thr Met
            755                 760                 765

Met Val Asn Leu Ala Glu Gly Ala Thr Val Ile Gly Gly Ser Ala Asp
            770                 775                 780

Pro Val Asn Ala Arg Lys Val Phe Asp Gly Gln Leu Gly Ser Glu Thr
785                 790                 795                 800

Asp Asn Ile Ser Leu Gly Trp Asp Ser Lys Gln Ser Ile Ile Phe Lys
                805                 810                 815

Leu Lys Glu Asp Gly Leu Ile Lys His Trp Arg Phe Phe Asn Asp Ser
            820                 825                 830

Ala Arg Asn Pro Glu Thr Thr Asn Lys Pro Ile Gln Glu Ala Ser Leu
            835                 840                 845

Gln Ile Phe Asn Ile Lys Asp Tyr Asn Leu Asp Asn Leu Leu Glu Asn
        850                 855                 860

Pro Asn Lys Phe Asp Asp Glu Lys Tyr Trp Ile Thr Val Asp Thr Tyr
865                 870                 875                 880

Ser Ala Gln Gly Glu Arg Ala Thr Ala Phe Ser Asn Thr Leu Asn Asn
                885                 890                 895

Ile Thr Ser Lys Tyr Trp Arg Val Val Phe Asp Thr Lys Gly Asp Arg
            900                 905                 910

Tyr Ser Ser Pro Val Val Pro Glu Leu Gln Ile Leu Gly Tyr Pro Leu
        915                 920                 925

Pro Asn Ala Asp Thr Ile Met Lys Thr Val Thr Thr Ala Lys Gly Leu
930                 935                 940

Ser Gln Gln Lys Asp Lys Phe Ser Gln Lys Met Leu Asp Glu Leu Lys
945                 950                 955                 960

Ile Lys Glu Met Ala Leu Glu Thr Ser Leu Asn Ser Lys Ile Phe Asp
                965                 970                 975

Val Thr Ala Ile Asn Ala Asn Ala Gly Val Leu Lys Asp Cys Ile Glu
            980                 985                 990

Lys Arg Gln Leu Leu Lys Lys
            995

<210> SEQ ID NO 10
<211> LENGTH: 1022
<212> TYPE: PRT
<213> ORGANISM: Streptococcus pyogenes
<220> FEATURE:
<223> OTHER INFORMATION: Streptococcus pyogenes serotype M4 strain
      MGAS10750 endoglycosidase

<400> SEQUENCE: 10

Met Val Tyr Gln Leu Gly Ser His Asp Leu Val Pro Lys Ile Arg Ser
1               5                   10                  15

Val Gln Met Asp Lys His Leu Leu Val Lys Arg Thr Leu Gly Cys Val
            20                  25                  30

Cys Ala Ala Thr Leu Met Gly Ala Ala Leu Ala Thr His His Asp Ser
        35                  40                  45

Leu Asn Thr Val Lys Ala Glu Glu Lys Thr Val Gln Val Gln Lys Glu
    50                  55                  60

Leu Ser Ser Ile Asp Ser Leu His Tyr Leu Ser Glu Asn Ser Lys Lys
65              70                  75                  80
```

-continued

```
Glu Phe Lys Glu Glu Leu Ser Lys Ala Gly Gln Glu Ser Gln Lys Val
                 85                  90                  95
Lys Glu Ile Leu Ala Lys Ala Gln Gln Ala Asp Lys Gln Ala Gln Glu
            100                 105                 110
Leu Ala Lys Met Lys Ile Pro Glu Lys Ile Leu Met Lys Pro Leu His
        115                 120                 125
Gly Pro Leu Tyr Gly Tyr Phe Arg Thr Trp His Asp Lys Thr Ser
    130                 135                 140
Asp Pro Thr Glu Lys Asp Lys Val Asn Ser Met Gly Glu Leu Pro Lys
145                 150                 155                 160
Glu Val Asp Leu Ala Phe Ile Phe His Asp Trp Thr Lys Asp Tyr Ser
                165                 170                 175
Leu Phe Trp Lys Glu Leu Ala Thr Lys His Val Pro Lys Leu Asn Lys
            180                 185                 190
Gln Gly Thr Arg Val Ile Arg Thr Ile Pro Trp Arg Phe Leu Ala Gly
        195                 200                 205
Gly Asp Asn Ser Gly Ile Ala Glu Asp Thr Ser Lys Tyr Pro Asn Thr
    210                 215                 220
Pro Glu Gly Asn Lys Ala Leu Ala Lys Ala Ile Val Asp Glu Tyr Val
225                 230                 235                 240
Tyr Lys Tyr Asn Leu Asp Gly Leu Asp Val Asp Val Glu His Asp Ser
                245                 250                 255
Ile Pro Lys Val Asn Gly Glu Ala Ser Asp Glu Asn Leu Lys Arg Ser
            260                 265                 270
Ile Asp Val Phe Glu Glu Ile Gly Lys Leu Ile Gly Pro Lys Gly Val
        275                 280                 285
Asp Lys Ser Arg Leu Phe Ile Met Asp Ser Thr Tyr Met Ala Asp Lys
    290                 295                 300
Asn Pro Leu Ile Glu Arg Gly Ala Pro Tyr Ile Asp Leu Leu Leu Val
305                 310                 315                 320
Gln Val Tyr Gly Ala Arg Gly Glu Gln Gly Glu Phe Gln Asn Asp Thr
                325                 330                 335
Lys Leu Val Thr Glu Thr Pro Glu Glu Arg Trp Gln Gly Tyr Ser Lys
            340                 345                 350
Tyr Ile Arg Pro Glu Gln Tyr Met Ile Gly Phe Ser Phe Tyr Glu Glu
        355                 360                 365
Arg Ala Gly Ser Gly Asn Leu Trp Tyr Asp Ile Asn Ser Arg Lys Asp
    370                 375                 380
Asp Asp Lys Ala Asn Gly Ile Asn Thr Asp Ile Thr Gly Thr Arg Ala
385                 390                 395                 400
Glu Arg Tyr Ala Arg Trp Gln Pro Lys Thr Gly Gly Val Lys Gly Gly
                405                 410                 415
Ile Phe Ser Tyr Ala Ile Asp Arg Asp Gly Val Ala His Gln Pro Lys
            420                 425                 430
Gln Ile Ala Glu Lys Asp Lys Gln Asn Val Lys Asn Asn Gln Pro Gln
        435                 440                 445
Ile Pro Glu Ile Thr Asp Asn Ile Phe His Ser Asp Tyr Ser Val Ser
    450                 455                 460
Lys Ala Leu Lys Thr Val Met Leu Lys Asp Lys Ser Tyr Asp Leu Ile
465                 470                 475                 480
Asp Glu Lys Asp Phe Pro Asp Lys Ala Leu Arg Glu Ala Val Met Ala
                485                 490                 495
Gln Val Gly Thr Arg Lys Gly Asp Leu Glu Arg Phe Asn Gly Thr Leu
```

-continued

```
                500                 505                 510
Arg Leu Asp Asn Pro Ala Ile Gln Ser Leu Glu Gly Leu Asn Lys Phe
            515                 520                 525
Lys Lys Leu Ala Gln Leu Asp Leu Ile Gly Leu Ser Cys Ile Thr Lys
            530                 535                 540
Leu Asp Gln Ser Val Leu Pro Ala Asn Met Lys Pro Gly Lys Asp Thr
545                 550                 555                 560
Leu Glu Thr Val Leu Glu Thr Tyr Lys Lys Asp Asn Lys Glu Pro
                565                 570                 575
Ala Thr Ile Pro Pro Val Ser Leu Lys Val Ser Gly Leu Thr Gly Leu
                580                 585                 590
Lys Glu Leu Asp Leu Ser Gly Phe Asp Arg Glu Thr Leu Ala Gly Leu
            595                 600                 605
Asp Ala Ala Thr Leu Thr Ser Leu Glu Lys Val Asp Ile Ser Gly Asn
            610                 615                 620
Lys Leu Asp Leu Ala Pro Gly Thr Glu Asn Arg Gln Ile Phe Asp Thr
625                 630                 635                 640
Met Leu Ser Ile Ile Ser Asn His Val Gly Ser Asn Glu Gln Thr Val
                645                 650                 655
Lys Phe Asp Lys Gln Lys Pro Thr Gly His Tyr Pro Asp Thr Tyr Gly
            660                 665                 670
Lys Thr Ser Leu Arg Leu Pro Val Ala Asn Glu Lys Val Asp Leu Gln
            675                 680                 685
Ser Gln Leu Leu Phe Gly Thr Val Thr Asn Gln Gly Thr Leu Ile Asn
            690                 695                 700
Ser Glu Ala Asp Tyr Lys Ala Tyr Gln Asn His Lys Ile Ala Gly Arg
705                 710                 715                 720
Ser Phe Val Asp Ser Asn Tyr His Tyr Asn Asn Phe Lys Val Ser Tyr
                725                 730                 735
Glu Asn Tyr Thr Val Lys Val Thr Asp Ser Thr Leu Gly Thr Thr Thr
                740                 745                 750
Asp Lys Thr Leu Ala Thr Asp Lys Glu Glu Thr Tyr Lys Val Asp Phe
            755                 760                 765
Phe Ser Pro Ala Asp Lys Thr Lys Ala Val His Thr Ala Lys Val Ile
            770                 775                 780
Val Gly Asp Glu Lys Thr Met Met Val Asn Leu Ala Glu Gly Ala Thr
785                 790                 795                 800
Val Ile Gly Gly Ser Ala Asp Pro Val Asn Ala Arg Lys Val Phe Asp
                805                 810                 815
Gly Gln Leu Gly Ser Glu Thr Asp Asn Ile Ser Leu Gly Trp Asp Ser
                820                 825                 830
Lys Gln Ser Ile Ile Phe Lys Leu Lys Glu Asp Gly Leu Ile Lys His
            835                 840                 845
Trp Arg Phe Phe Asn Asp Ser Ala Arg Asn Pro Glu Thr Thr Asn Lys
            850                 855                 860
Pro Ile Gln Glu Ala Ser Leu Gln Ile Phe Asn Ile Lys Asp Tyr Asn
865                 870                 875                 880
Leu Asp Asn Leu Leu Glu Asn Pro Asn Lys Phe Asp Asp Glu Lys Tyr
                885                 890                 895
Trp Ile Thr Val Asp Thr Tyr Ser Ala Gln Gly Glu Arg Ala Thr Ala
                900                 905                 910
Phe Ser Asn Thr Leu Asn Asn Ile Thr Ser Lys Tyr Trp Arg Val Val
            915                 920                 925
```

Phe Asp Thr Lys Gly Asp Arg Tyr Ser Ser Pro Val Val Pro Glu Leu
                930                 935                 940

Gln Ile Leu Gly Tyr Pro Leu Pro Asn Ala Asp Thr Ile Met Lys Thr
945                 950                 955                 960

Val Thr Thr Ala Lys Glu Leu Ser Gln Gln Lys Asp Lys Phe Ser Gln
                965                 970                 975

Lys Met Leu Asp Glu Leu Lys Ile Lys Glu Met Ala Leu Glu Thr Ser
                980                 985                 990

Leu Asn Ser Lys Ile Phe Asp Val Thr Ala Ile Asn Ala Asn Ala Gly
            995                1000                1005

Val Leu Lys Asp Cys Ile Glu Lys Arg Gln Leu Leu Lys Lys
       1010                1015                1020

<210> SEQ ID NO 11
<211> LENGTH: 990
<212> TYPE: PRT
<213> ORGANISM: Streptococcus pyogenes
<220> FEATURE:
<223> OTHER INFORMATION: Streptococcus pyogenes serotype M5 strain
      Manfredo endoglycosidase

<400> SEQUENCE: 11

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Glu Leu Ser
            35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
            115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
            195                 200                 205

Gly Asn Lys Ala Leu Ala Lys Ala Ile Val Asp Glu Tyr Val Tyr Lys
        210                 215                 220

Tyr Asn Leu Asp Gly Leu Asp Val Asp Val Glu His Asp Ser Ile Pro
225                 230                 235                 240

Lys Val Asn Gly Glu Ala Ser Asp Glu Asn Leu Lys Arg Ser Ile Asp
                245                 250                 255

Val Phe Glu Glu Ile Gly Lys Leu Ile Gly Pro Lys Gly Val Asp Lys

```
            260                 265                 270
Ser Arg Leu Phe Ile Met Asp Ser Thr Tyr Met Ala Asp Lys Asn Pro
            275                 280                 285

Leu Ile Glu Arg Gly Ala Pro Tyr Ile Asp Leu Leu Leu Val Gln Val
        290                 295                 300

Tyr Gly Ala Arg Gly Glu Gln Gly Glu Phe Gln Asn Asp Thr Lys Leu
305                 310                 315                 320

Val Thr Glu Thr Pro Glu Glu Arg Trp Gln Gly Tyr Ser Lys Tyr Ile
                325                 330                 335

Arg Pro Glu Gln Tyr Met Ile Gly Phe Ser Phe Tyr Glu Glu Arg Ala
                340                 345                 350

Gly Ser Gly Asn Leu Trp Tyr Asp Ile Asn Ser Arg Lys Asp Glu Asp
            355                 360                 365

Thr Ala Asn Gly Ile Asn Thr Asp Ile Thr Gly Thr Arg Ala Glu Arg
            370                 375                 380

Tyr Ala Arg Trp Gln Pro Lys Thr Gly Gly Ile Lys Gly Gly Ile Phe
385                 390                 395                 400

Ser Tyr Ala Ile Asp Arg Asp Gly Val Ala His Gln Pro Lys Gln Ile
                405                 410                 415

Ala Glu Lys Asp Lys Gln Asn Val Lys Asn Asn Gln Pro Gln Ile Pro
                420                 425                 430

Glu Ile Thr Asp Asn Ile Phe His Ser Asp Tyr Ser Val Ser Lys Ala
            435                 440                 445

Leu Lys Thr Val Met Leu Lys Asp Lys Ser Tyr Asp Leu Ile Asp Glu
450                 455                 460

Lys Asp Phe Pro Asp Lys Ala Leu Arg Glu Ala Val Met Ala Gln Val
465                 470                 475                 480

Gly Thr Arg Lys Gly Asp Leu Glu Arg Phe Asn Gly Thr Leu Arg Leu
                485                 490                 495

Asp Asn Pro Ala Ile Gln Ser Leu Glu Gly Leu Asn Lys Phe Lys Lys
            500                 505                 510

Leu Ala Gln Leu Asp Leu Ile Gly Leu Ser Arg Ile Thr Lys Leu Asp
            515                 520                 525

Gln Ser Val Leu Pro Ala Asn Met Lys Pro Gly Lys Asp Thr Leu Glu
            530                 535                 540

Thr Val Leu Glu Thr Tyr Lys Lys Asp Asn Lys Glu Glu Pro Ala Thr
545                 550                 555                 560

Ile Pro Pro Val Ser Leu Lys Val Ser Gly Leu Thr Gly Leu Lys Glu
                565                 570                 575

Leu Asp Leu Ser Gly Phe Asp Arg Glu Thr Leu Ala Gly Leu Asp Ala
            580                 585                 590

Ala Thr Leu Thr Ser Leu Glu Lys Val Asp Ile Ser Gly Asn Lys Leu
            595                 600                 605

Asp Leu Ala Pro Gly Thr Glu Asn Arg Gln Ile Phe Asp Thr Met Leu
            610                 615                 620

Ser Thr Ile Asn Asn His Val Gly Ser Asn Glu Gln Thr Val Lys Phe
625                 630                 635                 640

Asp Lys Gln Lys Pro Thr Gly His Tyr Pro Asp Thr Tyr Gly Lys Thr
                645                 650                 655

Ser Leu Arg Leu Pro Val Ala Asn Glu Lys Val Asp Leu Gln Ser Gln
            660                 665                 670

Leu Leu Phe Gly Thr Val Thr Asn Gln Gly Thr Leu Ile Asn Ser Glu
            675                 680                 685
```

Ala Asp Tyr Lys Ala Tyr Gln Asn His Lys Ile Ala Gly Arg Ser Phe
690                 695                 700

Val Asp Ser Asn Tyr His Tyr Asn Asn Phe Lys Val Ser Tyr Glu Asn
705                 710                 715                 720

Tyr Thr Val Lys Val Thr Asp Ser Thr Leu Gly Thr Thr Thr Asp Lys
            725                 730                 735

Thr Leu Ala Thr Asp Lys Glu Thr Tyr Lys Val Asp Phe Phe Ser
            740                 745                 750

Pro Ala Asp Lys Thr Lys Ala Val His Thr Ala Lys Val Ile Val Gly
            755                 760                 765

Asp Glu Lys Thr Met Met Val Asn Leu Ala Gly Ala Thr Val Ile
770                 775                 780

Lys Ser Glu Asn Asp Glu Asn Ala Lys Lys Val Phe Asn Gly Ile Met
785                 790                 795                 800

Glu Tyr Asn Pro Ile Ser Thr Gln Asn Arg Ala Ser Ile Ile Phe Glu
            805                 810                 815

Met Lys Asp Pro Ser Leu Ala Lys Tyr Trp Arg Leu Phe Asn Asn Ser
            820                 825                 830

Ser Lys Gly Glu Asp Asp Tyr Ile Lys Glu Ala Lys Leu Glu Val Phe
            835                 840                 845

Thr Gly Gln Leu Asn Ala Glu Ala Asp Val Lys Thr Ser Leu Glu Lys
850                 855                 860

Ser Asp Asp Trp Gln Thr Val Ser Thr Tyr Ser Gly Gln Glu Gln Val
865                 870                 875                 880

Phe Ser His Ala Leu Asp Asn Ile Ser Ala Lys Tyr Trp Arg Ile Thr
            885                 890                 895

Val Asp Asn Lys Lys Asn Gln Tyr Gly Tyr Val Ser Leu Pro Glu Leu
            900                 905                 910

Gln Ile Leu Gly Tyr Pro Leu Pro Asn Ala Asp Thr Ile Met Lys Thr
            915                 920                 925

Val Thr Thr Ala Lys Gly Leu Ser Gln Gln Lys Asp Lys Phe Ser Gln
930                 935                 940

Lys Met Leu Asp Glu Leu Lys Ile Lys Glu Met Ala Leu Glu Thr Ser
945                 950                 955                 960

Leu Asn Ser Lys Ile Phe Asp Val Thr Ala Ile Asn Ala Asn Ala Gly
            965                 970                 975

Val Leu Lys Asp Cys Ile Glu Lys Arg Gln Leu Leu Lys Lys
            980                 985                 990

<210> SEQ ID NO 12
<211> LENGTH: 1017
<212> TYPE: PRT
<213> ORGANISM: Streptococcus pyogenes
<220> FEATURE:
<223> OTHER INFORMATION: Streptococcus pyogenes serotype M6 strain
      MGAS10394 endoglycosidase

<400> SEQUENCE: 12

Met Val Tyr Gln Leu Gly Ser His Asp Leu Val Pro Lys Ile Arg Ser
1               5                   10                  15

Val Gln Met Asp Lys His Leu Leu Val Lys Arg Thr Leu Gly Cys Val
            20                  25                  30

Cys Ala Ala Thr Leu Met Gly Ala Ala Leu Ala Thr His His Asp Ser
        35                  40                  45

Leu Asn Thr Val Lys Ala Glu Glu Lys Thr Val Gln Val Gln Lys Glu

```
              50                  55                  60
Leu Ser Ser Ile Asp Ser Leu His Tyr Leu Ser Glu Asn Ser Lys Lys
65                  70                  75                  80

Glu Phe Lys Glu Glu Leu Ser Lys Glu Lys Val Pro Glu Lys Val Lys
                85                  90                  95

Glu Ile Leu Ala Lys Ala Gln Gln Ala Asp Lys Gln Ala Gln Glu Leu
            100                 105                 110

Ala Lys Met Lys Ile Pro Glu Lys Ile Pro Met Lys Pro Leu His Ser
        115                 120                 125

Pro Leu Tyr Gly Gly Tyr Phe Arg Thr Trp His Asp Lys Thr Ser Asp
    130                 135                 140

Pro Thr Glu Lys Asp Lys Val Asn Ser Met Gly Glu Leu Pro Lys Glu
145                 150                 155                 160

Val Asp Leu Ala Phe Ile Phe His Asp Trp Thr Lys Asp Tyr Ser Leu
                165                 170                 175

Phe Trp Lys Glu Leu Ala Ile Lys His Val Pro Lys Leu Asn Lys Gln
                180                 185                 190

Gly Thr Arg Val Ile Arg Thr Ile Pro Trp Arg Phe Leu Ala Gly Gly
            195                 200                 205

Asp Asn Ser Gly Ile Ala Glu Asp Thr Ser Lys Tyr Pro Asn Thr Pro
        210                 215                 220

Glu Gly Asn Lys Ala Leu Ala Lys Ala Ile Val Asp Glu Tyr Val Tyr
225                 230                 235                 240

Lys Tyr Asn Leu Asp Gly Leu Asp Val Asp Val Glu His Asp Ser Ile
                245                 250                 255

Pro Lys Val Asn Gly Lys Ala Ser Asp Glu Asn Leu Lys Arg Ser Ile
                260                 265                 270

Asp Val Phe Glu Glu Ile Gly Lys Leu Ile Gly Pro Lys Gly Ala Asp
            275                 280                 285

Lys Ser Arg Leu Phe Ile Met Asp Ser Thr Tyr Met Ala Asp Lys Asn
        290                 295                 300

Pro Leu Ile Glu Arg Gly Ala Pro Tyr Ile Asp Leu Leu Leu Val Gln
305                 310                 315                 320

Val Tyr Gly Ala Arg Gly Glu Gln Gly Glu Phe Gln Asn Asp Thr Arg
                325                 330                 335

Leu Val Thr Glu Thr Pro Glu Glu Arg Trp Gln Gly Tyr Ser Lys Tyr
                340                 345                 350

Ile Arg Pro Glu Gln Tyr Met Ile Gly Phe Ser Phe Tyr Glu Glu Arg
            355                 360                 365

Ala Gly Ser Gly Asn Leu Trp Tyr Asp Ile Asn Ser Arg Lys Asp Glu
        370                 375                 380

Asp Lys Ala Asn Gly Ile Asn Thr Asp Ile Thr Gly Thr Arg Ala Glu
385                 390                 395                 400

Arg Tyr Ala Arg Trp Gln Pro Lys Thr Gly Gly Val Lys Gly Gly Ile
                405                 410                 415

Phe Ser Tyr Ala Ile Asp Arg Asp Gly Val Ala His Gln Pro Glu Lys
                420                 425                 430

Val Ala Gln Gln Asp Lys Arg Ser Gln Thr Gln Val Asp Glu Ile Thr
            435                 440                 445

Asp Asn Ile Phe His Ser Asp Tyr Ser Val Ser Lys Ala Leu Lys Thr
        450                 455                 460

Val Met Leu Lys Asp Lys Ser Tyr Asp Leu Ile Asp Glu Lys Asp Phe
465                 470                 475                 480
```

```
Pro Asp Lys Ala Leu Arg Glu Ala Val Met Ala Gln Val Gly Thr Arg
            485                 490                 495
Lys Gly Asp Leu Glu Arg Phe Asn Gly Thr Leu Arg Leu Asp Asn Pro
        500                 505                 510
Ala Ile Gln Ser Leu Glu Gly Leu Asn Lys Phe Lys Lys Leu Ala Gln
            515                 520                 525
Leu Asp Leu Ile Gly Leu Ser Arg Ile Thr Lys Leu Asp Gln Ser Val
        530                 535                 540
Leu Pro Ala Asn Met Lys Pro Gly Lys Asp Thr Leu Glu Thr Val Leu
545                 550                 555                 560
Glu Thr Tyr Lys Lys Asp Asn Lys Glu Glu Pro Ala Thr Ile Pro Pro
                565                 570                 575
Val Ser Leu Lys Val Ser Gly Leu Thr Gly Leu Lys Glu Leu Asp Leu
            580                 585                 590
Ser Gly Phe Asp Arg Glu Thr Leu Ala Gly Leu Asp Ala Ala Thr Leu
        595                 600                 605
Thr Ser Leu Glu Lys Val Asp Ile Ser Gly Asn Lys Leu Asp Leu Ala
        610                 615                 620
Pro Gly Thr Gln Asn Arg Gln Ile Phe Asp Thr Met Leu Ser Thr Val
625                 630                 635                 640
Ser Asn His Val Gly Ser Asn Glu Gln Thr Val Lys Phe Asp Lys Gln
                645                 650                 655
Lys Pro Thr Gly His Tyr Pro Asp Thr Tyr Gly Lys Thr Ser Leu Arg
            660                 665                 670
Leu Pro Val Ala Asn Glu Lys Val Asp Leu Gln Ser Gln Leu Leu Phe
        675                 680                 685
Gly Thr Val Thr Asn Gln Gly Thr Leu Ile Asn Ser Glu Ala Asp Tyr
        690                 695                 700
Lys Ala Tyr Gln Asn His Lys Ile Ala Gly Arg Ser Phe Val Asp Ser
705                 710                 715                 720
Asn Tyr His Tyr Asn Asn Phe Lys Val Ser Tyr Glu Asn Tyr Thr Val
                725                 730                 735
Lys Val Thr Asp Ser Thr Leu Gly Thr Thr Thr Asp Lys Thr Leu Ala
            740                 745                 750
Thr Asp Lys Glu Glu Thr Tyr Lys Val Asp Phe Phe Ser Pro Ala Asp
        755                 760                 765
Lys Thr Lys Ala Val His Thr Ala Lys Val Ile Val Gly Asp Glu Lys
        770                 775                 780
Thr Met Met Val Asn Leu Ala Glu Gly Ala Thr Val Ile Gly Gly Ser
785                 790                 795                 800
Ala Asp Pro Val Asn Ala Arg Lys Val Phe Asp Gly Gln Leu Gly Ser
                805                 810                 815
Glu Thr Asp Asn Ile Ser Leu Gly Trp Asp Ser Lys Gln Ser Ile Ile
            820                 825                 830
Phe Lys Leu Lys Glu Asp Gly Leu Ile Lys Tyr Trp Arg Phe Phe Asn
        835                 840                 845
Asp Ser Ala Arg Asn Pro Lys Thr Thr Asn Lys Pro Ile Gln Glu Ala
        850                 855                 860
Ser Leu Gln Ile Phe Asn Ile Lys Asp Tyr Asn Leu Asp Asn Leu Leu
865                 870                 875                 880
Glu Asn Pro Asn Lys Phe Asp Asp Glu Lys Tyr Trp Ile Thr Val Asp
                885                 890                 895
```

```
Thr Tyr Ser Ala Gln Gly Glu Arg Ala Thr Ala Phe Ser Asn Thr Leu
            900                 905                 910

Asn Asn Ile Thr Ser Lys Tyr Trp Arg Val Val Phe Asp Thr Lys Gly
            915                 920                 925

Asp Arg Tyr Ser Ser Pro Val Val Pro Glu Leu Gln Ile Leu Gly Tyr
        930                 935                 940

Pro Leu Pro Asn Ala Asp Thr Ile Met Lys Thr Val Thr Thr Ala Lys
945                 950                 955                 960

Gly Leu Ser Gln Gln Lys Asp Lys Phe Ser Gln Lys Met Leu Asp Glu
                965                 970                 975

Leu Lys Ile Lys Glu Met Ala Leu Glu Thr Ser Leu Asn Ser Lys Ile
            980                 985                 990

Phe Asp Val Thr Ala Ile Asn Ala Asn Ala Gly Val Leu Lys Asp Cys
            995                 1000                1005

Ile Glu Lys Arg Gln Leu Leu Lys Lys
    1010                1015

<210> SEQ ID NO 13
<211> LENGTH: 1013
<212> TYPE: PRT
<213> ORGANISM: Streptococcus pyogenes
<220> FEATURE:
<223> OTHER INFORMATION: Streptococcus pyogenes serotype M12 strain
      MGAS9429 endoglycosidase

<400> SEQUENCE: 13

Met Val Tyr Gln Leu Gly Ser His Asp Leu Val Pro Lys Ile Arg Ser
 1               5                  10                  15

Val Gln Met Asp Lys His Leu Leu Val Lys Arg Thr Leu Gly Cys Val
            20                  25                  30

Cys Ala Ala Thr Leu Met Gly Ala Ala Leu Ala Thr His His Asp Ser
        35                  40                  45

Leu Asn Thr Val Lys Ala Glu Glu Lys Thr Val Gln Val Gln Lys Glu
    50                  55                  60

Leu Ser Ser Ile Asp Ser Leu His Tyr Leu Ser Glu Asn Ser Lys Lys
65                  70                  75                  80

Glu Phe Lys Glu Glu Leu Ser Lys Ala Gly Gln Glu Ser Gln Lys Val
                85                  90                  95

Lys Glu Ile Leu Ala Lys Ala Gln Gln Ala Asp Lys Gln Ala Gln Glu
            100                 105                 110

Leu Ala Lys Met Lys Ile Pro Glu Lys Ile Pro Met Lys Pro Leu His
        115                 120                 125

Gly Pro Leu Tyr Gly Gly Tyr Phe Arg Thr Trp His Asp Lys Thr Ser
130                 135                 140

Asp Pro Thr Glu Lys Asp Lys Val Asn Ser Met Gly Glu Leu Pro Lys
145                 150                 155                 160

Glu Val Asp Leu Ala Phe Ile Phe His Asp Trp Thr Lys Asp Tyr Ser
                165                 170                 175

Leu Phe Trp Lys Glu Leu Ala Thr Lys His Val Pro Lys Leu Asn Lys
            180                 185                 190

Gln Gly Thr Arg Val Ile Arg Thr Ile Pro Trp Arg Phe Leu Ala Gly
        195                 200                 205

Gly Asp Asn Ser Gly Ile Ala Glu Asp Thr Ser Lys Tyr Pro Asn Thr
    210                 215                 220

Pro Glu Gly Asn Lys Ala Leu Ala Lys Ala Ile Val Asp Glu Tyr Val
225                 230                 235                 240
```

```
Tyr Lys Tyr Asn Leu Asp Gly Leu Asp Val Asp Val Glu His Asp Ser
                245                 250                 255
Ile Pro Lys Val Asn Gly Glu Ala Ser Asp Glu Asn Leu Lys Arg Ser
                260                 265                 270
Ile Asp Val Phe Glu Glu Ile Gly Lys Leu Ile Gly Pro Lys Gly Val
            275                 280                 285
Asp Lys Ser Arg Leu Phe Ile Met Asp Ser Thr Tyr Met Ala Asp Lys
        290                 295                 300
Asn Pro Leu Ile Glu Arg Gly Ala Ser Tyr Ile Asn Leu Leu Leu Val
305                 310                 315                 320
Gln Val Tyr Gly Ser Gln Gly Glu Lys Gly Val Phe Gln Asn Asp Thr
                325                 330                 335
Lys Leu Val Thr Asp Thr Pro Glu Glu Arg Trp Gln Gly Tyr Ser Lys
                340                 345                 350
Tyr Ile Arg Pro Glu Gln Tyr Met Ile Gly Phe Ser Phe Tyr Glu Glu
            355                 360                 365
Asn Ala Gln Glu Gly Asn Leu Trp Tyr Asp Ile Asn Ser Arg Lys Asp
        370                 375                 380
Glu Asp Thr Ala Asn Gly Ile Asn Thr Asp Ile Thr Gly Thr Arg Ala
385                 390                 395                 400
Glu Arg Tyr Ala Arg Trp Gln Pro Lys Thr Gly Gly Ala Lys Gly Gly
                405                 410                 415
Ile Phe Ser Tyr Ala Ile Asp Arg Asp Gly Val Ala His Gln Pro Lys
            420                 425                 430
Lys Tyr Ala Lys Gln Lys Glu Phe Lys Asp Ala Thr Asp Asn Ile Phe
        435                 440                 445
His Ser Asp Tyr Ser Val Ser Lys Ala Leu Lys Thr Val Met Leu Lys
    450                 455                 460
Asp Lys Ser Tyr Asp Leu Ile Asp Glu Lys Asp Phe Pro Asp Lys Ala
465                 470                 475                 480
Leu Arg Glu Ala Val Met Ala Gln Val Gly Thr Arg Lys Gly Asp Leu
                485                 490                 495
Glu Arg Phe Asn Gly Thr Leu Arg Leu Asp Asn Pro Ala Ile Gln Ser
            500                 505                 510
Leu Glu Gly Leu Asn Lys Phe Lys Lys Leu Ala Gln Leu Asp Leu Ile
        515                 520                 525
Gly Leu Ser Arg Ile Thr Lys Leu Asp Gln Ser Val Leu Pro Ala Asn
    530                 535                 540
Met Lys Pro Gly Lys Asp Thr Leu Glu Thr Val Leu Glu Thr Tyr Lys
545                 550                 555                 560
Lys Asp Asn Lys Glu Glu Pro Ala Thr Ile Pro Pro Val Ser Leu Lys
                565                 570                 575
Val Ser Gly Leu Thr Gly Leu Lys Glu Leu Asp Leu Ser Gly Phe Asp
            580                 585                 590
Arg Glu Thr Leu Ala Gly Leu Asp Ala Ala Thr Leu Thr Ser Leu Glu
        595                 600                 605
Lys Val Asp Ile Ser Gly Asn Lys Leu Asp Leu Ala Pro Gly Thr Glu
    610                 615                 620
Asn Arg Gln Ile Phe Asp Thr Met Leu Ser Thr Val Ser Asn His Val
625                 630                 635                 640
Gly Ser Asn Lys Gln Thr Val Lys Phe Asp Lys Gln Lys Pro Thr Gly
                645                 650                 655
```

His Tyr Pro Asp Thr Tyr Gly Lys Thr Ser Leu Arg Leu Pro Val Ala
            660                 665                 670

Asn Glu Lys Val Asp Leu Gln Ser Gln Leu Leu Phe Gly Thr Val Thr
        675                 680                 685

Asn Gln Gly Thr Leu Ile Asn Ser Glu Ala Asp Tyr Lys Ala Tyr Gln
    690                 695                 700

Asn Gln Gln Ile Ala Gly Arg Ser Phe Val Asp Ser Asn Tyr His Tyr
705                 710                 715                 720

Asn Asn Phe Lys Val Ser Tyr Glu Asn Tyr Thr Val Lys Val Thr Asp
            725                 730                 735

Ser Thr Leu Gly Thr Thr Thr Asp Lys Thr Leu Ala Thr Asp Lys Glu
        740                 745                 750

Glu Thr Tyr Lys Val Asp Phe Phe Ser Pro Ala Asp Lys Thr Lys Ala
    755                 760                 765

Val His Thr Ala Lys Val Ile Val Gly Asp Glu Lys Thr Met Met Val
770                 775                 780

Asn Leu Ala Glu Gly Ala Thr Val Ile Gly Ser Ala Asp Lys Glu
785                 790                 795                 800

Met Ser Arg Asn Val Phe Asp Gly Ser Leu Gly Gly Asp Arg Ser Asn
            805                 810                 815

Leu Leu Gly Met Ser Gly Pro Lys Ser Thr Ile Ile Phe Asn Leu Lys
        820                 825                 830

Glu Ser Gly Ile Val Lys His Trp Arg Phe Phe Asn Asp Arg Ala Arg
    835                 840                 845

Ser Pro Gln Asn Pro Ala Glu Asp Ile Gln Glu Ile Lys Leu Gln Val
850                 855                 860

Phe Asp Ser Glu Lys Tyr Asp Ile Glu Thr Leu Leu Lys Thr Pro Asn
865                 870                 875                 880

Gln Phe Asp Lys Asp Asp Tyr Trp Ile Thr Val Asp Ser Tyr Lys Ser
            885                 890                 895

Lys Ser Glu Thr Val Asn Asn Tyr Asp Gln Val Leu Lys Met Asn Ser
        900                 905                 910

Ala Lys Tyr Trp Arg Val Thr Val Asp Thr Lys Gly Gly Asn Tyr Ser
    915                 920                 925

Trp Pro Ser Leu Pro Glu Leu Gln Ile Leu Gly Tyr Pro Leu Pro Asn
930                 935                 940

Ala Asp Thr Ile Met Lys Thr Val Thr Ile Ala Lys Gly Leu Ser Gln
945                 950                 955                 960

Gln Lys Asp Lys Phe Ser Gln Lys Met Leu Asp Glu Leu Lys Ile Lys
            965                 970                 975

Glu Met Ala Leu Glu Thr Ser Leu Asn Ser Lys Ile Phe Asp Val Thr
        980                 985                 990

Ala Ile Asn Ala Asn Ala Gly Val Leu Lys Asp Cys Ile Glu Lys Arg
    995                 1000                1005

Gln Leu Leu Lys Lys
    1010

<210> SEQ ID NO 14
<211> LENGTH: 975
<212> TYPE: PRT
<213> ORGANISM: Streptococcus pyogenes
<220> FEATURE:
<223> OTHER INFORMATION: Streptococcus pyogenes serotype M18 strain
      MGAS8232 endoglycosidase

<400> SEQUENCE: 14

```
Met Asp Lys His Leu Leu Val Lys Arg Thr Leu Gly Cys Val Cys Ala
 1               5                  10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Glu Leu Pro
                35                  40                  45

Ser Ile Asp Ser Leu His Tyr Leu Ser Glu Asn Ser Lys Lys Glu Phe
        50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Ala Ser Lys Tyr Pro Asn Thr Pro Glu
        195                 200                 205

Gly Asn Lys Ala Leu Ala Lys Ala Ile Val Asp Glu Tyr Val Tyr Lys
        210                 215                 220

Tyr Asn Leu Asp Gly Leu Asp Val Asp Val Glu His Asp Ser Ile Pro
225                 230                 235                 240

Lys Val Asn Gly Glu Ala Ser Asp Glu Asn Leu Lys Arg Ser Ile Asp
                245                 250                 255

Val Phe Glu Glu Ile Gly Lys Leu Ile Gly Pro Lys Gly Thr Asp Lys
                260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
        290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Arg Ala
                340                 345                 350

Gly Ser Gly Asn Leu Trp Tyr Asp Ile Asn Val Glu Asp Glu Ser Asn
        355                 360                 365

Pro Asn Ile Gly Lys Glu Ile Lys Gly Thr Arg Ala Glu Arg Tyr Ala
        370                 375                 380

Lys Trp Gln Pro Lys Thr Gly Gly Val Lys Gly Ile Phe Ser Tyr
385                 390                 395                 400

Ala Val Asp Arg Asp Gly Val Ala His Pro Lys Lys Asn Gly Tyr Lys
                405                 410                 415
```

```
Asn Pro Lys Leu Asp Asn Ile Val Thr Ser Asp Tyr Ser Val Ser Lys
            420                 425                 430

Ala Leu Lys Thr Val Met Leu Lys Asp Lys Ser Tyr Asp Leu Ile Asp
        435                 440                 445

Glu Lys Asp Phe Pro Asp Lys Ala Leu Arg Glu Ala Val Met Ala Gln
    450                 455                 460

Val Gly Thr Arg Lys Gly Asp Leu Glu Arg Phe Asn Gly Thr Leu Arg
465                 470                 475                 480

Leu Asp Asn Pro Ala Ile Gln Ser Leu Glu Gly Leu Asn Lys Phe Lys
                485                 490                 495

Lys Leu Ala Gln Leu Asp Leu Ile Gly Leu Ser Arg Ile Thr Lys Leu
            500                 505                 510

Asp Gln Ser Val Leu Pro Ala Asn Met Lys Pro Gly Lys Asp Thr Leu
        515                 520                 525

Glu Thr Val Leu Glu Thr Tyr Lys Lys Asp Asn Lys Glu Glu Pro Ala
    530                 535                 540

Thr Ile Pro Pro Val Ser Leu Lys Val Ser Gly Leu Thr Gly Leu Lys
545                 550                 555                 560

Glu Leu Asp Leu Ser Gly Phe Asp Arg Glu Thr Leu Ala Gly Leu Asp
                565                 570                 575

Ala Ala Thr Leu Thr Ser Leu Glu Lys Val Asp Ile Ser Gly Asn Lys
            580                 585                 590

Leu Asp Leu Ala Pro Gly Thr Glu Asn Arg Gln Ile Phe Asp Thr Met
        595                 600                 605

Leu Ser Thr Val Ser Asn His Val Gly Ser Asn Glu Gln Thr Val Lys
    610                 615                 620

Phe Asp Lys Gln Lys Pro Thr Gly His Tyr Pro Asp Thr Tyr Gly Lys
625                 630                 635                 640

Thr Ser Leu Arg Leu Pro Val Ala Asn Glu Lys Val Asp Leu Gln Ser
                645                 650                 655

Gln Leu Leu Phe Gly Thr Val Thr Asn Gln Gly Thr Leu Ile Asn Ser
            660                 665                 670

Glu Ala Asp Tyr Lys Ala Tyr Gln Asn His Lys Ile Ala Gly Arg Ser
        675                 680                 685

Phe Val Asp Ser Asn Tyr His Tyr Asn Asn Phe Lys Val Ser Tyr Glu
    690                 695                 700

Asn Tyr Thr Val Lys Val Thr Asp Ser Thr Leu Gly Thr Thr Thr Asp
705                 710                 715                 720

Lys Thr Leu Ala Thr Asp Lys Glu Thr Tyr Lys Val Asp Phe Phe
                725                 730                 735

Ser Pro Ala Asp Lys Thr Lys Ala Val His Thr Ala Lys Val Ile Val
            740                 745                 750

Gly Asp Glu Lys Thr Met Met Val Asn Leu Ala Glu Gly Ala Thr Val
        755                 760                 765

Ile Lys Ser Glu Asn Asp Glu Asn Ala Lys Lys Val Phe Asn Gly Ile
    770                 775                 780

Met Glu Tyr Asn Pro Ile Ser Thr Gln Asn Arg Ala Ser Ile Ile Phe
785                 790                 795                 800

Glu Ile Lys Asp Pro Ser Leu Ala Lys Tyr Trp Arg Leu Phe Asn Asp
                805                 810                 815

Ser Ser Lys Asp Lys Lys Asp Tyr Ile Lys Glu Ala Lys Leu Glu Val
            820                 825                 830

Phe Thr Gly Gln Leu Asn Ala Glu Ala Asp Val Lys Thr Ser Leu Glu
```

```
                    835                 840                 845
Lys Ser Asp Asp Trp Gln Thr Val Ser Thr Tyr Ser Gly Gln Glu Gln
850                 855                 860

Val Phe Ser His Ala Leu Asp Asn Ile Ser Ala Lys Tyr Trp Arg Ile
865                 870                 875                 880

Thr Val Asp Thr Lys Gly Gly Asn Tyr Ser Trp Pro Ser Leu Pro Glu
                    885                 890                 895

Leu Gln Ile Leu Gly Tyr Pro Leu Pro Asn Ala Asp Thr Ile Met Lys
                900                 905                 910

Thr Val Thr Thr Ala Lys Gly Leu Ser Gln Gln Lys Asp Lys Phe Ser
                915                 920                 925

Gln Lys Met Leu Asp Glu Leu Lys Ile Lys Glu Met Ala Leu Glu Thr
            930                 935                 940

Ser Leu Asn Ser Lys Ile Phe Asp Val Thr Ala Ile Asn Ala Asn Ala
945                 950                 955                 960

Gly Val Leu Lys Asp Cys Ile Glu Lys Arg Gln Leu Leu Lys Lys
                    965                 970                 975

<210> SEQ ID NO 15
<211> LENGTH: 1022
<212> TYPE: PRT
<213> ORGANISM: Streptococcus pyogenes
<220> FEATURE:
<223> OTHER INFORMATION: Streptococcus pyogenes serotype M28 strain
      MGAS6180 endoglycosidase

<400> SEQUENCE: 15

Met Val Tyr Gln Leu Gly Ser His Asp Leu Val Pro Lys Ile Arg Ser
1               5                   10                  15

Val Gln Met Asp Lys His Leu Leu Val Lys Arg Thr Leu Gly Cys Val
                20                  25                  30

Cys Ala Ala Thr Leu Met Gly Ala Ala Leu Ala Thr His His Asp Ser
            35                  40                  45

Leu Asn Thr Val Lys Ala Glu Glu Lys Thr Val Gln Val Gln Lys Glu
        50                  55                  60

Leu Ser Ser Ile Asp Ser Leu His Tyr Leu Ser Glu Asn Ser Lys Lys
65                  70                  75                  80

Glu Phe Lys Glu Glu Leu Ser Lys Ala Gly Gln Glu Ser Gln Lys Val
                85                  90                  95

Lys Glu Ile Leu Ala Lys Ala Gln Gln Ala Asp Lys Gln Ala Gln Glu
                100                 105                 110

Leu Ala Lys Met Lys Ile Pro Glu Lys Ile Pro Met Lys Pro Leu His
            115                 120                 125

Gly Pro Leu Tyr Gly Tyr Phe Arg Thr Trp His Asp Lys Thr Ser
        130                 135                 140

Asp Pro Thr Glu Lys Asp Lys Val Asn Ser Met Gly Glu Leu Pro Lys
145                 150                 155                 160

Glu Val Asp Leu Ala Phe Ile Phe His Asp Trp Thr Lys Asp Tyr Ser
                165                 170                 175

Leu Phe Trp Lys Glu Leu Ala Thr Lys His Val Pro Lys Leu Asn Lys
                180                 185                 190

Gln Gly Thr Arg Val Ile Arg Thr Ile Pro Trp Arg Phe Leu Ala Gly
            195                 200                 205

Gly Asp Asn Ser Gly Ile Ala Glu Asp Thr Ser Lys Tyr Pro Asn Thr
        210                 215                 220
```

```
Pro Glu Gly Asn Lys Ala Leu Ala Lys Ala Ile Val Asp Glu Tyr Val
225                 230                 235                 240

Tyr Lys Tyr Asn Leu Asp Gly Leu Asp Val Asp Val Glu His Asp Ser
            245                 250                 255

Ile Pro Lys Val Asn Gly Glu Ala Ser Asp Glu Asn Leu Lys Arg Ser
        260                 265                 270

Ile Asp Val Phe Glu Glu Ile Gly Lys Leu Ile Gly Pro Lys Gly Ala
    275                 280                 285

Asp Lys Ser Arg Leu Phe Ile Met Asp Ser Thr Tyr Met Ala Asp Lys
290                 295                 300

Asn Pro Leu Ile Glu Arg Gly Ala Pro Tyr Ile Asp Leu Leu Leu Val
305                 310                 315                 320

Gln Val Tyr Gly Ala Arg Gly Glu Gln Gly Glu Phe Gln Asn Asp Thr
            325                 330                 335

Lys Leu Val Thr Asp Thr Pro Glu Glu Arg Trp Gln Gly Tyr Ser Lys
        340                 345                 350

Tyr Ile Arg Pro Glu Gln Tyr Met Ile Gly Phe Ser Phe Tyr Glu Glu
    355                 360                 365

Arg Ala Gly Ser Gly Asn Leu Trp Tyr Asp Ile Asn Ser Arg Lys Asp
370                 375                 380

Glu Asp Lys Ala Asn Gly Ile Asn Thr Asp Ile Thr Gly Thr Arg Ala
385                 390                 395                 400

Glu Arg Tyr Ala Arg Trp Gln Pro Lys Thr Gly Gly Val Lys Gly Gly
            405                 410                 415

Ile Phe Ser Tyr Ala Val Asp Arg Asp Gly Val Ala His Gln Pro Lys
        420                 425                 430

Gln Ile Ala Glu Lys Asp Lys Gln Asn Val Lys Asn Gln Pro Gln
    435                 440                 445

Ile Pro Glu Ile Thr Asp Asn Ile Phe His Ser Asp Tyr Ser Val Ser
450                 455                 460

Lys Ala Leu Lys Thr Val Met Leu Lys Asp Lys Ser Tyr Asp Leu Ile
465                 470                 475                 480

Asp Glu Lys Asp Phe Pro Asp Lys Ala Leu Arg Glu Ala Val Met Ala
            485                 490                 495

Gln Val Gly Thr Arg Lys Gly Asp Leu Glu Arg Phe Asn Gly Ile Leu
        500                 505                 510

Arg Leu Asp Asn Pro Ala Ile Gln Ser Leu Glu Gly Leu Asn Lys Phe
    515                 520                 525

Lys Lys Leu Ala Gln Leu Asp Leu Ile Gly Leu Ser Arg Ile Thr Lys
530                 535                 540

Leu Asp Gln Ser Val Leu Pro Ala Asn Met Lys Pro Gly Lys Asp Thr
545                 550                 555                 560

Leu Glu Thr Val Leu Glu Thr Tyr Lys Lys Asp Asn Lys Glu Glu Pro
            565                 570                 575

Ala Thr Ile Pro Pro Val Ser Leu Lys Val Ser Gly Leu Thr Gly Leu
        580                 585                 590

Lys Glu Leu Asp Leu Ser Gly Phe Asp Arg Glu Thr Leu Ala Gly Leu
    595                 600                 605

Asp Val Ala Thr Leu Thr Ser Leu Glu Lys Val Asp Ile Ser Gly Asn
610                 615                 620

Lys Leu Asp Leu Ala Pro Gly Thr Glu Asn Arg Gln Ile Phe Asp Thr
625                 630                 635                 640

Met Leu Ser Thr Val Ser Asn His Val Gly Ser Asn Glu Gln Thr Val
```

645                 650                 655
Lys Phe Asp Lys Gln Lys Pro Thr Gly His Tyr Pro Asp Thr Tyr Gly
                660                 665                 670

Lys Thr Ser Leu Arg Leu Pro Val Ala Asn Gly Lys Val Asp Leu Gln
        675                 680                 685

Ser Gln Leu Leu Phe Gly Thr Val Thr Asn Gln Gly Thr Leu Ile Asn
    690                 695                 700

Ser Glu Ala Asp Tyr Lys Ala Tyr Gln Asn Gln Ile Ala Gly Arg
705                 710                 715                 720

Ser Phe Val Asp Ser Asn Tyr His Tyr Asn Asn Phe Lys Val Ser Tyr
                725                 730                 735

Glu Asn Tyr Thr Val Lys Val Thr Asp Ser Thr Leu Gly Thr Thr Thr
                740                 745                 750

Asp Lys Thr Leu Ala Thr Asp Lys Glu Thr Tyr Lys Val Asp Phe
            755                 760                 765

Phe Ser Pro Ala Asp Lys Thr Lys Ala Val His Thr Ala Lys Val Ile
    770                 775                 780

Val Gly Asp Glu Lys Thr Met Met Val Asn Leu Ala Glu Gly Ala Thr
785                 790                 795                 800

Val Ile Gly Gly Ser Ala Asp Pro Val Asn Ala Arg Lys Val Phe Asp
                805                 810                 815

Gly Gln Leu Gly Ser Glu Thr Asp Asn Ile Ser Leu Gly Trp Asp Ser
            820                 825                 830

Lys Gln Ser Ile Ile Phe Lys Leu Lys Glu Asp Gly Leu Ile Lys Tyr
        835                 840                 845

Trp Arg Phe Phe Asn Asp Ser Ala Arg Asn Pro Lys Thr Thr Asn Lys
    850                 855                 860

Pro Ile Gln Glu Ala Ser Leu Gln Ile Phe Asn Ile Lys Asp Tyr Asn
865                 870                 875                 880

Leu Asp Asn Leu Leu Glu Asn Pro Asn Lys Phe Asp Asp Glu Lys Tyr
                885                 890                 895

Trp Ile Thr Val Asp Thr Tyr Ser Ala Gln Gly Glu Arg Ala Thr Ala
            900                 905                 910

Phe Ser Asn Thr Leu Asn Asn Ile Thr Ser Lys Tyr Trp Arg Val Val
        915                 920                 925

Phe Asp Thr Lys Gly Asp Arg Tyr Ser Ser Pro Val Val Pro Glu Leu
    930                 935                 940

Gln Ile Leu Gly Tyr Pro Leu Pro Asn Ala Asp Thr Ile Met Lys Thr
945                 950                 955                 960

Val Thr Ile Ala Lys Gly Leu Ser Gln Gln Lys Asp Lys Phe Ser Gln
                965                 970                 975

Lys Met Leu Asp Glu Leu Lys Ile Lys Glu Met Ala Leu Glu Thr Ser
            980                 985                 990

Leu Asn Ser Lys Ile Phe Asp Val Thr Ala Ile Asn Ala Asn Ala Gly
        995                 1000                1005

Val Leu Lys Asp Cys Ile Glu Lys Arg Gln Leu Leu Lys Lys
    1010                1015                1020

<210> SEQ ID NO 16
<211> LENGTH: 764
<212> TYPE: PRT
<213> ORGANISM: Streptococcus pyogenes
<220> FEATURE:
<223> OTHER INFORMATION: Streptococcus pyogenes serotype M49 strain 591
      endoglycosidase

<400> SEQUENCE: 16

```
Thr Gly Ile Asp Gly Lys Gln Gln His Pro Glu Asn Thr Met Ala Glu
1               5                   10                  15

Val Pro Lys Glu Val Asp Ile Leu Phe Val Phe His Asp His Thr Ala
            20                  25                  30

Ser Asp Ser Pro Phe Trp Ser Glu Leu Lys Asp Ser Tyr Val His Lys
        35                  40                  45

Leu His Gln Gln Gly Thr Ala Leu Val Gln Thr Ile Gly Val Asn Glu
    50                  55                  60

Leu Asn Gly Arg Thr Gly Leu Ser Lys Asp Tyr Pro Asp Thr Pro Glu
65                  70                  75                  80

Gly Asn Lys Ala Leu Ala Ala Ile Val Lys Ala Phe Val Thr Asp
                85                  90                  95

Arg Gly Val Asp Gly Leu Asp Ile Asp Ile Glu His Glu Phe Thr Asn
                100                 105                 110

Lys Arg Thr Pro Glu Glu Asp Ala Arg Ala Leu Asn Val Phe Lys Glu
            115                 120                 125

Ile Ala Gln Leu Ile Gly Lys Asn Gly Ser Asp Lys Ser Lys Leu Leu
    130                 135                 140

Ile Met Asp Thr Thr Leu Ser Val Glu Asn Asn Pro Ile Phe Lys Gly
145                 150                 155                 160

Ile Ala Glu Asp Leu Asp Tyr Leu Leu Arg Gln Tyr Tyr Gly Ser Gln
                165                 170                 175

Gly Gly Glu Ala Glu Val Asp Thr Ile Asn Ser Asp Trp Asn Gln Tyr
            180                 185                 190

Gln Asn Tyr Ile Asp Ala Ser Gln Phe Met Ile Gly Phe Ser Phe Phe
        195                 200                 205

Glu Glu Ser Ala Ser Lys Gly Asn Leu Trp Phe Asp Val Asn Glu Tyr
    210                 215                 220

Asp Pro Asn Asn Pro Glu Lys Gly Lys Asp Ile Glu Gly Thr Arg Ala
225                 230                 235                 240

Lys Lys Tyr Ala Glu Trp Gln Pro Ser Thr Gly Gly Leu Lys Ala Gly
                245                 250                 255

Ile Phe Ser Tyr Ala Ile Asp Arg Asp Gly Val Ala His Val Pro Ser
            260                 265                 270

Thr Tyr Lys Asn Arg Thr Ser Thr Asn Leu Gln Arg His Glu Val Asp
        275                 280                 285

Asn Ile Ser His Thr Asp Tyr Thr Val Ser Arg Lys Leu Lys Thr Leu
    290                 295                 300

Met Thr Glu Asp Lys Arg Tyr Asp Val Ile Asp Gln Lys Asp Ile Pro
305                 310                 315                 320

Asp Pro Ala Leu Arg Glu Gln Ile Ile Gln Gln Val Gly Gln Tyr Lys
                325                 330                 335

Gly Asp Leu Glu Arg Tyr Asn Lys Thr Leu Val Leu Thr Gly Asp Lys
            340                 345                 350

Ile Gln Asn Leu Lys Gly Leu Glu Lys Leu Ser Lys Leu Gln Lys Leu
        355                 360                 365

Glu Leu Arg Gln Leu Ser Asn Val Lys Glu Ile Thr Pro Glu Leu Leu
    370                 375                 380

Pro Glu Ser Met Lys Lys Asp Ala Glu Leu Val Met Val Gly Met Thr
385                 390                 395                 400

Gly Leu Glu Lys Leu Asn Leu Ser Gly Leu Asn Arg Gln Thr Leu Asp
```

```
                    405                 410                 415
Gly Ile Asp Val Asn Ser Ile Thr His Leu Thr Ser Phe Asp Ile Ser
                420                 425                 430

His Asn Ser Leu Asp Leu Ser Glu Lys Ser Glu Asp Arg Lys Leu Leu
            435                 440                 445

Met Thr Leu Met Glu Gln Val Ser Asn His Gln Lys Ile Thr Val Lys
450                 455                 460

Asn Thr Ala Phe Glu Asn Gln Lys Pro Lys Gly Tyr Tyr Pro Gln Thr
465                 470                 475                 480

Tyr Asp Thr Lys Glu Gly His Tyr Asp Val Asp Asn Ala Glu His Asp
                485                 490                 495

Ile Leu Thr Asp Phe Val Phe Gly Thr Val Thr Lys Arg Asn Thr Phe
            500                 505                 510

Ile Gly Asp Glu Glu Ala Phe Ala Ile Tyr Lys Glu Gly Ala Val Asp
        515                 520                 525

Gly Arg Gln Tyr Val Ser Lys Asp Tyr Thr Tyr Glu Ala Phe Arg Lys
    530                 535                 540

Asp Tyr Lys Gly Tyr Lys Val His Leu Thr Ala Ser Asn Leu Gly Glu
545                 550                 555                 560

Thr Val Thr Ser Lys Val Thr Ala Thr Thr Asp Glu Thr Tyr Leu Val
                565                 570                 575

Asp Val Ser Asp Gly Glu Lys Val Val His His Met Lys Leu Asn Ile
            580                 585                 590

Gly Ser Gly Ala Ile Met Met Glu Asn Leu Ala Lys Gly Ala Lys Val
        595                 600                 605

Ile Gly Thr Ser Gly Asp Phe Glu Gln Ala Lys Lys Ile Phe Asp Gly
    610                 615                 620

Glu Lys Ser Asp Arg Phe Phe Thr Trp Gly Gln Thr Asn Trp Ile Ala
625                 630                 635                 640

Phe Asp Leu Gly Glu Ile Asn Leu Ala Lys Glu Trp Arg Leu Phe Asn
                645                 650                 655

Ala Glu Thr Asn Thr Glu Ile Lys Thr Asp Ser Ser Leu Asn Val Ala
            660                 665                 670

Lys Gly Arg Leu Gln Ile Leu Lys Asp Thr Thr Ile Asp Leu Glu Lys
        675                 680                 685

Met Asp Ile Lys Asn Arg Lys Glu Tyr Leu Ser Asn Asp Glu Asn Trp
    690                 695                 700

Thr Asp Val Ala Gln Met Asp Asp Ala Lys Ala Ile Phe Asn Ser Lys
705                 710                 715                 720

Leu Ser Asn Val Leu Ser Arg Tyr Trp Arg Phe Cys Val Asp Gly Gly
                725                 730                 735

Ala Ser Ser Tyr Tyr Pro Gln Tyr Thr Glu Leu Gln Ile Leu Gly Gln
            740                 745                 750

Arg Leu Ser Asn Asp Val Ala Asn Thr Leu Lys Asp
        755                 760

<210> SEQ ID NO 17
<211> LENGTH: 1018
<212> TYPE: PRT
<213> ORGANISM: Streptococcus equi
<220> FEATURE:
<223> OTHER INFORMATION: Streptococcus equi strain 4047 endoglycosidase

<400> SEQUENCE: 17

Met Glu Lys Gln Val Leu Val Lys Lys Thr Leu Lys Cys Val Cys Ala
```

-continued

```
  1               5                   10                  15
Ala Ala Leu Met Val Ala Ile Leu Ala Ala Gln His Asp Ser Leu Ile
                 20                  25                  30

Arg Val Lys Ala Glu Asp Lys Val Gln Thr Ser Pro Ser Val Ser
                 35                  40                  45

Ala Ile Asp Asp Leu His Tyr Leu Ser Glu Asn Ser Lys Lys Glu Phe
                 50                  55                  60

Lys Glu Gly Leu Ser Lys Ala Gly Glu Val Pro Glu Lys Leu Lys Asp
 65                  70                  75                  80

Ile Leu Ser Lys Ala Gln Gln Ala Asp Lys Gln Ala Lys Val Leu Ala
                 85                  90                  95

Glu Met Lys Val Pro Glu Lys Ile Ala Met Lys Pro Leu Lys Gly Pro
                100                 105                 110

Leu Tyr Gly Gly Tyr Phe Arg Thr Trp His Asp Lys Thr Ser Asp Pro
                115                 120                 125

Ala Glu Lys Asp Lys Val Asn Ser Met Gly Glu Leu Pro Lys Glu Val
                130                 135                 140

Asp Leu Ala Phe Val Phe His Asp Trp Thr Lys Asp Tyr Ser Phe Phe
145                 150                 155                 160

Trp Gln Glu Leu Ala Thr Lys His Val Pro Thr Leu Asn Lys Gln Gly
                165                 170                 175

Thr Arg Val Ile Arg Thr Ile Pro Trp Arg Phe Leu Ala Gly Gly Asp
                180                 185                 190

His Ser Gly Ile Ala Glu Asp Thr Gln Lys Tyr Pro Asn Thr Pro Glu
                195                 200                 205

Gly Asn Lys Ala Leu Ala Lys Ala Ile Val Asp Glu Tyr Val Tyr Lys
                210                 215                 220

Tyr Asn Leu Asp Gly Leu Asp Val Asp Ile Glu Arg Asp Ser Ile Pro
225                 230                 235                 240

Lys Val Asn Gly Lys Glu Ser Asn Glu Asn Ile Gln Arg Ser Ile Ala
                245                 250                 255

Val Phe Glu Glu Ile Gly Lys Leu Ile Gly Pro Lys Gly Ala Asp Lys
                260                 265                 270

Ser Arg Leu Phe Ile Met Asp Ser Thr Tyr Met Ala Asp Lys Asn Pro
                275                 280                 285

Leu Ile Glu Arg Gly Ala Gln Tyr Ile Asp Leu Leu Leu Val Gln Val
                290                 295                 300

Tyr Gly Thr Gln Gly Glu Lys Gly Asp Trp Asp Pro Val Ala Arg Lys
305                 310                 315                 320

Pro Glu Lys Thr Met Glu Glu Arg Trp Glu Ser Tyr Ser Lys Tyr Ile
                325                 330                 335

Arg Pro Glu Gln Tyr Met Val Gly Phe Ser Phe Tyr Glu Glu Asn Ala
                340                 345                 350

Gly Ser Gly Asn Leu Trp Tyr Asp Ile Asn Glu Arg Lys Asp Asp His
                355                 360                 365

Asn Pro Leu Asn Ser Glu Ile Ala Gly Thr Arg Ala Glu Arg Tyr Ala
                370                 375                 380

Lys Trp Gln Pro Lys Thr Gly Gly Val Lys Gly Gly Ile Phe Ser Tyr
385                 390                 395                 400

Ala Ile Asp Arg Asp Gly Val Ala His Gln Pro Lys Lys Val Ser Asp
                405                 410                 415

Asp Glu Lys Arg Thr Asn Lys Ala Ile Lys Asp Ile Thr Asp Gly Ile
                420                 425                 430
```

```
Val Lys Ser Asp Tyr Lys Val Ser Lys Ala Leu Lys Lys Val Met Glu
            435                 440                 445
Asn Asp Lys Ser Tyr Glu Leu Ile Asp Gln Lys Asp Phe Pro Asp Lys
450                 455                 460
Ala Leu Arg Glu Ala Val Ile Ala Gln Val Gly Ser Arg Arg Gly Asp
465                 470                 475                 480
Leu Glu Arg Phe Asn Gly Thr Leu Arg Leu Asp Asn Pro Asp Ile Lys
                485                 490                 495
Ser Leu Glu Gly Leu Asn Lys Leu Lys Lys Leu Ala Lys Leu Glu Leu
                500                 505                 510
Ile Gly Leu Ser Gln Ile Thr Lys Leu Asp Ser Leu Val Leu Pro Ala
                515                 520                 525
Asn Ala Lys Pro Thr Lys Asp Thr Leu Ala Asn Val Leu Glu Ala Tyr
                530                 535                 540
Asp Ser Ala Lys Lys Glu Glu Thr Lys Ala Ile Pro Gln Val Ala Leu
545                 550                 555                 560
Thr Ile Ser Gly Leu Thr Gly Leu Lys Glu Leu Asn Leu Ala Gly Phe
                565                 570                 575
Asp Arg Asp Ser Leu Ala Gly Ile Asp Ala Ala Ser Leu Thr Ser Leu
                580                 585                 590
Glu Lys Val Asp Leu Ser Ser Asn Lys Leu Asp Leu Ala Ala Gly Thr
                595                 600                 605
Glu Asn Arg Gln Ile Leu Asp Thr Met Leu Ala Thr Val Thr Lys His
                610                 615                 620
Gly Gly Val Ser Glu Lys Thr Phe Val Phe Asp His Gln Lys Pro Thr
625                 630                 635                 640
Gly Leu Tyr Pro Asp Thr Tyr Gly Thr Lys Ser Leu Gln Leu Pro Val
                645                 650                 655
Ala Asn Asp Thr Ile Asp Leu Gln Ala Lys Leu Leu Phe Gly Thr Val
                660                 665                 670
Thr Asn Gln Gly Thr Leu Ile Asn Ser Glu Ala Asp Tyr Lys Ala Tyr
                675                 680                 685
Gln Glu Gln Glu Ile Ala Gly His Arg Phe Val Asp Ser Ser Tyr Asp
                690                 695                 700
Tyr Lys Ala Phe Ala Val Thr Tyr Lys Asp Tyr Lys Ile Lys Val Thr
705                 710                 715                 720
Asp Ser Thr Leu Gly Val Thr Asp His Lys Asp Leu Ser Thr Ser Lys
                725                 730                 735
Glu Glu Thr Tyr Lys Val Glu Phe Phe Ser Pro Thr Asn Ser Thr Lys
                740                 745                 750
Pro Val His Glu Ala Lys Val Val Gly Ala Glu Lys Thr Met Met
                755                 760                 765
Val Asn Leu Ala Glu Gly Ala Thr Val Ile Gly Gly Asp Ala Asp Pro
770                 775                 780
Thr Asn Ala Lys Lys Val Phe Asp Gly Leu Leu Asn Asn Asp Thr Thr
785                 790                 795                 800
Ile Leu Ser Thr Ser Asn Lys Ala Ser Ile Phe Glu Leu Lys Glu
                805                 810                 815
Pro Gly Leu Val Lys Tyr Trp Arg Phe Phe Asn Asp Ser Lys Ile Ser
                820                 825                 830
Lys Ala Asp Cys Ile Lys Glu Ala Lys Leu Glu Ala Phe Val Gly His
                835                 840                 845
```

```
Leu Glu Ala Gly Ser Lys Val Lys Asp Ser Leu Glu Lys Ser Ser Lys
    850                 855                 860

Trp Val Thr Val Ser Asp Tyr Ser Gly Glu Asp Gln Glu Phe Ser Gln
865                 870                 875                 880

Pro Leu Asn Asn Ile Gly Ala Lys Tyr Trp Arg Ile Thr Val Asp Thr
                885                 890                 895

Lys Gly Gly Arg Tyr Asn Trp Pro Ser Leu Pro Glu Leu Gln Ile Ile
                900                 905                 910

Gly Tyr Gln Leu Pro Ala Ala Asp Leu Val Met Ala Met Leu Ala Thr
                915                 920                 925

Ala Glu Glu Leu Ser Gln Gln Lys Asp Lys Phe Ser Gln Glu Gln Leu
    930                 935                 940

Lys Glu Leu Glu Val Lys Ile Ala Ala Leu Lys Ala Ala Leu Asp Ser
945                 950                 955                 960

Lys Met Phe Asn Ala Asp Ala Ile Asn Ala Ser Thr Ala Asp Leu Lys
                965                 970                 975

Ala Tyr Val Asp Lys Leu Leu Ala Asp Arg Thr Asp Gln Glu Lys Val
                980                 985                 990

Ala Lys Ala Ala Lys Val Glu Gln Pro Val Ala Thr Asp Ile Lys Glu
    995                 1000                1005

Asn Thr Glu Pro Glu Asn Pro Lys Thr Asp
    1010                1015

<210> SEQ ID NO 18
<211> LENGTH: 1013
<212> TYPE: PRT
<213> ORGANISM: Streptococcus zooepidermicus
<220> FEATURE:
<223> OTHER INFORMATION: Streptococcus zooepidermicus strain H70
      endoglycosidase

<400> SEQUENCE: 18

Met Glu Lys Gln Val Leu Val Lys Lys Thr Leu Lys Cys Val Cys Ala
1               5                   10                  15

Ala Ala Leu Met Val Ala Ile Leu Ala Ala Gln His Asp Ser Leu Val
                20                  25                  30

Thr Val Arg Ala Glu Asp Lys Val Val Gln Thr Ser Pro Ser Val Ser
            35                  40                  45

Ala Ile Asp Asp Leu His Tyr Leu Ser Glu Asn Ser Lys Lys Glu Phe
    50                  55                  60

Lys Glu Glu Leu Ser Lys Ala Gly Val Pro Glu Lys Leu Lys Glu
65                  70                  75                  80

Ile Leu Ser Lys Ala Gln Gln Ala Asp Lys Gln Ala Lys Thr Leu Ala
                85                  90                  95

Glu Met Lys Val Pro Glu Lys Ile Pro Met Lys Pro Leu Lys Gly Pro
            100                 105                 110

Leu Tyr Gly Gly Tyr Phe Arg Thr Trp His Asp Lys Thr Ser Asp Pro
        115                 120                 125

Ala Glu Lys Asp Lys Val Asn Ser Met Gly Glu Leu Pro Lys Glu Val
    130                 135                 140

Asp Leu Ala Phe Val Phe His Asp Trp Thr Lys Asp Tyr Ser Leu Phe
145                 150                 155                 160

Trp Gln Lys Leu Ala Thr Lys His Ile Pro Lys Leu Asn Lys Gln Gly
                165                 170                 175

Thr Arg Val Ile Arg Thr Ile Pro Trp Arg Phe Leu Ala Gly Gly Asp
            180                 185                 190
```

```
His Ser Gly Ile Ala Glu Asp Ala Gln Lys Tyr Pro Asn Thr Pro Glu
        195                 200                 205

Gly Asn Lys Ala Leu Ala Lys Ala Ile Val Asp Glu Tyr Val Tyr Lys
        210                 215                 220

Tyr Asn Leu Asp Gly Leu Asp Val Asp Ile Glu Arg Asp Ser Ile Pro
225                 230                 235                 240

Lys Val Asn Lys Glu Glu Ser Lys Glu Gly Ile Glu Arg Ser Ile Gln
                245                 250                 255

Val Phe Glu Glu Ile Gly Lys Leu Ile Gly Pro Lys Gly Ala Asp Arg
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asp Leu Leu Leu Val Gln Val
        290                 295                 300

Tyr Gly Ala Gln Gly Glu Arg Gly Glu Trp Asp Pro Val Ala Arg Lys
305                 310                 315                 320

Pro Glu Lys Thr Met Glu Arg Trp Glu Ser Tyr Ser Lys Tyr Ile
                325                 330                 335

Arg Pro Glu Gln Tyr Met Val Gly Phe Ser Phe Tyr Glu Glu Asn Ala
                340                 345                 350

Gly Ser Gly Asn Leu Trp Tyr Asp Ile Asn Glu Arg Lys Asp His
        355                 360                 365

Asn Pro Leu His Ser Glu Ile Thr Gly Thr Arg Ala Glu Arg Tyr Ala
370                 375                 380

Lys Trp Gln Pro Lys Thr Gly Val Lys Gly Ile Phe Ser Tyr
385                 390                 395                 400

Ala Ile Asp Arg Asp Gly Val Ala His Gln Pro Glu Lys Tyr Ala Lys
                405                 410                 415

Arg Lys Asp Phe Lys Asp Val Thr Asp Lys Ile Phe His Ser Asp Tyr
                420                 425                 430

Lys Val Ser Lys Ala Leu Lys Glu Val Met Val Lys Asp Lys Ser Tyr
            435                 440                 445

Glu Gln Ile Asp Glu Thr Asp Phe Pro Asp Lys Ala Leu Arg Glu Ala
        450                 455                 460

Val Ile Ala Gln Val Gly Ser Arg Arg Gly Asp Leu Glu Arg Phe Asn
465                 470                 475                 480

Gly Thr Leu Arg Leu Asp Asn Pro Asp Ile Lys Ser Leu Glu Gly Leu
                485                 490                 495

Asn Lys Leu Lys Lys Leu Ala Lys Leu Glu Leu Val Gly Leu Ser Gln
                500                 505                 510

Ile Thr Lys Leu Asp Gln Ser Val Leu Pro Glu Asn Ile Lys Pro Thr
        515                 520                 525

Lys Asp Thr Leu Val Ser Val Leu Glu Ala Tyr Lys Lys Asp Asp Gln
530                 535                 540

Glu Ala Ala Lys Ala Ile Pro Gln Val Ala Leu Thr Ile Ser Gly Leu
545                 550                 555                 560

Thr Gly Leu Lys Glu Leu Asn Leu Ala Gly Phe Glu Arg Glu Thr Leu
                565                 570                 575

Ala Gly Ile Asp Ala Ala Ser Leu Thr Ser Leu Glu Lys Val Asp Leu
            580                 585                 590

Ser Ser Asn Lys Leu Asp Leu Ala Ala Gly Thr Asp Asn Arg Gln Ile
        595                 600                 605
```

```
Leu Asp Thr Met Leu Ala Thr Val Thr Lys His Gly Lys Ala Asn Ala
610                 615                 620
Asp Asn Met Thr Phe Asp His Gln Lys Pro Thr Gly Leu Tyr Pro Asp
625                 630                 635                 640
Thr Tyr Gly Thr Lys Ser Leu Gln Leu Pro Val Ala Asn Asp Thr Ile
            645                 650                 655
Asp Leu Gln Ala Lys Leu Leu Phe Gly Thr Val Thr Asn Gln Gly Thr
                660                 665                 670
Leu Ile Asn Ser Glu Ala Asp Tyr Lys Ala Tyr Gln Glu Gln Glu Ile
            675                 680                 685
Ala Gly Arg Arg Phe Val Asp Pro Ser Tyr Tyr Lys Ala Phe Ala
690                 695                 700
Val Thr Tyr Asp Ala Tyr Lys Val Arg Val Thr Asp Ser Thr Leu Gly
705                 710                 715                 720
Val Thr Asp Glu Lys Lys Leu Ser Thr Ser Lys Glu Thr Tyr Lys
                725                 730                 735
Ile Glu Phe Phe Ser Pro Thr Asn Ser Thr Lys Pro Val His Glu Ala
            740                 745                 750
Lys Val Val Gly Glu Glu Lys Thr Met Met Val Asn Leu Ala Glu
            755                 760                 765
Gly Ala Thr Ile Ile Gly Gly Ser Ala Asp Gln Thr Asn Ala Lys Lys
770                 775                 780
Val Phe Asp Gly Leu Leu Asn Asn Asp Thr Thr Thr Leu Ser Thr Ser
785                 790                 795                 800
Asn Lys Ala Ser Ile Ile Phe Glu Leu Lys Glu Ser Gly Leu Val Lys
            805                 810                 815
His Trp Arg Phe Phe Asn Asp Ser Ala Lys Lys Glu Asp Tyr Ile
            820                 825                 830
Lys Glu Ala Lys Leu Glu Ala Phe Val Gly His Leu Glu Asp Ser Ser
            835                 840                 845
Lys Val Lys Asp Ser Leu Glu Lys Ser Thr Glu Trp Val Thr Val Ser
            850                 855                 860
Asp Tyr Ser Gly Glu Ala Gln Glu Phe Ser Gln Pro Leu Asn Asn Val
865                 870                 875                 880
Gly Ala Lys Tyr Trp Arg Ile Thr Ile Asp Asn Lys Lys Ser Gln Tyr
            885                 890                 895
Gly Tyr Val Ser Leu Pro Glu Leu Gln Leu Ile Gly Tyr Gln Leu Pro
            900                 905                 910
Ala Ala Tyr Pro Val Met Ala Thr Leu Ala Ala Glu Glu Leu Ser
            915                 920                 925
Gln Gln Lys Asp Lys Phe Ser Gln Lys Gln Leu Lys Glu Leu Glu Val
930                 935                 940
Lys Val Ala Ala Leu Lys Ala Leu Asp Asn Lys Met Phe Asn Ala
945                 950                 955                 960
Asp Thr Ile Asn Ala Ser Phe Ala Asp Val Lys Ala Tyr Val Asp Lys
            965                 970                 975
Leu Leu Ala Asp Ala Ala Gly Lys Lys Thr Pro Gly Lys Ala Thr Lys
                980                 985                 990
Glu Ala Gln Leu Val Thr Thr Asp Ala Lys Glu Lys Ala Glu Ser Glu
            995                 1000                1005
Lys Ser Lys Ala Asp
    1010
```

-continued

```
<210> SEQ ID NO 19
<211> LENGTH: 1057
<212> TYPE: PRT
<213> ORGANISM: Artificial Sequence
<220> FEATURE:
<223> OTHER INFORMATION: synthetic EndoS homologue consensus sequence
<220> FEATURE:
<221> NAME/KEY: VARIANT
<222> LOCATION: (1)...(18)
<223> OTHER INFORMATION: Xaa = any naturally occurring amino acid, may
      be present or absent
<220> FEATURE:
<221> NAME/KEY: VARIANT
<222> LOCATION: (288)...(436)
<223> OTHER INFORMATION: Xaa = any naturally occurring amino acid
<220> FEATURE:
<221> NAME/KEY: VARIANT
<222> LOCATION: (437)...(445)
<223> OTHER INFORMATION: Xaa = any naturally occurring amino acid, may
      be present or absent
<220> FEATURE:
<221> NAME/KEY: VARIANT
<222> LOCATION: (447)...(886)
<223> OTHER INFORMATION: Xaa = any naturally occurring amino acid
<220> FEATURE:
<221> NAME/KEY: VARIANT
<222> LOCATION: (1027)...(1057)
<223> OTHER INFORMATION: Xaa = any naturally occurring amino acid, may
      be present or absent

<400> SEQUENCE: 19

Xaa Xaa Xaa Xaa Xaa Xaa Xaa Xaa Xaa Xaa Xaa Xaa Xaa Xaa Xaa Xaa
 1               5                   10                  15

Xaa Xaa Met Asp Lys His Leu Leu Val Lys Arg Thr Leu Gly Cys Val
            20                  25                  30

Cys Ala Ala Thr Leu Met Gly Ala Ala Leu Ala Thr His His Asp Ser
         35                  40                  45

Leu Asn Thr Val Lys Ala Glu Glu Lys Thr Val Gln Val Gln Lys Glu
 50                  55                  60

Leu Ser Ser Ile Asp Ser Leu His Tyr Leu Ser Glu Asn Ser Lys Lys
 65                  70                  75                  80

Glu Phe Lys Glu Glu Leu Ser Lys Ala Gly Gln Glu Ser Gln Lys Val
                 85                  90                  95

Lys Glu Ile Leu Ala Lys Ala Gln Gln Ala Asp Lys Gln Ala Gln Glu
            100                 105                 110

Leu Ala Lys Met Lys Ile Pro Glu Lys Ile Pro Met Lys Pro Leu His
        115                 120                 125

Gly Pro Leu Tyr Gly Gly Tyr Phe Arg Thr Trp His Asp Lys Thr Ser
    130                 135                 140

Asp Pro Thr Glu Lys Asp Lys Val Asn Ser Met Gly Glu Leu Pro Lys
145                 150                 155                 160

Glu Val Asp Leu Ala Phe Ile Phe His Asp Trp Thr Lys Asp Tyr Ser
                165                 170                 175

Leu Phe Trp Lys Glu Leu Ala Thr Lys His Val Pro Lys Leu Asn Lys
            180                 185                 190

Gln Gly Thr Arg Val Ile Arg Thr Ile Pro Trp Arg Phe Leu Ala Gly
        195                 200                 205

Gly Asp Asn Ser Gly Ile Ala Glu Asp Thr Ser Lys Tyr Pro Asn Thr
    210                 215                 220

Pro Glu Gly Asn Lys Ala Leu Ala Lys Ala Ile Val Asp Glu Tyr Val
225                 230                 235                 240

Tyr Lys Tyr Asn Leu Asp Gly Leu Asp Val Asp Val Glu His Asp Ser
                245                 250                 255
```

```
Ile Pro Lys Val Asn Gly Glu Ala Ser Asp Glu Asn Leu Lys Arg Ser
            260                 265                 270

Ile Asp Val Phe Glu Glu Ile Gly Lys Leu Ile Gly Pro Lys Gly Xaa
        275                 280                 285

Asp Lys Ser Arg Leu Phe Ile Met Asp Ser Thr Tyr Met Ala Asp Lys
    290                 295                 300

Asn Pro Leu Ile Glu Arg Gly Ala Pro Tyr Ile Asp Leu Leu Leu Val
305                 310                 315                 320

Gln Val Tyr Gly Ser Gln Gly Glu Lys Gly Xaa Phe Gln Asn Asp Thr
                325                 330                 335

Xaa Leu Val Thr Xaa Thr Pro Glu Glu Arg Trp Gln Gly Tyr Ser Lys
            340                 345                 350

Tyr Ile Arg Pro Glu Gln Tyr Met Ile Gly Phe Ser Phe Tyr Glu Glu
        355                 360                 365

Arg Ala Gly Ser Gly Asn Leu Trp Tyr Asp Ile Asn Ser Arg Lys Asp
    370                 375                 380

Glu Asp Lys Ala Asn Gly Ile Asn Thr Asp Ile Thr Gly Thr Arg Ala
385                 390                 395                 400

Glu Arg Tyr Ala Arg Trp Gln Pro Lys Thr Gly Gly Val Lys Gly Gly
                405                 410                 415

Ile Phe Ser Tyr Ala Ile Asp Arg Asp Gly Val Ala His Gln Pro Lys
            420                 425                 430

Lys Xaa Ala Xaa Xaa Xaa Lys Xaa Xaa Xaa Xaa Xaa Xaa Gln Xaa Xaa
        435                 440                 445

Xaa Xaa Xaa Ile Thr Asp Asn Ile Phe His Ser Asp Tyr Ser Val Ser
    450                 455                 460

Lys Ala Leu Lys Thr Val Met Leu Lys Asp Lys Ser Tyr Asp Leu Ile
465                 470                 475                 480

Asp Glu Lys Asp Phe Pro Asp Lys Ala Leu Arg Glu Ala Val Met Ala
                485                 490                 495

Gln Val Gly Thr Arg Lys Gly Asp Leu Glu Arg Phe Asn Gly Thr Leu
            500                 505                 510

Arg Leu Asp Asn Pro Ala Ile Gln Ser Leu Glu Gly Leu Asn Lys Phe
        515                 520                 525

Lys Lys Leu Ala Gln Leu Asp Leu Ile Gly Leu Ser Arg Ile Thr Lys
    530                 535                 540

Leu Asp Gln Ser Val Leu Pro Ala Asn Met Lys Pro Gly Lys Asp Thr
545                 550                 555                 560

Leu Glu Thr Val Leu Glu Thr Tyr Lys Lys Asp Asn Lys Glu Glu Pro
                565                 570                 575

Ala Thr Ile Pro Pro Val Ser Leu Lys Val Ser Gly Leu Thr Gly Leu
            580                 585                 590

Lys Glu Leu Asp Leu Ser Gly Phe Asp Arg Glu Thr Leu Ala Gly Leu
        595                 600                 605

Asp Ala Ala Thr Leu Thr Ser Leu Glu Lys Val Asp Ile Ser Gly Asn
    610                 615                 620

Lys Leu Asp Leu Ala Pro Gly Thr Glu Asn Arg Gln Ile Phe Asp Thr
625                 630                 635                 640

Met Leu Ser Thr Val Ser Asn His Val Gly Ser Asn Glu Gln Thr Val
                645                 650                 655

Lys Phe Asp Lys Gln Lys Pro Thr Gly His Tyr Pro Asp Thr Tyr Gly
            660                 665                 670
```

```
Lys Thr Ser Leu Arg Leu Pro Val Ala Asn Glu Lys Val Asp Leu Gln
            675                 680                 685

Ser Gln Leu Leu Phe Gly Thr Val Thr Asn Gln Gly Thr Leu Ile Asn
        690                 695                 700

Ser Glu Ala Asp Tyr Lys Ala Tyr Gln Asn His Lys Ile Ala Gly Arg
705                 710                 715                 720

Ser Phe Val Asp Ser Asn Tyr His Tyr Asn Asn Phe Lys Val Ser Tyr
                725                 730                 735

Glu Asn Tyr Thr Val Lys Val Thr Asp Ser Thr Leu Gly Thr Thr Thr
            740                 745                 750

Asp Lys Thr Leu Ala Thr Asp Lys Glu Thr Tyr Lys Val Asp Phe
        755                 760                 765

Phe Ser Pro Ala Asp Lys Thr Lys Ala Val His Thr Ala Lys Val Ile
770                 775                 780

Val Gly Asp Glu Lys Thr Met Met Val Asn Leu Ala Glu Gly Ala Thr
785                 790                 795                 800

Val Ile Gly Gly Ser Ala Asp Pro Val Asn Ala Arg Lys Val Phe Asp
                805                 810                 815

Gly Gln Leu Gly Ser Glu Thr Asp Asn Ile Ser Leu Gly Trp Asp Ser
            820                 825                 830

Lys Gln Ser Ile Ile Phe Lys Leu Lys Glu Asp Gly Leu Ile Lys His
        835                 840                 845

Trp Arg Phe Phe Asn Asp Ser Ala Arg Asn Pro Xaa Thr Thr Asn Lys
    850                 855                 860

Xaa Xaa Pro Ile Gln Glu Ala Ser Leu Gln Ile Phe Asn Ile Lys Asp
865                 870                 875                 880

Tyr Asn Leu Asp Xaa Xaa Asn Leu Leu Glu Asn Pro Asn Lys Phe Asp
                885                 890                 895

Asp Glu Lys Tyr Trp Ile Thr Val Asp Thr Tyr Ser Ala Gln Gly Glu
            900                 905                 910

Arg Ala Thr Ala Phe Ser Asn Thr Leu Asn Asn Ile Thr Ser Lys Tyr
        915                 920                 925

Trp Arg Val Val Phe Asp Thr Lys Gly Asp Arg Tyr Ser Ser Pro Val
    930                 935                 940

Val Pro Glu Leu Gln Ile Leu Gly Tyr Pro Leu Pro Asn Ala Asp Thr
945                 950                 955                 960

Ile Met Lys Thr Val Thr Thr Ala Lys Gly Leu Ser Gln Gln Lys Asp
                965                 970                 975

Lys Phe Ser Gln Lys Met Leu Asp Glu Leu Lys Ile Lys Glu Met Ala
            980                 985                 990

Leu Glu Thr Ser Leu Asn Ser Lys Ile Phe Asp Val Thr Ala Ile Asn
        995                 1000                1005

Ala Asn Ala Gly Val Leu Lys Asp Cys Ile Glu Lys Arg Gln Leu Leu
    1010                1015                1020

Lys Lys Xaa Xaa Xaa Xaa Xaa Xaa Xaa Xaa Xaa Xaa Xaa Xaa Xaa Xaa
1025                1030                1035                1040

Xaa Xaa Xaa Xaa Xaa Xaa Xaa Xaa Xaa Xaa Xaa Xaa Xaa Xaa Xaa
                1045                1050                1055

Xaa

<210> SEQ ID NO 20
<211> LENGTH: 409
<212> TYPE: PRT
<213> ORGANISM: Artificial Sequence
```

<220> FEATURE:
<223> OTHER INFORMATION: synthetic Streptococcus pyogenes serotype M1
    strain AP1 secreted endoglycosidase EndoS
    alpha-domain

<400> SEQUENCE: 20

```
Glu Glu Lys Thr Val Gln Val Gln Lys Gly Leu Pro Ser Ile Asp Ser
 1               5                  10                  15

Leu His Tyr Leu Ser Glu Asn Ser Lys Lys Glu Phe Lys Glu Glu Leu
             20                  25                  30

Ser Lys Ala Gly Gln Glu Ser Gln Lys Val Lys Glu Ile Leu Ala Lys
         35                  40                  45

Ala Gln Gln Ala Asp Lys Gln Ala Gln Glu Leu Ala Lys Met Lys Ile
     50                  55                  60

Pro Glu Lys Ile Pro Met Lys Pro Leu His Gly Pro Leu Tyr Gly Gly
 65                  70                  75                  80

Tyr Phe Arg Thr Trp His Asp Lys Thr Ser Asp Pro Thr Glu Lys Asp
             85                  90                  95

Lys Val Asn Ser Met Gly Glu Leu Pro Lys Glu Val Asp Leu Ala Phe
        100                 105                 110

Ile Phe His Asp Trp Thr Lys Asp Tyr Ser Leu Phe Trp Lys Glu Leu
    115                 120                 125

Ala Thr Lys His Val Pro Lys Leu Asn Lys Gln Gly Thr Arg Val Ile
130                 135                 140

Arg Thr Ile Pro Trp Arg Phe Leu Ala Gly Gly Asp Asn Ser Gly Ile
145                 150                 155                 160

Ala Glu Asp Thr Ser Lys Tyr Pro Asn Thr Pro Glu Gly Asn Lys Ala
                165                 170                 175

Leu Ala Lys Ala Ile Val Asp Glu Tyr Val Tyr Lys Tyr Asn Leu Asp
            180                 185                 190

Gly Leu Asp Val Asp Val Glu His Asp Ser Ile Pro Lys Val Asp Lys
        195                 200                 205

Lys Glu Asp Thr Ala Gly Val Glu Arg Ser Ile Gln Val Phe Glu Glu
    210                 215                 220

Ile Gly Lys Leu Ile Gly Pro Lys Gly Val Asp Lys Ser Arg Leu Phe
225                 230                 235                 240

Ile Met Asp Ser Thr Tyr Met Ala Asp Lys Asn Pro Leu Ile Glu Arg
                245                 250                 255

Gly Ala Pro Tyr Ile Asn Leu Leu Leu Val Gln Val Tyr Gly Ser Gln
            260                 265                 270

Gly Glu Lys Gly Gly Trp Glu Pro Val Ser Asn Arg Pro Glu Lys Thr
        275                 280                 285

Met Glu Glu Arg Trp Gln Gly Tyr Ser Lys Tyr Ile Arg Pro Glu Gln
    290                 295                 300

Tyr Met Ile Gly Phe Ser Phe Tyr Glu Glu Asn Ala Gln Glu Gly Asn
305                 310                 315                 320

Leu Trp Tyr Asp Ile Asn Ser Arg Lys Asp Glu Asp Lys Ala Asn Gly
                325                 330                 335

Ile Asn Thr Asp Ile Thr Gly Thr Arg Ala Glu Arg Tyr Ala Arg Trp
            340                 345                 350

Gln Pro Lys Thr Gly Gly Val Lys Gly Gly Ile Phe Ser Tyr Ala Ile
        355                 360                 365

Asp Arg Asp Gly Val Ala His Gln Pro Lys Lys Tyr Ala Lys Gln Lys
    370                 375                 380
```

```
Glu Phe Lys Asp Ala Thr Asp Asn Ile Phe His Ser Asp Tyr Ser Val
385                 390                 395                 400

Ser Lys Ala Leu Lys Thr Val Met Leu
                405
```

<210> SEQ ID NO 21
<211> LENGTH: 335
<212> TYPE: PRT
<213> ORGANISM: Elizabethkingia meningoseptica
<220> FEATURE:
<223> OTHER INFORMATION: Elizabethkingia meningoseptica EndoF-2

<400> SEQUENCE: 21

```
Met Lys Thr Ala Asn Phe Ser Phe Ala Leu Cys Leu Ser Val Val Ile
  1               5                  10                  15

Met Leu Phe Ile Lys Cys Thr Arg Ser Glu Gln Asp Leu Ser Val Thr
                 20                  25                  30

Lys Asp Ala Ile Ala Gln Lys Ser Gly Val Thr Val Ser Ala Val Asn
             35                  40                  45

Leu Ser Asn Leu Ile Ala Tyr Lys Asn Ser Asp His Gln Ile Ser Ala
         50                  55                  60

Gly Tyr Tyr Arg Thr Trp Arg Asp Ser Ala Thr Ala Ser Gly Asn Leu
 65                  70                  75                  80

Pro Ser Met Arg Trp Leu Pro Asp Ser Leu Asp Met Val Met Val Phe
                 85                  90                  95

Pro Asp Tyr Thr Pro Pro Glu Asn Ala Tyr Trp Asn Thr Leu Lys Thr
                100                 105                 110

Asn Tyr Val Pro Tyr Leu His Lys Arg Gly Thr Lys Val Ile Ile Thr
            115                 120                 125

Leu Gly Asp Leu Asn Ser Ala Thr Thr Thr Gly Gly Gln Asp Ser Ile
        130                 135                 140

Gly Tyr Ser Ser Trp Ala Lys Gly Ile Tyr Asp Lys Trp Val Gly Glu
145                 150                 155                 160

Tyr Asn Leu Asp Gly Ile Asp Ile Asp Ile Glu Ser Ser Pro Ser Gly
                165                 170                 175

Ala Thr Leu Thr Lys Phe Val Ala Ala Thr Lys Ala Leu Ser Lys Tyr
            180                 185                 190

Phe Gly Pro Lys Ser Gly Thr Gly Lys Thr Phe Val Tyr Asp Thr Asn
        195                 200                 205

Gln Asn Pro Thr Asn Phe Phe Ile Gln Thr Ala Pro Arg Tyr Asn Tyr
    210                 215                 220

Val Phe Leu Gln Ala Tyr Gly Arg Ser Thr Thr Asn Leu Thr Thr Val
225                 230                 235                 240

Ser Gly Leu Tyr Ala Pro Tyr Ile Ser Met Lys Gln Phe Leu Pro Gly
                245                 250                 255

Phe Ser Phe Tyr Glu Glu Asn Gly Tyr Pro Gly Asn Tyr Trp Asn Asp
            260                 265                 270

Val Arg Tyr Pro Gln Asn Gly Thr Gly Arg Ala Tyr Asp Tyr Ala Arg
        275                 280                 285

Trp Gln Pro Ala Thr Gly Lys Lys Gly Gly Val Phe Ser Tyr Ala Ile
    290                 295                 300

Glu Arg Asp Ala Pro Leu Thr Ser Ser Asn Asp Asn Thr Leu Arg Ala
305                 310                 315                 320

Pro Asn Phe Arg Val Thr Lys Asp Leu Ile Lys Ile Met Asn Pro
                325                 330                 335
```

<210> SEQ ID NO 22
<211> LENGTH: 379
<212> TYPE: PRT
<213> ORGANISM: Corynebacterium pseudotuberculosis
<220> FEATURE:
<223> OTHER INFORMATION: Corynebacterium pseudotuberculosis CP40

<400> SEQUENCE: 22

```
Met His Asn Ser Pro Arg Ser Val Ser Arg Leu Ile Thr Val Gly Ile
1               5                   10                  15

Thr Ser Ala Leu Phe Ala Ser Thr Phe Ser Ala Val Ala Ser Ala Glu
            20                  25                  30

Ser Ala Thr Leu Ser Lys Glu Pro Leu Lys Ala Ser Pro Gly Arg Ala
        35                  40                  45

Asp Thr Val Gly Val Gln Thr Thr Cys Asn Ala Lys Pro Ile Phe Phe
    50                  55                  60

Gly Tyr Tyr Arg Thr Trp Arg Asp Lys Ala Ile Gln Leu Lys Asp Asp
65                  70                  75                  80

Asp Pro Trp Lys Asp Lys Leu Gln Val Lys Leu Thr Asp Ile Pro Glu
                85                  90                  95

His Val Asn Met Val Ser Leu Phe His Val Glu Asp Asn Gln Lys Ser
            100                 105                 110

Asp Gln Gln Phe Trp Glu Thr Phe His Arg Glu Tyr Gln Pro Glu Leu
        115                 120                 125

Lys Lys Arg Gly Thr Arg Val Val Arg Thr Val Gly Ala Gln Leu Leu
    130                 135                 140

Leu Asn Lys Ile Lys Asp Lys Asn Leu Tyr Gly Lys His Val Glu Asp
145                 150                 155                 160

Asp Tyr Lys Tyr Arg Glu Ile Ala Arg Asp Val Tyr Asn Glu Tyr Val
                165                 170                 175

Val Lys His Asn Leu Asp Gly Leu Asp Val Asp Met Glu Leu Arg Gln
            180                 185                 190

Val Glu Lys Gln Leu Asn Leu Lys Trp Gln Leu Arg Lys Ile Met Gly
        195                 200                 205

Ala Phe Ser Glu Leu Met Gly Pro Lys Ala Pro Ala Asn Glu Gly Lys
    210                 215                 220

Lys Pro Asp His Glu Gly Tyr Lys Tyr Leu Ile Tyr Asp Thr Phe Asp
225                 230                 235                 240

Asn Ala Gln Thr Ser Gln Val Gly Leu Val Ala Asp Leu Val Asp Tyr
                245                 250                 255

Val Leu Ala Gln Thr Tyr Lys Lys Asp Thr Lys Glu Ser Val Thr Gln
            260                 265                 270

Val Trp Asn Gly Phe Arg Asp Lys Ile Asn Ser Cys Gln Phe Met Ala
        275                 280                 285

Gly Tyr Ala His Pro Glu Glu Asn Asp Thr Asn Arg Phe Leu Thr Ala
    290                 295                 300

Val Gly Glu Val Asn Lys Ser Gly Ala Met Gln Val Ala Glu Trp Lys
305                 310                 315                 320

Pro Glu Gly Gly Glu Lys Gly Gly Thr Phe Ala Tyr Ala Leu Asp Arg
                325                 330                 335

Asp Gly Arg Thr Tyr Asp Gly Asp Asp Phe Thr Thr Leu Lys Pro Thr
            340                 345                 350

Asp Phe Ala Phe Thr Lys Arg Ala Ile Glu Leu Thr Thr Gly Glu Ser
        355                 360                 365
```

Ser Thr Asp Leu Gly Lys Pro Thr Gly Ser Arg
    370                 375

<210> SEQ ID NO 23
<211> LENGTH: 433
<212> TYPE: PRT
<213> ORGANISM: Artificial Sequence
<220> FEATURE:
<223> OTHER INFORMATION: synthetic S. pyogenes EndoS alpha-domain/E.
      mening

```
          be present or absent
<220> FEATURE:
<221> NAME/KEY: VARIANT
<222> LOCATION: (212)...(215)
<223> OTHER INFORMATION: Xaa = any naturally occurring amino acid
<220> FEATURE:
<221> NAME/KEY: VARIANT
<222> LOCATION: (216)...(221)
<223> OTHER INFORMATION: Xaa = any naturally occurring amino acid, may
      be present or absent
<220> FEATURE:
<221> NAME/KEY: VARIANT
<222> LOCATION: (223)...(238)
<223> OTHER INFORMATION: Xaa = any naturally occurring amino acid
<220> FEATURE:
<221> NAME/KEY: VARIANT
<222> LOCATION: (242)...(243)
<223> OTHER INFORMATION: Xaa = any naturally occurring amino acid, may
      be present or absent
<220> FEATURE:
<221> NAME/KEY: VARIANT
<222> LOCATION: (244)...(246)
<223> OTHER INFORMATION: Xaa = any naturally occurring amino acid
<220> FEATURE:
<221> NAME/KEY: VARIANT
<222> LOCATION: (249)...(256)
<223> OTHER INFORMATION: Xaa = any naturally occurring amino acid, may
      be present or absent
<220> FEATURE:
<221> NAME/KEY: VARIANT
<222> LOCATION: (257)...(264)
<223> OTHER INFORMATION: Xaa = any naturally occurring amino acid
<220> FEATURE:
<221> NAME/KEY: VARIANT
<222> LOCATION: (267)...(270)
<223> OTHER INFORMATION: Xaa = any naturally occurring amino acid, may
      be present or absent
<220> FEATURE:
<221> NAME/KEY: VARIANT
<222> LOCATION: (271)...(286)
<223> OTHER INFORMATION: Xaa = any naturally occurring amino acid
<220> FEATURE:
<221> NAME/KEY: VARIANT
<222> LOCATION: (289)...(301)
<223> OTHER INFORMATION: Xaa = any naturally occurring amino acid, may
      be present or absent
<220> FEATURE:
<221> NAME/KEY: VARIANT
<222> LOCATION: (303)...(334)
<223> OTHER INFORMATION: Xaa = any naturally occurring amino acid
<220> FEATURE:
<221> NAME/KEY: VARIANT
<222> LOCATION: (335)...(335)
<223> OTHER INFORMATION: Xaa = any naturally occurring amino acid, may
      be present or absent
<220> FEATURE:
<221> NAME/KEY: VARIANT
<222> LOCATION: (336)...(341)
<223> OTHER INFORMATION: Xaa = any naturally occurring amino acid
<220> FEATURE:
<221> NAME/KEY: VARIANT
<222> LOCATION: (344)...(351)
<223> OTHER INFORMATION: Xaa = any naturally occurring amino acid, may
      be present or absent
<220> FEATURE:
<221> NAME/KEY: VARIANT
<222> LOCATION: (352)...(352)
<223> OTHER INFORMATION: Xaa = any naturally occurring amino acid
<220> FEATURE:
<221> NAME/KEY: VARIANT
<222> LOCATION: (355)...(362)
<223> OTHER INFORMATION: Xaa = any naturally occurring amino acid, may
      be present or absent
<220> FEATURE:
<221> NAME/KEY: VARIANT
<222> LOCATION: (365)...(373)
<223> OTHER INFORMATION: Xaa = any naturally occurring amino acid
<220> FEATURE:
<221> NAME/KEY: VARIANT
```

```
<222> LOCATION: (376)...(376)
<223> OTHER INFORMATION: Xaa = any naturally occurring amino acid, may
      be present or absent
<220> FEATURE:
<221> NAME/KEY: VARIANT
<222> LOCATION: (377)...(381)
<223> OTHER INFORMATION: Xaa = any naturally occurring amino acid
<220> FEATURE:
<221> NAME/KEY: VARIANT
<222> LOCATION: (390)...(403)
<223> OTHER INFORMATION: Xaa = any naturally occurring amino acid, may
      be present or absent
<220> FEATURE:
<221> NAME/KEY: VARIANT
<222> LOCATION: (404)...(412)
<223> OTHER INFORMATION: Xaa = any naturally occurring amino acid
<220> FEATURE:
<221> NAME/KEY: VARIANT
<222> LOCATION: (415)...(415)
<223> OTHER INFORMATION: Xaa = any naturally occurring amino acid, may
      be present or absent
<220> FEATURE:
<221> NAME/KEY: VARIANT
<222> LOCATION: (416)...(428)
<223> OTHER INFORMATION: Xaa = any naturally occurring amino acid
<220> FEATURE:
<221> NAME/KEY: VARIANT
<222> LOCATION: (430)...(433)
<223> OTHER INFORMATION: Xaa = any naturally occurring amino acid, may
      be present or absent

<400> SEQUENCE: 23

Xaa Xaa Xaa Lys Thr Xaa Xaa Val Ser Xaa Xaa Leu Xaa Xaa Xaa Xaa
 1               5                  10                  15

Xaa Xaa Xaa Leu Phe Xaa Xaa Xaa Xaa Xaa Xaa Xaa Xaa Xaa Xaa Xaa
             20                  25                  30

Xaa Xaa Xaa Xaa Xaa Xaa Glu Xaa Gln Xaa Xaa Xaa Xaa Ser Xaa Xaa
         35                  40                  45

Lys Ala Xaa Xaa Ala Xaa Lys Xaa Xaa Xaa Xaa Xaa Xaa Xaa Xaa Xaa
 50                  55                  60

Xaa Xaa Xaa Xaa Ile Xaa Xaa Lys Xaa Xaa Xaa Pro Ile Xaa Xaa Xaa
 65                  70                  75                  80

Gly Tyr Tyr Arg Thr Trp Arg Asp Lys Ala Xaa Xaa Xaa Xaa Xaa Xaa
                 85                  90                  95

Asp Xaa Xaa Xaa Xaa Xaa Xaa Xaa Ser Met Xaa Xaa Leu Pro Xaa
             100                 105                 110

Xaa Val Asp Met Val Xaa Xaa Phe His Asp Xaa Thr Xaa Xaa Xaa Ser
             115                 120                 125

Xaa Xaa Xaa Phe Trp Xaa Thr Leu Xaa Thr Xaa Tyr Val Pro Xaa Leu
         130                 135                 140

Xaa Lys Arg Gly Thr Arg Val Ile Arg Thr Xaa Xaa Xaa Xaa Xaa
145                 150                 155                 160

Xaa Gly Xaa Leu Asn Ser Xaa Xaa Xaa Xaa Thr Xaa Gly Xaa Xaa
                 165                 170                 175

Xaa Xaa Xaa Xaa Xaa Gly Tyr Xaa Xaa Xaa Ala Lys Xaa Ile Tyr Asp
             180                 185                 190

Glu Tyr Val Xaa Lys Tyr Asn Leu Asp Gly Leu Asp Val Asp Xaa Glu
         195                 200                 205

Xaa Ser Xaa Pro Lys Xaa Xaa Xaa Xaa Xaa Xaa Ala Xaa Xaa
         210                 215                 220

Xaa Xaa Xaa Xaa Xaa Xaa Xaa Ala Xaa Ser Lys Leu Xaa Gly Pro
225                 230                 235                 240

Lys Xaa Xaa Xaa Xaa Xaa Gly Lys Xaa Xaa Xaa Xaa Xaa Xaa Xaa
```

```
                        245                 250                 255
Xaa Phe Ile Tyr Asp Thr Xaa Xaa Asn Ala Xaa Thr Asn Xaa Xaa Xaa
                    260                 265                 270

Xaa Xaa Xaa Ala Pro Xaa Xaa Asn Tyr Val Leu Xaa Gln Xaa Tyr Gly
            275                 280                 285

Xaa Xaa Xaa Xaa Xaa Xaa Xaa Xaa Xaa Xaa Xaa Xaa Arg Xaa Xaa
        290                 295                 300

Xaa Xaa Xaa Thr Xaa Val Trp Xaa Gly Tyr Xaa Xaa Tyr Ile Xaa Xaa
305                 310                 315                 320

Xaa Gln Phe Met Xaa Gly Phe Ser Phe Tyr Glu Glu Asn Xaa Xaa Xaa
                    325                 330                 335

Gly Asn Xaa Trp Xaa Asp Val Xaa Xaa Arg Xaa Xaa Xaa Xaa Xaa
                340                 345                 350

Asn Gly Xaa Xaa Xaa Xaa Xaa Thr Gly Xaa Arg Ala Xaa Xaa Tyr Ala
            355                 360                 365

Arg Trp Gln Pro Xaa Thr Gly Xaa Xaa Lys Gly Gly Xaa Phe Ser Tyr
                    370                 375                 380

Ala Ile Asp Arg Asp Gly Xaa Xaa Xaa Pro Xaa Xaa Xaa Xaa
385                 390                 395                 400

Xaa Xaa Xaa Xaa Xaa Xaa Xaa Asp Asn Thr Xaa Arg Ala Xaa Xaa
                405                 410                 415

Xaa Xaa Val Xaa Lys Xaa Leu Xaa Xaa Met Xaa Pro Xaa Xaa Xaa
            420                 425                 430

Xaa

<210> SEQ ID NO 24
<211> LENGTH: 9
<212> TYPE: PRT
<213> ORGANISM: Artificial Sequence
<220> FEATURE:
<223> OTHER INFORMATION: synthetic EndoS alpha-domain chitinase family
      18 active site motif, residues 191-199 of SEQ ID NO:1, residues
      227-235 of SEQ ID NO:2

<400> SEQUENCE: 24

Leu Asp Gly Leu Asp Val Asp Val Glu
1               5

<210> SEQ ID NO 25
<211> LENGTH: 10
<212> TYPE: PRT
<213> ORGANISM: Artificial Sequence
<220> FEATURE:
<223> OTHER INFORMATION: synthetic EndoS beta-domain streptococcal
      cysteine proteinase SpeB cleavage site

<400> SEQUENCE: 25

Lys Thr Val Met Leu Lys Asp Lys Ser Tyr
1               5                   10

<210> SEQ ID NO 26
<211> LENGTH: 24
<212> TYPE: DNA
<213> ORGANISM: Artificial Sequence
<220> FEATURE:
<223> OTHER INFORMATION: synthetic ndoS sequence PCR amplification
      forward primer

<400> SEQUENCE: 26
actgggatcc cggaggagaa gact                                          24
```

```
<210> SEQ ID NO 27
<211> LENGTH: 24
<212> TYPE: DNA
<213> ORGANISM: Artificial Sequence
<220> FEATURE:
<223> OTHER INFORMATION: synthetic ndoS sequence PCR amplification
      reverse primer

<400> SEQUENCE: 27
ttaatctcga ggttgctatc taag                                          24

<210> SEQ ID NO 28
<211> LENGTH: 12
<212> TYPE: PRT
<213> ORGANISM: Artificial Sequence
<220> FEATURE:
<223> OTHER INFORMATION: synthetic M2139 collagen type II (CII) specific
      mAb J1 epitope

<400> SEQUENCE: 28

Gly Glu Arg Gly Ala Ala Gly Ile Ala Gly Pro Lys
1               5                   10

<210> SEQ ID NO 29
<211> LENGTH: 5
<212> TYPE: PRT
<213> ORGANISM: Artificial Sequence
<220> FEATURE:
<223> OTHER INFORMATION: synthetic CIIC1 collagen type II (CII) specific
      mAb I-C1 epitope

<400> SEQUENCE: 29

Ala Arg Gly Leu Thr
1               5
```